(12) United States Patent
Will

(10) Patent No.: US 7,741,467 B2
(45) Date of Patent: Jun. 22, 2010

(54) NON-FLUORESCENT ENERGY TRANSFER

(75) Inventor: Stephen G. Will, Oakland, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 312 days.

(21) Appl. No.: 11/544,460

(22) Filed: Oct. 5, 2006

(65) Prior Publication Data

US 2007/0077588 A1 Apr. 5, 2007

Related U.S. Application Data

(60) Provisional application No. 60/724,202, filed on Oct. 5, 2005.

(51) Int. Cl.
*C07H 21/04* (2006.01)
(52) U.S. Cl. .................................................. 536/24.3
(58) Field of Classification Search .................. None
See application file for complete search history.

(56) References Cited

U.S. PATENT DOCUMENTS

| | | | |
|---|---|---|---|
| 4,318,846 A | 3/1982 | Khanna et al. | |
| 4,458,066 A | 7/1984 | Caruthers et al. | |
| 5,188,934 A | 2/1993 | Menchen et al. | |
| 5,366,860 A | 11/1994 | Bergot et al. | |
| 5,434,088 A | 7/1995 | Ikeda et al. | |
| 5,565,322 A * | 10/1996 | Heller ........................... | 435/6 |
| 5,688,648 A | 11/1997 | Mathies et al. | |
| 5,800,996 A | 9/1998 | Lee et al. | |
| 5,863,727 A | 1/1999 | Lee et al. | |
| 5,928,907 A | 7/1999 | Woudneberg et al. | |
| 5,945,526 A | 8/1999 | Lee et al. | |
| 6,114,518 A | 9/2000 | Pitner et al. | |
| 6,117,635 A | 9/2000 | Nazarenko et al. | |
| 6,214,979 B1 | 4/2001 | Gelfand et al. | |
| 6,335,440 B1 | 1/2002 | Lee et al. | |
| 6,573,054 B2 | 6/2003 | Patel et al. | |
| 6,610,842 B1 | 8/2003 | Ravikumar et al. | |
| 6,734,297 B2 | 5/2004 | Kempe | |
| 6,768,000 B1 | 7/2004 | Nardone et al. | |
| 6,821,727 B1 | 11/2004 | Livak et al. | |
| 2003/0143594 A1 | 7/2003 | Mathies et al. | |
| 2003/0175785 A1 | 9/2003 | Patel et al. | |
| 2004/0197793 A1 | 10/2004 | Hassibi et al. | |
| 2005/0164316 A1 | 7/2005 | Bray | |
| 2005/0287548 A1* | 12/2005 | Bao et al. ....................... | 435/6 |

FOREIGN PATENT DOCUMENTS

| | | |
|---|---|---|
| EP | 0 050 684 A1 | 10/1980 |
| EP | 0 144 914 A2 | 11/1984 |
| EP | 0 476 545 A1 | 9/1991 |
| EP | 1 067 134 B1 | 1/2001 |
| WO | WO 93/09128 A1 | 5/1993 |
| WO | WO 01/14612 A1 | 4/1998 |
| WO | WO 00/06778 A1 | 2/2000 |
| WO | WO 01/86001 A1 | 11/2001 |
| WO | WO 03/002975 A2 | 1/2003 |
| WO | WO 03/043402 A2 | 5/2003 |
| WO | WO 2005/030979 A2 | 4/2005 |
| WO | EP2006/009646 | 1/2007 |
| WO | EP2006/009646 | 4/2007 |

OTHER PUBLICATIONS

Afonina, I., et al, 2002, "Single Nucleotide Polymorphism Detection with MGB Eclipse™ Assays", *Journal of Clinical Ligand Assay*, 25 (3): 268-275.
Bonnet, G., et al, 1999, "Thermodynamic basis of the enhanced specificity of structured DNA probes", *Proc. Natl. Acad. Sci. USA*, 96: 6171-6176.
Gullberg, M., et al, 2004, "Cytokine detection by antibody-based proximity ligation", *Proceedings of the National Academy of Sciences of the USA*, 101(22): 8420-8424.
Ju, J., et al, 1995, "Fluorescence energy transfer dye-labeled primers for DNA sequencing and anaylysis", *Proc. Natl. Acad. Sci USA*, 92 4347-4351.
Khanna, P., et al, 1980, "4',5'-Dimethoxy-6-carboxyfluorescein: A Novel Dipole-Dipole Coupled Fluorescence Energy Transfer Acceptor Useful for Fluorescence Immunoassays", *Analytical Biochemistry*, 108: 156-161.
Lukhtanov, E., et al, 2001, "Fluorogenic Dna probes for multicolor hybridization assays", *American Biotechnology Laboratory*, 68-69.
Olejnik, J., et al, 1996, "Photocleavable biotin phosphoramidite for 5'-end-labeling, affinity purification and phosphorylation of synthetic oligonucleotides", *Nucleic Acids Research*, 24 (2): 631-366.
Pon, R., et al, 2004, "Linker phosphoramidite reagents for the attachment of the first nucleoside to underivatized solid-phase supports", *Nucleic Acids Research*, 32 (2): 623-631.
Phycolink, 1999, "Can Phycobiliproteins be used in Fluorescent Resonance Energy Transfer (FRET)?", www.prozyme.com/faqs/pjfretfaq.html, 1-6.
Sabbagh, G., et al, 2004, "Synthesis of phosphorothioamidites derived from 3'-thio-3'-deoxythymidine and 3'-thio-2',3'-dideoxycytidine and the automated synthesis of oligodeoxynucleotides containing a 3'- S-phosphorothiolate linkage", *Nucleic Acids Research*, 32 (2): 495-501.
Sokol, D., et al, 1998, "Real time detection of DNA-RNA hybridization in living cells", *Proc. Natl. Acad. Sci. USA*, 95 11538-11543.
Song, X, et al., 2001, "Detection of Multivalent Interactions through Two-Tiered Energy Transfer", *Analytical Biochemistry*, 291: 133-141.
Stevens, S., et al, 2002, "Comparison of Quantitative competitive PCR with Light Cycler-Based PCR for Measuring Epstein-Barr Virus DNA Load in Clinical Specimens", *Journal of Clinical Microbiology*, 40(11): 3986-3992.
Tsuji, A., et al, "Development of a Time-Resolved Fluorometric method for Observing Hybridization in Living Cells Using Fluorescence Resonance Energy Transfer", *Biophysical Journal*, 81: 501-515, 2001.

* cited by examiner

*Primary Examiner*—Kenneth R. Horlick
*Assistant Examiner*—David C Thomas
(74) *Attorney, Agent, or Firm*—Charles M. Doyle; Olga Kay

(57) ABSTRACT

The present invention relates generally to the transfer of non-fluorescent energy between donor and acceptor moieties. In certain embodiments, the invention provides biomolecules that include substantially non-fluorescent donor moieties. Processes involving these donor moieties typically entail reduced background fluorescence relative to applications that involve conventional fluorescent donor moieties. In addition to reaction mixtures and methods that include the use of these biomolecules, the invention also provides related kits and systems.

23 Claims, 59 Drawing Sheets

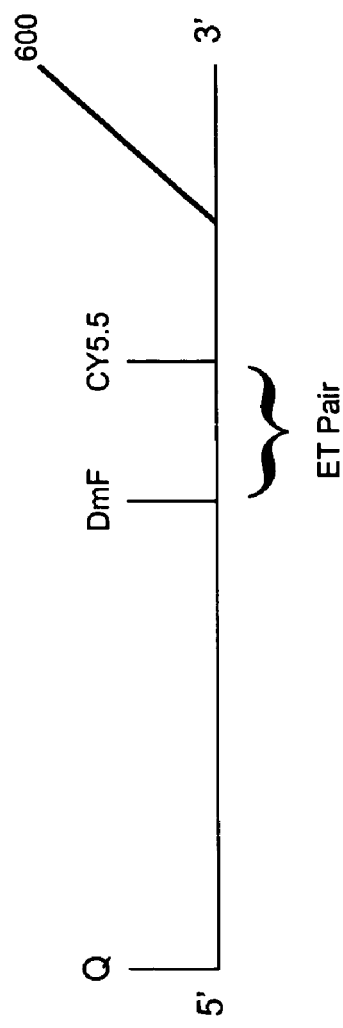
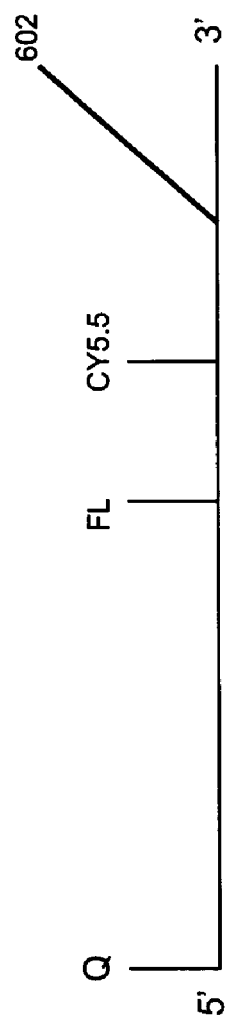
Fig. 37A
Fig. 37B

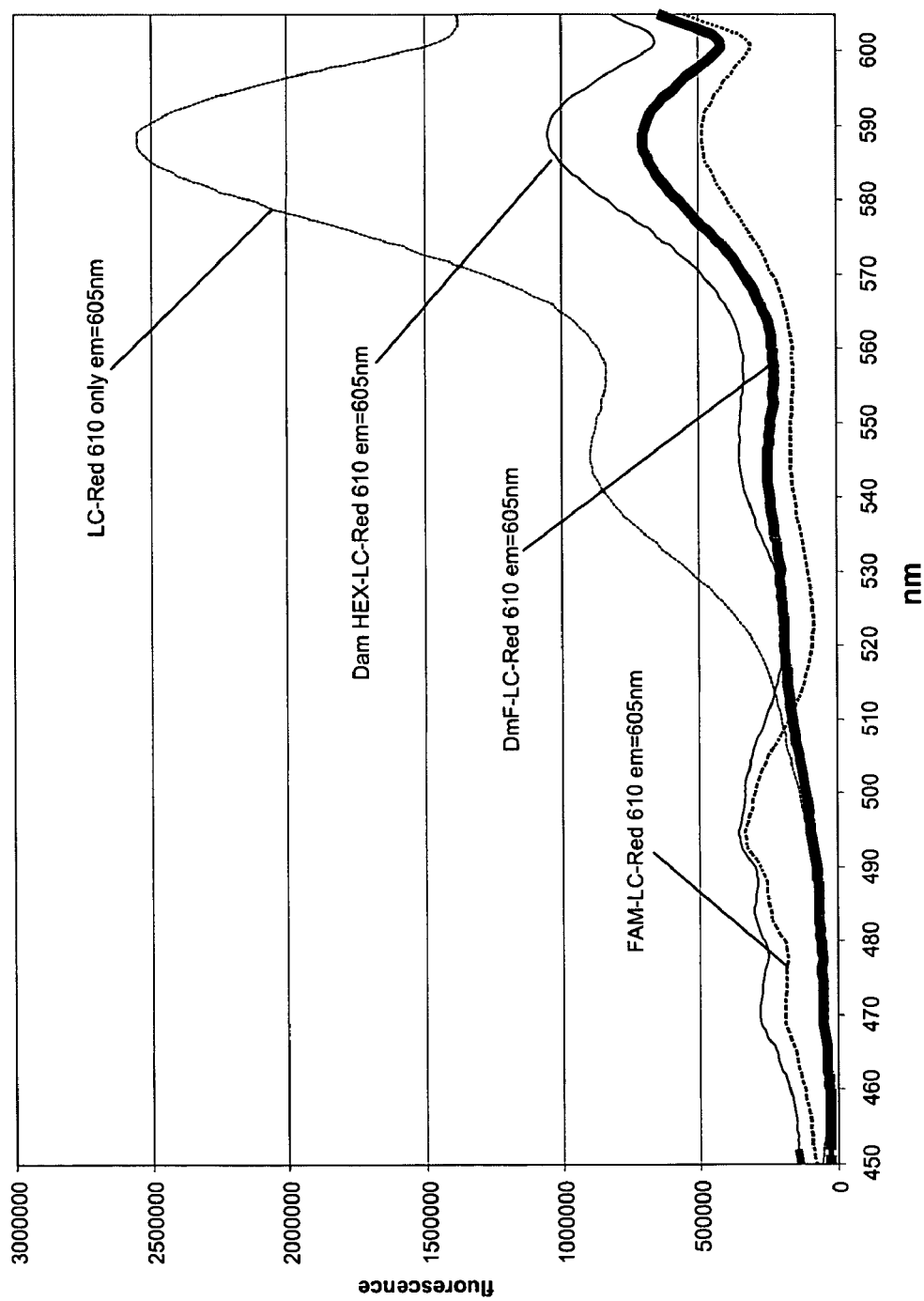

NON-FLUORESCENT ENERGY TRANSFER

CROSS-REFERENCE TO RELATED APPLICATION

This application claims priority to and benefit of U.S. Provisional Application Ser. No. 60/724,202, filed Oct. 5, 2005, the content of which is hereby incorporated by reference in its entirety for all purposes.

FIELD OF THE INVENTION

The present invention relates to the fields of molecular biology and biomolecule chemistry. In certain embodiments, reagents and assays involving non-fluorescent energy transfer are provided.

BACKGROUND OF THE INVENTION

Techniques for acquiring information about biomolecules, such as nucleic acids and proteins, are applied in many different disciplines, including various branches of medical science. Many of these techniques include the use of fluorescent labels to generate detectable signals. For example, one class of fluorescent dyes that has been developed includes energy transfer fluorescent dyes. In general, energy transfer processes involving these dyes include dipole-dipole resonance interactions between donor and acceptor moieties that are associated with the same or different biomolecules. In these processes, when donor and acceptor moieties are positioned within sufficient proximity and with proper orientations relative to one another, energy emitted from donor moieties is absorbed by acceptor moieties. Detectable signals are produced when this absorbed energy causes the acceptor moieties to fluoresce.

Exemplary approaches to nucleic acid analysis that commonly utilize energy transfer fluorescent dyes include hybridization-based assays, such as nucleic acid amplification procedures (e.g., Polymerase Chain Reaction (PCR), Strand Displacement Amplification (SDA), Nucleic Acid Sequence-Based Amplification (NASBA), and Ligase Chain Reaction (LCR)), high-density nucleic acid array-based processes, single nucleotide polymorphism (SNP) analyses, and nucleic acid sequencing techniques. To further illustrate, a number of methods for assaying other types of biomolecules that can utilize energy transfer to effect detection are also known. For example, proteins can be detected and quantified using various techniques, including SDS-polyacrylamide gel electrophoresis, capillary electrophoresis, enzyme assays, cell-based assays, and a wide range of immunological techniques, such as Western blotting and ELISA.

In addition, several diagnostic and analytical assays have been developed which involve the detection of multiple components in a sample using fluorescent dyes, including, e.g., flow cytometry (Lanier et al. (1984) "Human lymphocyte subpopulations identified by using three-color immunofluorescence and flow cytometry analysis: correlation of Leu-2, Leu-3, Leu-7, Leu-8, and Leu-11 cell surface antigen expression," *J. Immunol.* 132:151-156, which is incorporated by reference) and chromosome analysis (Gray et al. (1979) "High resolution chromosome analysis: one and two parameter flow cytometry," *Chromosoma* 73:9-27, which is incorporated by reference), along with many of the assays referred to above. For these assays, it is desirable to simultaneously employ a set of two or more spectrally resolvable fluorescent dyes so that more than one target substance can be detected in the sample at the same time. Simultaneous detection of multiple components in a sample using multiple dyes reduces the time required to serially detect individual components in a sample. In the case of multi-loci DNA probe assays, the use of multiple spectrally resolvable fluorescent dyes reduces the number of reaction tubes that are needed, thereby simplifying the experimental protocols and facilitating the manufacturing of application-specific kits. In the case of automated DNA sequencing, for example, the use of multiple spectrally resolvable fluorescent dyes allows for the analysis of all four bases in a single lane thereby increasing throughput over single-color methods and eliminating uncertainties associated with inter-lane electrophoretic mobility variations.

Multiplex PCR detection using 5' nuclease probes, molecular beacons, FRET or hybridization probes, among other multiplex detection methods, typically includes the pooling of quenched or unquenched fluorescent probes, e.g., to improve assay throughput relative to protocols that utilize single probes in a given reaction. To illustrate, multiplex assays are commonly used to detect multiple genotype markers or pathogens in samples obtained from patients as part of diagnostic procedures. In these formats, the overall baseline or background fluorescence from the pooled probes increases additively as the number of probes increases in the reaction mixture. This baseline fluorescence also increases in essentially any assay system when the amount of any single probe is increased. Baseline fluorescence generally adversely affects the performance of a given assay by, for example, reducing the detection sensitivity and dynamic range of the assay. Accordingly, baseline fluorescence effectively limits the total number of fluorescent probes and/or the amount of a given probe that can be utilized at one time in a particular assay.

SUMMARY OF THE INVENTION

The present invention provides biomolecules and other reagents related to non-fluorescent energy transfer. For example, certain biomolecules that include substantially non-fluorescent donor moieties described herein can be used to effect the detection of target biomolecules. Among the advantages of using these donor moieties for such detection is reduced background fluorescence relative to approaches that utilize fluorescent donor moieties. In addition to reaction mixtures and various methods, related kits and systems are also provided.

In some aspects, the invention provides a biomolecule comprising at least one substantially non-fluorescent donor moiety that is capable of transferring non-fluorescent energy to at least one acceptor or reporter moiety (e.g., a fluorescent dye) when the acceptor moiety is sufficiently proximal to the substantially non-fluorescent donor moiety such that the acceptor moiety emits light in response to the accepted non-fluorescent energy. The biomolecule typically comprises at least one nucleoside, at least one amino acid, at least one sugar, and/or at least one lipid. In certain embodiments, the biomolecule comprises the acceptor moiety and/or at least one quencher moiety. In some embodiments, the substantially non-fluorescent donor moiety and/or the acceptor moiety are attached to the biomolecule via at least one linker moiety.

The biomolecules described herein include many different embodiments. To illustrate, the biomolecule comprises a biopolymer synthesis reagent (e.g., a phosphoramidite) in certain embodiments. In some embodiments, the biomolecule comprises a biopolymer. In these embodiments, different monomer units of the biopolymer optionally comprise the substantially non-fluorescent donor moiety and the acceptor moiety. In certain of these embodiments, a monomer unit of the biopolymer comprises both the substantially non-fluorescent donor moiety and the acceptor moiety. Optionally, the substantially non-fluorescent donor moiety and acceptor moiety are not attached to one another via at least one linker moiety. To further illustrate, the biomolecule comprises at least one oligonucleotide or at least one polynucleotide in certain embodiments. The oligonucleotide generally comprises a primer nucleic acid or a probe nucleic acid (e.g., a hybridization probe, a 5'-nuclease probe, and a hairpin probe). In some embodiments, the biomolecule comprises at least one peptide, at least one polypeptide, at least one protein, at least one enzyme, at least one hormone, or at least one immunoglobulin.

In other aspects, the invention provides a reaction mixture that includes at least one nucleotide (e.g., an extendible nucleotide and/or a terminator nucleotide), at least one primer nucleic acid, and/or at least a first probe nucleic acid (e.g., a hybridization probe, a 5'-nuclease probe, and a hairpin probe) in which one or more of the nucleotide, the primer nucleic acid, or the first probe nucleic acid comprises at least one substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy. In some embodiments, the nucleotide, the primer nucleic acid, or the first probe nucleic acid comprises the acceptor moiety (e.g., a fluorescent dye). Optionally, the nucleotide, the primer nucleic acid, or the first probe nucleic acid comprises at least one quencher moiety. In certain embodiments, the substantially non-fluorescent donor moiety and/or the acceptor moiety are attached to the nucleotide, the primer nucleic acid, or the first probe nucleic acid via at least one linker moiety. In some embodiments, the reaction mixture also includes at least one nucleotide incorporating biocatalyst. Optionally, the substantially non-fluorescent donor moiety is attached to the nucleotide, the primer nucleic acid, or the first probe nucleic acid via at least one linker moiety. In certain embodiments, the reaction mixture includes at least a second probe nucleic acid (e.g., that is optionally used as a hybridization probe in some embodiments) that comprises the acceptor moiety. In some of these embodiments, the second probe nucleic acid further comprises at least one quencher moiety. To illustrate, this reaction mixture can be used in performing various real-time PCR monitoring protocols or nucleic acid sequencing procedures, among many other possible applications.

In other aspects, the invention provides a reaction mixture comprising at least a first biopolymer synthesis reagent that comprises at least one substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy. In some embodiments, the substantially non-fluorescent donor moiety is attached to the first biopolymer synthesis reagent via at least one linker moiety. In certain embodiments, the first biopolymer synthesis reagent comprises the acceptor moiety, which substantially non-fluorescent donor moiety and acceptor moiety are not attached to one another via at least one linker moiety. In other embodiments, the first biopolymer synthesis reagent comprises the acceptor moiety, which substantially non-fluorescent donor moiety and acceptor moiety are attached to one another via at least one linker moiety. Optionally, a solid support comprises the first biopolymer synthesis reagent. In some embodiments, the reaction mixture includes at least a second biopolymer synthesis reagent that comprises the acceptor moiety and/or at least one quencher moiety. To further illustrate, the first biopolymer synthesis reagent comprises a polypeptide synthesis reagent in certain embodiments, whereas in others, the first biopolymer synthesis reagent comprises a nucleic acid synthesis reagent (e.g., a phosphoramidite). This reaction mixture is optionally used in, e.g., the synthesis and/or labeling of biopolymers.

In other aspects, the invention provides a method of detecting a target biomolecule. The method includes (a) binding at least one probe biomolecule (e.g., an immunoglobulin) to a target biomolecule in which the probe biomolecule comprises at least one substantially non-fluorescent donor moiety and at least one acceptor moiety (e.g., a fluorescent dye), which acceptor moiety accepts non-fluorescent energy transferred from the substantially non-fluorescent donor moiety and emits light in response to the accepted non-fluorescent energy. In addition, the method also includes (b) detecting the light emitted from the acceptor moiety, thereby detecting the target biomolecule. In some embodiments, the target biomolecule comprises a target nucleic acid and the method comprises amplifying at least a subsequence of the target nucleic acid prior to and/or during (b). Typically, the probe biomolecule comprises a biopolymer. In certain embodiments, different monomer units of the biopolymer comprise the substantially non-fluorescent donor moiety and the acceptor moiety. A monomer unit of the biopolymer optionally comprises both the substantially non-fluorescent donor moiety and the acceptor moiety, which substantially non-fluorescent donor moiety and acceptor moiety are typically either attached or not attached to one another via at least one linker moiety. To further illustrate, the probe (e.g., a hybridization probe, a 5'-nuclease probe, or a hairpin probe) and/or target biomolecule comprises a nucleic acid in certain embodiments. In these embodiments, (a) generally comprises hybridizing the probe and target biomolecules.

In other aspects, the invention provides another method of detecting a target biomolecule. The method includes (a) providing at least first and second probe biomolecules in which the first probe biomolecule comprises at least one substantially non-fluorescent donor moiety and in which the second probe biomolecule comprises at least one acceptor moiety (e.g., a fluorescent dye). The method also includes (b) binding the first and second probe biomolecules to the target biomolecule such that the acceptor moiety accepts non-fluorescent energy transferred from the substantially non-fluorescent donor moiety and emits light in response to the accepted non-fluorescent energy. In addition, the method also includes (c) detecting the light emitted from the acceptor moiety, thereby detecting the target biomolecule. In some embodiments, the substantially non-fluorescent donor moiety on the first probe biomolecule is an isothiocyanate other than 4-dimethylaminophenylazophenyl-4'-isothiocyanate (DABITC). In some embodiments, the target biomolecule comprises a target nucleic acid and the method comprises amplifying at least a subsequence of the target nucleic acid prior to and/or during (c). In certain embodiments, the first and/or second probe biomolecule comprises an immunoglobulin. In some embodiments, the first probe biomolecule, the second probe biomolecule, and/or the target biomolecule comprises a nucleic acid. In these embodiments, the first and/or second probe biomolecule typically comprises a hybridization probe, a 5'-nuclease probe, or a hairpin probe. In some of these embodiments, (b) comprises hybridizing the first probe biomolecule, the second probe biomolecule, and the target biomolecule.

In other aspects, the invention provides a method of performing a proximity assay (e.g., a lipid-mixing assay). The method includes (a) providing at least first and second probe biomolecules in which the first probe biomolecule comprises at least one substantially non-fluorescent donor moiety and in which the second probe biomolecule comprises at least one acceptor moiety. The method also includes (b) positioning the first and second probe biomolecules in a first position relative to one another in which the first and second probe biomolecules are in sufficient proximity to one another in the first position such that the acceptor moiety accepts non-fluorescent energy transferred from the substantially non-fluorescent donor moiety and emits light in response to the accepted non-fluorescent energy. In addition, the method also includes (c) moving the first and second probe biomolecules to at least a second position relative to one another, and (d) monitoring the light emitted from the acceptor moiety before, after, and/or as the first and second probe biomolecules are moved to the second position, thereby performing the proximity assay. Typically, the first and/or second probe biomolecule comprises an oligonucleotide, an immunoglobulin, or a lipid.

In other aspects, the invention provides a method of extending a primer nucleic acid. The method includes incubating a target nucleic acid with (a) at least one extendible nucleotide and/or at least one terminator nucleotide, (b) at least one nucleotide incorporating biocatalyst, and (c) at least one primer nucleic acid that is at least partially complementary to at least a subsequence of the target nucleic acid under conditions whereby the nucleotide incorporating biocatalyst extends the primer nucleic acid to produce at least one extended primer nucleic acid by incorporating the extendible nucleotide and/or the terminator nucleotide at a terminal end of the extended primer nucleic acid in which the primer nucleic acid, the extendible nucleotide, and/or the terminator nucleotide comprises at least one substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy, thereby extending the primer nucleic acid. In certain embodiments, a plurality of extended primer nucleic acids are produced and the method comprises identifying terminator nucleotides in the extended primer nucleic acids, whereby at least a portion of a base sequence of the target nucleic acid is determinable from the identified terminator nucleotides. In some embodiments, the primer nucleic acid, the extendible nucleotide, and/or the terminator nucleotide comprises the acceptor moiety. In certain embodiments, the substantially non-fluorescent donor moiety and the acceptor moiety are not attached to one another via at least one linker moiety, whereas in others, the substantially non-fluorescent donor moiety and the acceptor moiety are attached to one another via at least one linker moiety.

In other aspects, the invention provides a method of producing a phosphoramidite. The method includes (a) attaching at least one substantially non-fluorescent donor moiety to a compound comprising at least one protecting group. The substantially non-fluorescent donor moiety is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy. The method also includes (b) attaching a group comprising the formula:

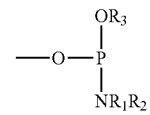

where $R_1$ and $R_2$ are alkyl groups independently selected from the group consisting of: methyl, ethyl, propyl, isopropyl, butyl, pentyl, hexyl, heptyl, octyl, nonyl, and heptyl; and $R_3$ is $(CH_2)_2CN$ or $CH_3$, thereby producing the phosphoramidite. Exemplary protecting groups are selected from, e.g., trityl, monomethoxytrityl, dimethoxytrityl, levulinyl, fluorenylmethoxycarbonyl, and benzhydryloxycarbonyl. In some embodiments, the phosphoramidite comprises the formula:

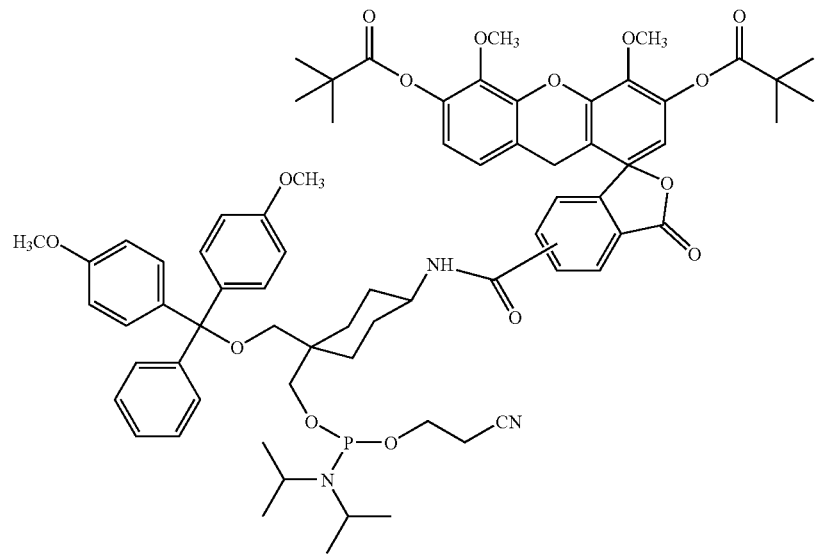

In other aspects, the invention provides a business method that includes (a) receiving an order from a customer for at least a first biomolecule comprising at least one substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy. In addition, the business method also includes (b) supplying the first biomolecule to the customer in response to the order.

In other aspects, the invention provides a kit that includes at least a first biomolecule comprising at least one substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy. In some embodiments, a solid support comprises the first biomolecule. In certain embodiments, the first biomolecule comprises the acceptor moiety. In some of these embodiments, the substantially non-fluorescent donor moiety and acceptor moiety are not attached to one another via at least one linker, whereas in others, the substantially non-fluorescent donor moiety and acceptor moiety are attached to one another via at least one linker. In certain embodiments, the kit includes a second biomolecule that comprises the acceptor moiety. Optionally, the kit includes one or more of, e.g., a buffer, a salt, a metal ion, a nucleotide incorporating biocatalyst, a pyrophosphatase, glycerol, dimethyl sulfoxide, and/or poly rA. Typically, the kit includes at least one container for packaging at least the first biomolecule.

The kits include various embodiments and can be used to perform many different applications. In some embodiments, for example, the first biomolecule comprises an immunoglobulin and the kit comprises instructions for binding the immunoglobulin to a target epitope and detecting the binding of the immunoglobulin to the target epitope. Optionally, the first biomolecule comprises a lipid and the kit comprises instructions for performing a proximity assay using the lipid. In certain embodiments, the first biomolecule comprises a primer nucleic acid and the kit comprises instructions for extending the primer nucleic acid. In some embodiments, the first biomolecule comprises an extendible nucleotide and/or a terminator nucleotide. In certain embodiments, the first biomolecule comprises a first biopolymer synthesis reagent and the kit comprises instructions for synthesizing a biopolymer using the first biopolymer synthesis reagent. In some of these embodiments, the first biopolymer synthesis reagent comprises a polypeptide synthesis reagent. Optionally, the kit includes at least a second biopolymer synthesis reagent. In some embodiments, the second biopolymer synthesis reagent comprises the acceptor moiety. In certain embodiments, the first biopolymer synthesis reagent comprises a nucleic acid synthesis reagent (e.g., a phosphoramidite). In some embodiments, the first biomolecule comprises at least a first probe nucleic acid. To illustrate, the first probe nucleic acid optionally comprises a hybridization probe, a 5'-nuclease probe, or a hairpin probe. In some of these embodiments, the kit includes at least a second probe nucleic acid that comprises the acceptor moiety. In certain embodiments, this second probe nucleic acid is used as a hybridization probe along with the first probe nucleic acid in performing various hybridization probe assays.

In other aspects, the invention provides a system that includes (a) at least one container and/or solid support comprising at least one biomolecule comprising at least one substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy. The system also includes (b) at least one radiation source that is configured to direct electromagnetic radiation at the donor moiety. In addition, the system also includes (c) at least one detection component that is configured to detect the light emitted from the acceptor moiety when the acceptor moiety is sufficiently proximal to the substantially non-fluorescent donor moiety. Typically, the system includes at least one logic device operably connected to the detection component, which logic device comprises one or more instruction sets that scale detected light emissions from the acceptor moiety. In some embodiments, the system includes (d) at least one thermal modulator that thermally communicates with the container and/or the solid support to modulate temperature proximal to the container and/or the solid support, and/or (e) at least one fluid transfer component that transfers fluid to and/or from the container and/or the solid support.

The substantially non-fluorescent donor moieties of the biomolecules, reaction mixtures, methods, kits, and systems described herein include various embodiments. In some embodiments, for example, the substantially non-fluorescent donor moiety comprises one or more of: 4',5'-dimethoxy-6-carboxyfluorescein, 4',5'-dimethoxy-5-carboxyfluorescein, 6-carboxy-aminopentachlorofluorescein, or 5-carboxy-aminopentachlorofluorescein. In certain embodiments, peak visible absorbances of the substantially non-fluorescent donor moiety and the acceptor moiety differ from one another by about 100 nm or more. Typically, a ratio of a detectable absolute fluorescent emission from a 6-carboxyfluorescein moiety to a detectable absolute fluorescent emission from the substantially non-fluorescent donor moiety at substantially identical concentrations of the 6-carboxyfluorescein moiety and the substantially non-fluorescent donor moiety is about 1000:1 or more. In certain embodiments, the substantially non-fluorescent donor moiety is a carboxyfluorescein, a stilbene-2,2'-disulfonic acid, or an isothiocyanate. In other embodiments, the substantially non-fluorescent donor moiety is an isothiocyanate other than 4-dimethylaminophenylazophenyl-4'-isothiocyanate (DABITC).

In some embodiments, the substantially non-fluorescent donor moieties and the acceptor moieties described herein are not attached to one another via linker moieties. In other embodiments, the substantially non-fluorescent donor moieties and the acceptor moieties described herein are attached to one another via linker moieties. In some of these embodiments, the linker moieties lack the structure:

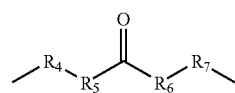

where $R_4$ is a $C_{1-5}$ alkyl attached to the substantially non-fluorescent donor moiety; $R_5$ is selected from the group consisting of: NH, S, and O; $R_6$ is selected from the group consisting of: an alkene, a diene, an alkyne, and a five or six membered ring having at least one unsaturated bond or a fused ring structure which is attached to the carbonyl carbon;

and R₇ comprises a functional group that attaches the linker moiety to the acceptor moiety.

BRIEF DESCRIPTION OF THE DRAWINGS

FIG. 37A schematically depicts a 5'-nuclease probe according to one embodiment of the invention.

FIG. 37B schematically depicts a 5'-nuclease probe that lacks a substantially non-fluorescent donor moiety.

FIG. 47A is a plot of overlaid spectra obtained from excitation scans of hybridization probe assays that involved acceptor probes labeled with LC-Red 610 and donor probes labeled with FAM, DmF, or Dam HEX.

DEFINITIONS

Figure 1:
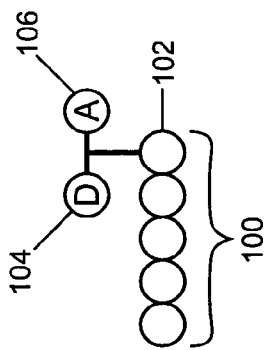
FIGS. 1A-F schematically show certain representative embodiments of some reagents of the invention.
Figure 1:
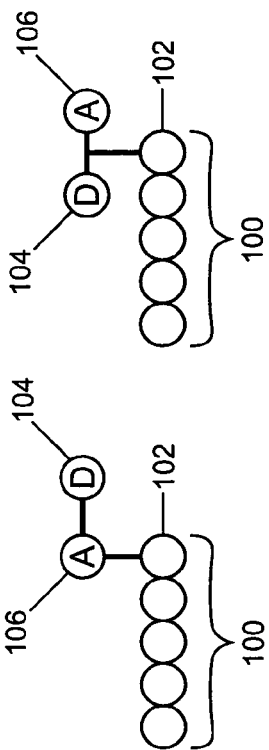
Figure 1:
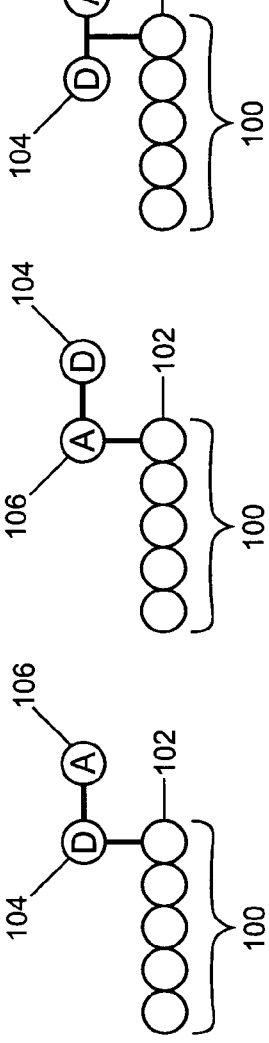
Figure 1:
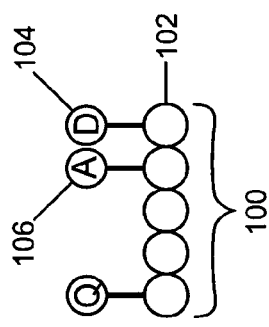
Figure 1:
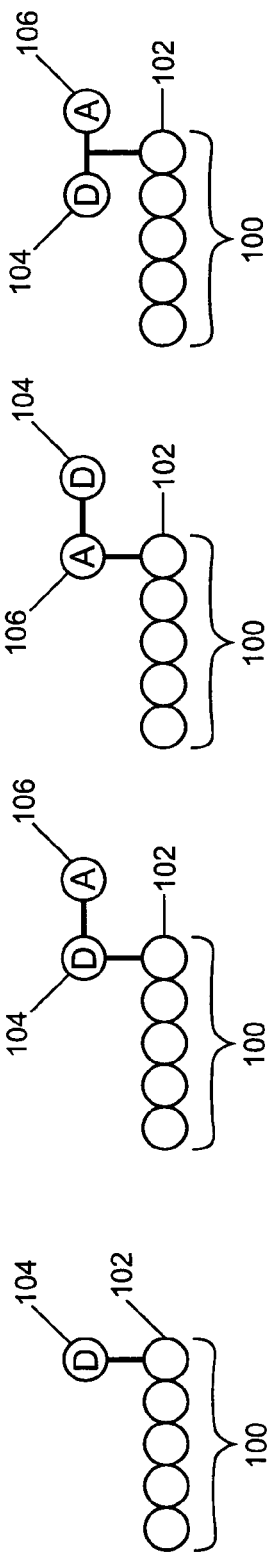
Figure 1:
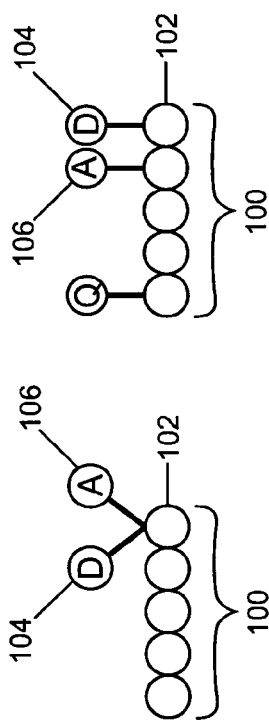

Before describing the present invention in detail, it is to be understood that this invention is not limited to particular biomolecules, methods, reaction mixtures, compositions, kits, or systems, which can vary. As used in this specification and the appended claims, the singular forms "a," "an," and "the" also include plural referents unless the context clearly provides otherwise. Thus, for example, reference to "a biomolecule" includes a combination of two or more biomolecules. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology, and grammatical variants thereof, will be used in accordance with the definitions set forth below.

A "5'-nuclease probe" refers to a labeled oligonucleotide that is capable of producing a detectable signal change upon being cleaved. To illustrate, in certain embodiments a 5'-nuclease probe comprises three labeling moieties and emits radiation of increased intensity after one of the labels is cleaved or otherwise separated from the oligonucleotide. In some of these embodiments, for example, the 5'-nuclease probe is labeled with a 5' terminus quencher moiety and a pair of acceptor and substantially non-fluorescent donor moieties proximal to the 3' terminus of the probe. In certain embodiments, 5'-nuclease probes are labeled at one or more positions other than, or in addition to, these terminal positions. When the probe is intact, energy transfer typically occurs between the labeling moieties such that the quencher moiety at least in part quenches the fluorescent emission from the acceptor moiety. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission from the acceptor moiety is no longer quenched. In other exemplary embodiments, 5'-nuclease probes include only acceptor and substantially non-fluorescent donor moieties. When the moieties of these probes are separated from one another upon cleavage, a decrease in fluorescent emission from the acceptor moiety generally occurs. To further illustrate, in certain embodiments 5'-nuclease probes include regions of self-complementarity such that the probes are capable of forming hairpin structures under selected conditions. In these embodiments, 5'-nuclease probes are also referred to herein as "hairpin probes." Exemplary 5'-nuclease probes that can be adapted for use with the substantially non-fluorescent donor moieties described herein are also described in, e.g., U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., U.S. Pat. No. 5,994,056, entitled "HOMOGENEOUS METHODS FOR NUCLEIC ACID AMPLIFICATION AND DETECTION," issued Nov. 30, 1999 to Higuchi, and U.S. Pat. No. 6,171,785, entitled "METHODS AND DEVICES FOR HEMOGENEOUS NUCLEIC ACID AMPLIFICATION AND DETECTOR," issued Jan. 9, 2001 to Higuchi, which are each incorporated by reference.

An "acceptor moiety" or "acceptor" refers to a moiety that is capable of accepting or absorbing energy transferred from an energy source. In some embodiments, acceptor moieties are also capable of emitting energy (e.g., light and/or heat) upon absorbing sufficient amounts of transferred energy. In these embodiments, acceptors are also known as "reporter moieties" or as "reporters". To illustrate, certain acceptor moieties fluoresce in response to accepting sufficient amounts of non-fluorescent energy transferred from the substantially non-fluorescent donor moieties described herein. Exemplary acceptor moieties include, but are not limited to, various fluorophores, such as LightCycler®-Red 610 (LC-Red 610), LC-Red 640, LC-Red 670, LC-Red 705, JA-270, CY5, CY5.5, among many others.

An "alkyl group" refers to a linear, branched, or cyclic saturated hydrocarbon moiety and includes all positional isomers, such as methyl, ethyl, propyl, isopropyl, butyl, pentyl, hexyl, octyl, nonyl, heptyl, 1-methylethyl, 1-methylpropyl, 2-methylpropyl, 1-methylbutyl, 2-methylbutyl, 3-methylbutyl, 2,2-dimethylpropyl, 1-ethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2, 2-trimethylpropyl, 1-ethyl-1-methylpropyl, 1-ethyl-2-methylpropyl, n-hexyl, cyclohexyl, n-heptyl, n-octyl, 2-ethylhexyl, n-nonyl, and n-decyl. An alkyl group typically comprises about 1-20 carbon atoms and more typically comprises about 2-15 carbon atoms. Alkyl groups can be substituted or unsubstituted.

An "amino acid" refers to any monomer unit that can be incorporated into a peptide, polypeptide, or protein. As used herein, the term "amino acid" includes the following twenty natural or genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The structures of these twenty natural amino acids are shown in, e.g., Stryer et al., *Biochemistry*, 5$^{th}$ ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," *Proc. Natl. Acad. Sci. U.S.A.* 101(24):8882-8887, Anderson et al. (2004) "An expanded genetic code with a functional quadruplet codon" *Proc. Natl. Acad. Sci. U.S.A.* 101(20):7566-7571, Ikeda et al. (2003) "Synthesis of a novel histidine analogue and its efficient incorporation into a protein in vivo," *Protein Eng. Des. Sel.* 16(9):699-706, Chin et al. (2003) "An Expanded Eukaryotic Genetic Code," *Science* 301(5635):964-967, James et al. (2001) "Kinetic characterization of ribonuclease S mutants containing photoisomerizable phenylazophenylalanine residues," *Protein Eng. Des. Sel.* 14(12):983-991, Kohrer et al. (2001) "Import of amber and ochre suppressor tRNAs into mammalian cells: A general approach to site-specific insertion of amino acid analogues into proteins," *Proc. Natl. Acad. Sci. U.S.A.* 98(25):14310-14315, Bacher et al. (2001) "Selection and Characterization of *Escherichia coli* Variants Capable of Growth on an Otherwise Toxic Tryptophan Analogue," *J. Bacteriol.* 183(18): 5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," *J. Biol. Chem.* 275(51):40324-40328, and Budisa et al. (2001) "Proteins with {beta}-(thienopyrrolyl)alanines as alternative chromophores and pharmaceutically active amino acids," *Protein Sci.* 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "amplifying" in the context of biomolecules refers to any process that results in an increase in the copy number of a biomolecule or set of biomolecules or subsequences thereof. As it applies to nucleic acids, amplification refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using RT-PCR is a form of amplification. Furthermore, the generation of multiple RNA molecules from a single DNA molecule during the process of transcription is also a form of amplification.

The term "attaching" or "binding" refers to a process in which two or more materials covalently and/or non-covalently associate with one another, even if only transiently. In certain embodiments, for example, substantially non-fluorescent donor moieties are attached to compounds as part of methods of producing phosphoramidites. To further illustrate, probe biomolecules bind to target biomolecules to effect the detection of those targets in some of the processes described herein.

A "biomolecule" refers to an organic molecule that is made and/or used by an organism, and/or that is utilized to analyze the organism or components thereof. Exemplary biomolecules include nucleic acids, nucleotides, amino acids, polypeptides, peptides, peptide fragments, sugars, fatty acids, steroids, lipids, and combinations of these biomolecules (e.g., glycoproteins, ribonucleoproteins, or lipoproteins).

A "biopolymer" refers a biomolecule that includes at least two monomer units attached to one another.

A "biopolymer synthesis reagent" refers a compound that can be used to synthesize a biopolymer or a component thereof. To illustrate, in certain embodiments biopolymer synthesis reagents are "nucleic acid synthesis reagents", such as phosphoramidites or other reagents, which can be used to synthesize oligonucleotides or other nucleic acids. Exemplary oligonucleotide synthesis techniques that are optionally utilized include the phosphoryl chloridate method (Michelson et al. (1955) *J. Chem. Soc.* 2632, which is incorporated by reference), the phosphodiester coupling method (Khorana et al. (1956) *Chem. & Ind. London* 1523, which is incorporated by reference), the phosphotriester method (Letsinger et al. (1969) *J. Am. Chem. Soc.* 91(12):3360-3365, which is incorporated by reference), the phosphite-triester method (Letsinger et al. (1975) *J. Am. Chem. Soc.* 97:3278-3279 and Letsinger et al. (1976) *J. Am. Chem. Soc.* 98:3655-3661, which are both incorporated by reference), and the phosphoramidite method (Beaucage et al. (1981) *Tetrahedron Lett.* 22:1859-1862 and McBride et al. (1983) *Tetrahedron Lett.* 24:245-248, which are both incorporated by reference). To further illustrate, biopolymer synthesis reagents also include "polypeptide synthesis reagents" (e.g., t-Boc/Fmoc reagents), which can be used to synthesize peptides or other proteins. See, e.g., Chan et al. (Eds.), *Fmoc Solid Phase Peptide Synthesis: A Practical Approach*, Oxford University Press (2000) and Jones, *Amino Acid and Peptide Synthesis*, Oxford University Press (2002), which are both incorporated by reference. Biopolymers can also be synthesized using many other approaches known to those of skill in the art, such as by chemical ligation (see, e.g., Hackeng et al. (1999) "Protein synthesis by native chemical ligation: Expanded scope by using straightforward methodology" *PNAS* 96(18):10068-10073, which is incorporated by reference).

A "complement" in the context of nucleic acids refers to a nucleic acid, or a segment thereof, that can combine in an antiparallel association or hybridize with at least a subsequence of a nucleic acid. The antiparallel association can be intramolecular, e.g., in the form of a hairpin loop within a nucleic acid, or intermolecular, such as when two or more single-stranded nucleic acids hybridize with one another. Certain bases not commonly found in natural nucleic acids may be included in the nucleic acids referred to herein and include, for example, hypoxanthine, 7-deazaguanine, among many others. Complementarity need not be perfect; stable duplexes or triplexes, for example, may contain mismatched base pairs or unmatched bases. That is, antiparallel associations, whether intramolecular or intermolecular, can occur under certain conditions when nucleic acids are only "partially complementary". Those skilled in the art of nucleic acid chemistry can determine, e.g., duplex or triplex stability by empirically considering a number of variables, such as the length of a region of complementarity, base composition and sequence in a region of complementarity, ionic strength, melting temperature ($T_m$), and incidence of mismatched base pairs.

An "epitope" refers a site on an antigen that is recognized and bound by an immunoglobulin or a T-cell receptor.

An "extendible nucleotide" refers to a nucleotide to which at least one other nucleotide can be added or covalently bonded, e.g., in a reaction catalyzed by a nucleotide incorporating biocatalyst once the extendible nucleotide is incorporated into a nucleotide polymer. Examples of extendible nucleotides include deoxyribonucleotides and ribonucleotides. An extendible nucleotide is typically extended by adding another nucleotide at a 3'-position of the sugar moiety of the extendible nucleotide.

The term "extending" in the context of nucleic acids refers a process in which one or more nucleotides are added to, or otherwise incorporated into, a given nucleic acid.

An "extended primer nucleic acid" refers to a primer nucleic acid to which one or more additional nucleotides have been added or otherwise incorporated (e.g., covalently bonded to).

A "fluorescent dye" refers to a compound that is capable of absorbing energy from an energy source and emitting light in response to that absorbed energy. In some embodiments, certain fluorescent dyes function as acceptor moieties in the biomolecules described herein.

A "hairpin probe" refers to an oligonucleotide that can be used to effect target nucleic acid detection and that includes at least one region of self-complementarity such that the probe is capable of forming a hairpin or loop structure under selected conditions. Typically, hairpin probes include one or more labeling moieties. In one exemplary embodiment, acceptor moieties and substantially non-fluorescent donor moieties are positioned relative to one another in the hairpin probes such that energy transfer between these moieties can occur substantially only when the probe is in a hairpin confirmation. In other embodiments, hairpin probes include quencher moieties in addition to acceptor moieties and substantially non-fluorescent donor moieties. In some of these embodiments, these moieties are positioned in the probes such that the quencher moieties at least partially quench otherwise detectable signals that result from energy transfer between the acceptor and substantially non-fluorescent donor moieties when the probes are in hairpin confirmations. In contrast, when the probes in these embodiments are not in hairpin confirmations, signals that result from energy transfer between the acceptor and substantially non-fluorescent donor moieties are generally detectable. Accordingly, hairpin probes function similar to molecular beacons in some of these embodiments. Hairpin probes can also function as 5'-nuclease probes or hybridization probes in certain embodiments.

A "hormone" refers to a biomolecule produced by an organism that generates a specific effect on the organism at a site other than the biomolecule's point of origin in the organism. Hormones are typically produced by the endocrine systems of multi-cellular organisms and generally exert stimulatory or inhibitory effects on cellular activity. Hormones can also be synthesized ex vivo.

A "hybridization probe" refers an oligonucleotide that includes at least one labeling moiety that can be used to effect target nucleic acid detection. In some embodiments, hybridization probes function in pairs. In some of these embodiments, for example, a first hybridization probe of a pair includes at least one substantially non-fluorescent donor moiety at or proximal to its 3'-end, while the second hybridization probe of the pair includes at least one acceptor moiety (e.g., LC-Red 610, LC-Red 640, LC-Red 670, LC-Red 705, JA-270, CY5, or CY5.5) at or proximal to its 5'-end. The probes are typically designed such that when both probes hybridize with a target or template nucleic acid (e.g., during a PCR), the first hybridization probe binds to the 5'-end side or upstream from the second hybridization probe and within sufficient proximity for energy transfer to occur between the substantially non-fluorescent donor and acceptor moieties to thereby produce a detectable signal. Typically, the second hybridization probe also includes a phosphate or other group on its 3'-end to prevent extension of the probe during a PCR. In certain embodiments, a hybridization probe pair includes the substantially non-fluorescent donor moiety at or proximal to the 5'-end of one probe and the acceptor moiety at or proximal to the 3'-end of the other probe. In another exemplary embodiment, one hybridization probe of a pair includes at least one substantially non-fluorescent donor moiety and at least one acceptor moiety, while the other probe of the pair comprises at least one quencher moiety. In this embodiment, the moieties are positioned on the probes such that the quencher moiety quenches fluorescence emitted from the acceptor moiety when both probes are hybridized to a target nucleic acid.

Nucleic acids "hybridize" or "anneal" in a base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotides is typically base specific, e.g., A/T and G/C, by Watson/Crick and/or Hoogsteen-type interactions. It is not a requirement that two polynucleotides have 100% complementarity over their full length to achieve hybridization. In some aspects, a hybridization complex can form from intermolecular interactions, or alternatively, can form from intramolecular interactions. Hybridization occurs due to a variety of well-characterized forces, including hydrogen bonding, solvent exclusion, and base stacking. An extensive guide to nucleic hybridization may be found in Tijssen, *Laboratory Techniques in Biochemistry and Molecular Biology-Hybridization with Nucleic Acid Probes*, part I, chapter 2, "Overview of principles of hybridization and the strategy of nucleic acid probe assays," Elsevier (1993).

An "immunoglobulin" or "antibody" refers to a polypeptide substantially encoded by at least one immunoglobulin gene or fragments of at least one immunoglobulin gene that can participate in specific binding with a ligand. The term includes naturally occurring forms, as well as fragments and derivatives. Fragments within the scope of the term as used herein include those produced by digestion with various peptidases, such as Fab, Fab' and F(ab)'2 fragments, those produced by chemical dissociation, by chemical cleavage, and recombinantly or otherwise artificially evolved, so long as the fragment remains capable of specific binding to a target molecule. Typical recombinant fragments, as are produced, e.g., by phage display, include single chain Fab and scFv ("single chain variable region") fragments. Derivatives within the scope of the term include antibodies (or fragments thereof) that have been modified in sequence, but remain capable of specific binding to a target molecule, including interspecies chimeric and humanized antibodies. As used herein, antibodies or immunoglobulins can be produced by any known technique, including harvest from cell culture of native B-lymphocytes, hybridomas, recombinant expression systems, or phage display.

A "linker moiety" or "linker" refers to a chemical moiety that covalently or non-covalently (e.g., ionically) attaches a compound, substituent group, or other moiety to, e.g., a solid support, another compound, group, or moiety. For example, a linker optionally attaches a label (e.g., substantially non-fluorescent donor moiety, an acceptor moiety) to a biomolecule. Linkers are typically bifunctional chemical moieties and in certain embodiments, they comprise cleavable attachments, which can be cleaved by, e.g., heat, an enzyme, a chemical agent, and/or electromagnetic radiation to release materials or compounds from, e.g., a solid support or another compound. A careful choice of linker allows cleavage to be performed under appropriate conditions compatible with the stability of the compound and assay method. Generally a linker has no specific biological activity other than to, e.g., join chemical moieties (e.g., substantially non-fluorescent donor and acceptor moieties) together or to preserve some minimum distance or other spatial relationship between such moieties. However, the constituents of a linker may be selected to influence some property of the linked chemical moieties such as three-dimensional conformation, net charge, and/or hydrophobicity. Additional description of linker molecules is provided in, e.g., Lyttle et al. (1996) *Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, Pljevaljcic et al. (2003) *J. Am. Chem. Soc.* 125(12):3486, Ward, et. al., U.S. Pat. No. 4,711,955, Stavrianopoulos, U.S. Pat. No. 4,707,352, and Stavrianopoulos, U.S. Pat. No. 4,707,440, which are each incorporated by reference.

A "lipid" refers to a water-insoluble biomolecule that comprises a fatty acid, a sterol, and/or an isoprenoid compound. Exemplary lipid groups include fatty acids (e.g., oleic acid, palmitic acid, and stearic acid), neutral fats (e.g., coconut oil and beef tallow), phospholipids (e.g., phosphatidylethanolamine, phosphatidylcholine, phosphatidylserine, and phosphatidylinositol), sphingolipids (e.g., sphingomyelin), glycolipids (e.g., cerebrosides and gangliosides), steroids (e.g., cholesterol), and terpenes (e.g., essential oils and carotenoids). Lipids are also described in, e.g., Vance et al., *Biochemistry of Lipids, Lipoproteins and Membranes*, $4^{th}$ Ed., Elsevier Science (2002), which is incorporated by reference.

A "lipid-mixing assay" refers an assay that involves detecting one or more properties of lipids upon combining or pooling the lipids together with one another. To illustrate, some of these assays involve fusing membranes that comprise labeling moieties, such as the substantially non-fluorescent donor, acceptor, and/or quencher moieties described herein. Lipid-mixing assays are also described in, e.g., Blumenthal et al. (2002) "Fluorescent lipid probes in the study of viral membrane fusion," *Chem Phys Lipids* 116:39-55, Hoekstra et al. (1993) "Lipid mixing assays to determine fusion in liposome systems," *Methods Enzymol* 220:15-32, Hoekstra (1990) "Fluorescence assays to monitor membrane fusion: potential application in biliary lipid secretion and vesicle interactions," *Hepatology* 12:61S-66S, Stegmann et al. (1989) "Protein-mediated membrane fusion," *Annu Rev Biophys Biophys Chem* 18:187-211, Hoekstra et al. (1984) "Fluorescence method for measuring the kinetics of fusion between biological membranes," *Biochemistry* 23:5675-5681, Struck et al. (1981) "Use of resonance energy transfer to monitor membrane fusion," *Biochemistry* 20:4093-4099, and Stegmann et al. (1993) "Evaluation of viral membrane fusion assays. Comparison of the octadecylrhodamine dequenching assay with the pyrene excimer assay," *Biochemistry* 32:11330-11337, which are each incorporated by reference.

A "monomer unit" or "monomer" refers a chemical compound that can undergo polymerization. Exemplary monomer units include nucleotides, which can be polymerized to form a nucleic acid, amino acids, which can be polymerized to form proteins, and monosaccharides, which can be polymerized to form polysaccharides.

A "mixture" refers to a combination of two or more different components. A "reaction mixture" refers a mixture that comprises molecules that can participate in and/or facilitate a given reaction or assay. To illustrate, an amplification reaction mixture generally includes a solution containing reagents necessary to carry out an amplification reaction, and typically contains primers, a nucleotide incorporating biocatalyst, dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components, which includes the biomolecules of the invention.

A "moiety" or "group" refers to one of the portions into which something, such as a molecule, is divided (e.g., a functional group or a substituent group). For example, a biomolecule of the invention includes at least one substantially non-fluorescent donor moiety.

The term "monitoring" in the context of a given process, reaction, or assay refers to the periodic or continuous observation, detection, testing, and/or quantification of one or more aspects or properties of the process, reaction, or assay, or component thereof. To illustrate, in certain PCR-based assays, the intensity of light emitted from acceptor moieties is periodically or continuously detected during the reaction cycles. A monitoring process is typically at least partially automated.

A "non-fluorescent donor moiety" refers a moiety that is capable of transferring, emitting, or donating one or more forms of excitation energy to one or more acceptor moieties, but not energy in the form of detectable fluorescence. A "substantially non-fluorescent donor moiety" refers a moiety that is capable of transferring, emitting, or donating one or more forms of excitation energy to one or more acceptor moieties, approximately or essentially without emitting detectable fluorescence from the donor. For example, a ratio of a detectable absolute fluorescent emission from a fluorescent moiety to a detectable absolute fluorescent emission from a substantially non-fluorescent donor moiety at approximately the same concentrations of the fluorescent moiety and the substantially non-fluorescent donor moiety is typically about 500:1 or more, more typically about 1000:1 or more, and even more typically about 1500:1 or more (e.g., about 2000:1, about 2500:1, about 3000:1, about 3500:1, about 4000:1, about 4500:1, or about 5000:1). Exemplary substantially non-fluorescent donor moieties, include 4',5'-dimethoxy-6-carboxyfluorescein, 4',5'-dimethoxy-5-carboxyfluorescein, 6-carboxy-aminopentachlorofluorescein, and 5-carboxy-aminopentachlorofluorescein. Non-fluorescent donor moieties and substantially non-fluorescent donor moieties typically emit non-fluorescent excitation energy in response to absorbing sufficient amounts of energy from another energy source (e.g., a light source and/or a heat source). In addition, acceptor moieties are generally capable of absorbing the excitation energy emitted by these donor moieties and fluorescing in response.

The term "non-fluorescent energy" refers energy other than in the form of emitted fluorescence.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as modified forms thereof, peptide nucleic acids (PNAs), and locked nucleic acids (LNA™s). In certain embodiments, a nucleic acid can be a polymer that includes multiple monomer types, e.g., both RNA and DNA subunits. A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

Nucleic acids are not limited to molecules having naturally occurring polynucleotide sequences or structures, naturally occurring backbones, and/or naturally occurring internucleotide linkages. For example, nucleic acids containing one or more carbocyclic sugars are also included within this definition (Jenkins et al. (1995) Chem. Soc. Rev. pp 169-176, which is incorporated by reference). To further illustrate, although a nucleic acid will generally contain phosphodiester bonds, in some cases nucleic acid analogs are included that have alternate backbones. These include, without limitation, phosphoramide (Beaucage et al. (1993) Tetrahedron 49(10): 1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110:4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Briu et al. (1989) J. Am. Chem. Soc. 111:2321), O-methylphophoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207), which references are each incorporated by reference. Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which are each incorporated by reference. Several nucleic acid analogs are also described in, e.g., Rawls, C & E News Jun. 2, 1997 page 35, which is incorporated by reference. Modifications of the ribose-phosphate backbone may be done to facilitate the addition of additional moieties, such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases. To illustrate, certain bases used in nucleotides that act as melting temperature ($T_m$) modifiers are optionally included. For example, some of these include 7-deazapurines (e.g., 7-deazaguanine or 7-deazaadenine), pyrazolo[3,4-d]pyrimidines, and propynyl-dN (e.g., propynyl-dU or propynyl-dC). See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, xanthine; 8-aza derivatives of 2-aminopurine, 2,6-diaminopurine, 2-amino-6-chloropurine, hypoxanthine, and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; and 5-propynyluracil. Many non-naturally occurring bases are also described in, e.g., Seela et al. (1991) Helv. Chim. Acta 74:1790, Grein et al. (1994) Bioorg. Med. Chem. Lett. 4:971-

976, and Seela et al. (1999) *Helv. Chim. Acta* 82:1640, which are each incorporated by reference.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

A "nucleoside" refers to a nucleic acid component that comprises a base or basic group (e.g., comprising at least one homocyclic ring, at least one heterocyclic ring, and/or at least one aryl group) covalently linked to a sugar moiety (e.g., a ribose sugar), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, or a propynyl-dN base). Exemplary nucleosides include ribonucleosides, deoxyribonucleosides, dideoxyribonucleosides, and carbocyclic nucleosides.

A "nucleotide" refers to an ester of a nucleoside, e.g., a phosphate ester of a nucleoside. To illustrate, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification. Exemplary nucleotide incorporating enzymes include, e.g., polymerases, terminal transferases, reverse transcriptases, telomerases, polynucleotide phosphorylases, and ligases. A "thermostable enzyme" refers to an enzyme that is stable to heat, is heat resistant, and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids and at temperatures, which allow primer hybridization. Heating conditions necessary for nucleic acid denaturation are well known to persons skilled in the art and are exemplified in U.S. Pat. No. 4,683,202, entitled "PROCESS FOR AMPLIFYING NUCLEIC ACID SEQUENCES," issued Jul. 28, 1987 to Mullis and U.S. Pat. No. 4,683,195, entitled "PROCESS FOR AMPLIFYING, DETECTING, AND/OR CLONING NUCLEIC ACID SEQUENCES," issued Jul. 28, 1987 to Mullis et al., which are both incorporated by reference. To further illustrate, a "thermostable polymerase" refers to an enzyme that is suitable for use in a temperature cycling reaction, such as a polymerase chain reaction ("PCR"). For a thermostable polymerase, enzymatic activity refers to the catalysis of the combination of the nucleotides in the proper manner to form primer extension products that are complementary to a template nucleic acid.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and methyl phosphonate, including associated counterions, e.g., $H^+$, $NH_4^+$, and $Na^+$, if such counterions are present. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

The term "peak visible absorbance" refers to a wavelength at which a molecule absorbs energy in the visible or optical region of the electromagnetic spectrum most efficiently. The visible or optical region of the electromagnetic spectrum typically includes wavelengths that range from approximately 700 nanometers (nm) to approximately 400 nm. In some embodiments, for example, non-fluorescent energy transfer from a substantially non-fluorescent donor moiety to an acceptor moiety is most efficient when the peak visible absorbances of the substantially non-fluorescent donor moiety and the acceptor moiety differ from one another by about 100 nm or more. Depending on the particular molecule under consideration, peak visible absorbance may correspond to a global absorbance maximum for the molecule or to a local absorbance maximum for the molecule in the visible region of the electromagnetic spectrum.

A "phosphoramidite" refers to a compound that includes a group comprising the formula:

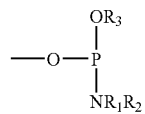

where $R_1$ and $R_2$ are alkyl groups independently selected from the group consisting of: methyl, ethyl, propyl, isopropyl, butyl, pentyl, hexyl, heptyl, octyl, nonyl, and heptyl; and $R_3$ is ($CH_2$)$_2$CN or $CH_3$. In certain embodiments, for example, a phosphoramidite is a nucleoside-3'-phosphoramidite monomer, commonly used in oligonucleotide synthesis procedures. In some of these embodiments, these phosphoramidite monomers are protected at the 5' hydroxyl position with a protecting group. Different protecting groups are also typically attached to the exocyclic amines of the bases. In addition, the phosphorous atom of the monomer is optionally protected with beta-cyanoethyl ($R_3$) and diisopropylamine ($NR_1R_2$) groups or other groups that are consistent with the formula shown above. Phosphoramidites and oligonucleotide synthesis are also described in, e.g., Beaucage et al. (1992) "Advances in the synthesis of oligonucleotides by the phosphoramidite approach," *Tetrahedron* 48:2223-2311, which is incorporated by reference.

The terms "polypeptide", "peptide", and "protein" are used interchangeably herein to refer to a polymer of amino acids. The terms apply to amino acid polymers in which one or more amino acid residues are analogs, derivatives or mimetics of corresponding naturally occurring amino acids, as well as to naturally occurring amino acid polymers. For example, polypeptides can be modified or derivatized, e.g., by the addition of carbohydrate residues to form glycoproteins, by the addition of lipid moieties to form lipoproteins. Accordingly, the terms "polypeptide", "peptide", and "protein" include glycoproteins and lipoproteins, as well as non-glycoproteins and non-lipoproteins.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide). Although other primer nucleic acid lengths are optionally utilized, they typically comprise hybridizing regions that range from about 8 to about 100 nucleotides in length. Short primer nucleic acids generally require cooler temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid can be labeled, if desired, by incorporating a label detectable by, e.g., spectroscopic, photochemical, biochemical, immunochemical, chemical, or other techniques. To illustrate, useful labels include substantially non-fluorescent donor moieties, acceptor moieties, quencher moieties, radioisotopes, electron-dense reagents, enzymes (as commonly used in performing ELISAs), biotin, or haptens and proteins for which antisera or monoclonal antibodies are available. Many of these and other labels are described further herein and/or are otherwise known in the art. One of skill in the art will recognize that, in certain embodiments, primer nucleic acids can also be used as probe nucleic acids.

A "probe biomolecule" refers to a labeled or unlabeled biomolecule that is capable of selectively binding to a target biomolecule.

A "protecting group" refers to a chemical group that is covalently or non-covalently attached to a given compound and which prevents undesired chemical reactions from occurring at one or more sites in the compound. Exemplary protecting groups include trityl, monomethoxytrityl, dimethoxytrityl, levulinyl, fluorenylmethoxycarbonyl, and benzhydryloxycarbonyl.

The term "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition, such as, but not limited to, a stringent hybridization condition. A hybridization assay carried out using a probe under sufficiently stringent hybridization conditions permits the selective detection of a specific target sequence. The term "hybridizing region" refers to that region of a nucleic acid that is exactly or substantially complementary to, and therefore capable of hybridizing to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support. A probe of the invention is generally included in a nucleic acid that comprises one or more labels (e.g., substantially non-fluorescent donor moieties, acceptor moieties, and/or quencher moieties), such as a 5'-nuclease probe, a hybridization probe, a fluorescent resonance energy transfer (FRET) probe, a hairpin probe, or a molecular beacon, which can also be utilized to detect hybridization between the probe and target nucleic acids in a sample. In some embodiments, the hybridizing region of the probe is completely complementary to the target sequence. However, in general, complete complementarity is not necessary (i.e., nucleic acids can be partially complementary to one another); stable hybridization complexes may contain mismatched bases or unmatched bases. Modification of the stringent conditions may be necessary to permit a stable hybridization complex with one or more base pair mismatches or unmatched bases. Sambrook et al., *Molecular Cloning: A Laboratory Manual,* 3rd Ed., Cold Spring Harbor Laboratory Press, Cold Spring Harbor, N.Y. (2001), which is incorporated by reference, provides guidance for suitable modification. Stability of the target/probe hybridization complex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

The term "proximity assay" refers to an assay in which the production of a detectable signal depends at least in part on acceptor and donor moieties being within sufficient proximity to one another. In certain embodiments, for example, separate biomolecules comprise acceptor and donor moieties such that the production of detectable energy emissions from the acceptor moieties depends at least in part on the intermolecular distance between the biomolecules. In other exemplary embodiments, biomolecules comprise both acceptor and donor moieties (e.g., attached to the same or different monomer units of a biopolymer) and the generation of detectable energy emissions from the acceptor moieties depends at least in part on the intramolecular spacing between these moieties. In some of these embodiments, detectable energy emissions from the acceptor moieties vary, e.g., as the biomolecules undergo conformational changes, or as acceptor and donor moieties are separated from one another in the biomolecules via enzymatic or other cleavage processes.

A "quencher moiety" or "quencher" refers to a moiety that is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Certain quenchers may re-emit the energy absorbed from, e.g., a fluorescent dye in a signal characteristic for that quencher and thus, a quencher can also be an acceptor moiety. This phenomenon is generally known as fluorescent resonance energy transfer or FRET. Alternatively, a quencher may dissipate the energy absorbed from a fluorescent dye in a form other than light, such as heat. Molecules commonly used in FRET applications include, for example, fluorescein, FAM, JOE, rhodamine, R6G, TAMRA, ROX, DABCYL, and EDANS. Whether a fluorescent dye is an acceptor or a quencher is defined by its excitation and emission spectra, and the fluorescent dye with which it is paired. For example, FAM is most efficiently excited by light with a wavelength of 494 nm, and emits light with a spectrum of 500 to 650 nm, and an emission maximum of 525 nm. FAM is a suitable donor moiety for use with, e.g., TAMRA as a quencher, which has at its excitation maximum 560 nm. Exemplary non-fluorescent or dark quenchers that dissipate energy absorbed from a fluorescent dye include the Black Hole Quenchers™ marketed by Biosearch Technologies, Inc. (Novato, Calif., USA). The Black Hole Quenchers™ are structures comprising at least three radicals selected from substituted or unsubstituted aryl or heteroaryl compounds, or combinations thereof, in which at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Exemplary quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

A "sequence" of a biopolymer refers to the order and identity of monomer units (e.g., nucleotides, amino acids, and monosaccharides) in the biopolymer. The sequence of a nucleic acid is typically read in the 5' to 3' direction, whereas the sequence of a polypeptide is generally read in a direction from the amino- or N-terminus to the carboxyl- or C-terminus of the molecule.

A "solid support" refers to a solid material that can be derivatized with, or otherwise attached to, a chemical moiety, such as a probe. Exemplary solid supports include plates, beads, microbeads, controlled pore glass (CPG), polystyrene, tubes, fibers, whiskers, combs, hybridization chips (including microarray substrates, such as those used in GeneChip® probe arrays (Affymetrix, Inc., Santa Clara, Calif., USA)), membranes, single crystals, ceramic layers, self-assembling monolayers, and metal surfaces.

The terms "stringent" or "stringent conditions", as used herein, denote hybridization conditions of low ionic strength and high temperature, as is well known in the art. See, e.g., Sambrook et al., *Molecular Cloning: A Laboratory Manual*, 3$^{rd}$ Ed., Cold Spring Harbor Laboratory Press, Cold Spring Harbor, N.Y. (2001); *Current Protocols in Molecular Biology* (Ausubel et al., ed., J. Wiley & Sons Inc., New York, 1997 and supplemented through Supplement No. 75, August 2006); Tijssen (1993), supra, each of which is incorporated by reference. Generally, stringent conditions are selected to be about 5-30° C. lower than the thermal melting point ($T_m$) for the specified sequence at a defined ionic strength and pH. Alternatively, stringent conditions are selected to be about 5-15° C. lower than the $T_m$ for the specified sequence at a defined ionic strength and pH. The $T_m$ is the temperature (under defined ionic strength, pH and nucleic acid concentration) at which 50% of the probes complementary to the target are hybridized to the target sequence at equilibrium (as the target sequences are present in excess, at $T_m$, 50% of the probes are hybridized at equilibrium).

A "subsequence", "segment", or "fragment" refers to any portion of an entire biopolymer sequence.

The term "sufficiently proximal" in the context of energy transfer between donor and acceptor moieties refers to a suitable spacing and/or positioning of those moieties relative to one another such that the acceptor moieties are capable of accepting or absorbing energy transferred from the donor moieties. To illustrate, certain acceptor moieties fluoresce in response to accepting sufficient amounts non-fluorescent energy transferred from suitably spaced and/or positioned substantially non-fluorescent donor moieties.

A "sugar" or "carbohydrate" refers to a polyhydroxy-aldehyde (aldose) or polyhydroxy-ketone (ketose), or compounds or analogs derived therefrom. Carbohydrate polymers (e.g., oligosaccharides and polysaccharides) include monosaccharide monomer units. Exemplary carbohydrates include glyceraldehyde, erthyrose, threose, ribose, arabinose, xylose, lyxose, allose, altrose, glucose, mannose, gulose, idose, galactose, talose, dihydroxyacetone, xylulose, and fructose. Sugar analogs, such as carbocyclic sugars are also included within the definition of sugar (see, e.g., Jenkins et al. (1995) *Chem. Soc. Rev.* pp 169-176, which is incorporated by reference).

A "system" refers a group of objects and/or devices that form a network for performing a desired objective. In some embodiments, for example, a system of the invention includes a container and/or solid support that includes one or more biomolecules comprising substantially non-fluorescent donor moieties and detection components that are configured to detect light emitted from acceptor moieties when the acceptor moieties are sufficiently proximal to the substantially non-fluorescent donor moieties, e.g., as part of hybridization probe assays.

A "target" refers to a biomolecule, or portion thereof, that is to be amplified, detected, and/or otherwise analyzed.

A "terminator nucleotide" refers to a nucleotide, which upon incorporation into a nucleic acid prevents further extension of the nucleic acid, e.g., by at least one nucleotide incorporating biocatalyst.

Objects "thermally communicate" with one another when thermal energy is transferred or is capable of being transferred between the objects. In certain embodiments of the systems described herein, for example, thermal modulators thermally communicate with containers and/or solid supports to modulate temperature in the containers and/or on the solid supports.

DETAILED DESCRIPTION OF THE INVENTION

The present invention relates generally to the transfer of non-fluorescent energy between donor moieties and acceptor moieties. More specifically, the substantially non-fluorescent donor moieties described herein can be used in essentially any application involving energy transfer between donor and acceptor moieties, including many different proximity assay formats. Conventional energy transfer dye pairs, for example, are typically set up with a short wavelength fluorescent donor moiety that transmits absorbed energy to a longer wavelength acceptor moiety. Further, it is generally thought that the fluorescence emission spectrum of the donor moiety and the fluorescence absorbance spectrum of the acceptor moiety must overlap. Contrary to this conventional teaching, one surprising result of the present invention is that the donor moieties described herein lack appreciable fluorescence emission spectra. Nonetheless, when acceptor moieties are positioned sufficiently proximal to these donor moieties, the acceptor moieties emit light in response to absorbing non-fluorescent energy transferred from the donor moieties.

A common problem associated with using conventional fluorescent donor moieties, such as fluorescein, is background fluorescence emitted by the donor moieties themselves. This background fluorescence can make it difficult to discern the energy transfer to the longer wavelength acceptor moieties, particularly in multiplex applications that include the use of multiple fluorescent donor probes. In particular, background or baseline light emissions such as these typically negatively impact the performance of assays involving these probes by, e.g., limiting the sensitivity (i.e., the ability of the assay to discriminate between small differences in analyte concentration) and dynamic range (i.e., the useful range of the assay which extends from the lowest concentration at which quantitative measurements can be made (limit of quantitation, or LOQ) to the concentration at which the calibration curve departs from linearity (limit of linearity, LOL)) of detection. Accordingly, among the advantages of using the substantially non-fluorescent donor moieties described herein is the reduction or elimination of this type of background fluorescence, thereby improving the performance of assays involving these types of donor moieties. The improved signal-to-noise ratios provided by the donor moieties described herein are further illustrated, along with many other features of the invention, in the examples provided below.

As described in greater detail below, the invention provides biomolecules (e.g., biopolymer synthesis reagents, oligonucleotides, polypeptides, carbohydrates, and lipids) that include the substantially non-fluorescent donor moieties described herein covalently or otherwise associated therewith. The invention also provides various reaction mixtures that include these biomolecules along with other reagents for performing a given process, such as biopolymer synthesis, biopolymer labeling, nucleic acid detection, among many others described herein or otherwise known to those of skill in the art. As also described herein, various methods are also provided. In certain embodiments, for example, the invention provides methods of performing proximity assays and methods of detecting target biomolecules. To illustrate, the biomolecules described herein are optionally used in methods to detect nucleic acids in various applications, including genotyping, diagnostics, forensics, among many others well known to those of skill in the art. To further illustrate, methods of sequencing and/or labeling biopolymers are also provided, as are methods for synthesizing the biomolecules described herein. The invention further provides certain business methods. Moreover, the invention also provides assorted kits and systems. These and a variety of other aspects and features of the present invention will be apparent upon a complete review of this disclosure.

Substantially Non-Fluorescent Donor Moieties

Essentially any compound that is capable of transferring non-fluorescent energy to an acceptor moiety, without emitting appreciable fluorescence in the process, can be used as a substantially non-fluorescent donor moiety. Accordingly, no attempt is made herein to list all of the possible compounds that are optionally utilized for this purpose. Nonetheless, certain specific substantially non-fluorescent donor moieties are referred to herein to further illustrate aspects of the present invention. In particular, representative substantially non-fluorescent donor moieties, or precursors thereof, include 4',5'-dimethoxy-6-carboxyfluorescein, 4',5'-dimethoxy-5-carboxyfluorescein, 6-carboxy-2',4,4',5',7,7'-hexachlorofluorescein, 6-carboxy-aminopentachlorofluorescein, 5-carboxy-2',4,4',5',7,7'-hexachlorofluorescein, and 5-carboxy-aminopentachlorofluorescein. The chemical structures of some of these exemplary moieties are depicted in Table I.

TABLE I

| Name | Structure |
|---|---|
| 4',5'-dimethoxy-6-carboxyfluorescein | 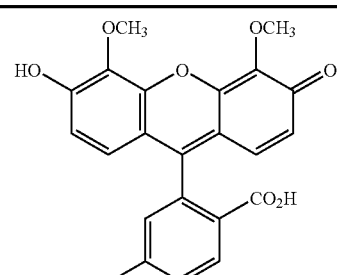 |
| 4',5'-dimethoxy-5-carboxyfluorescein | 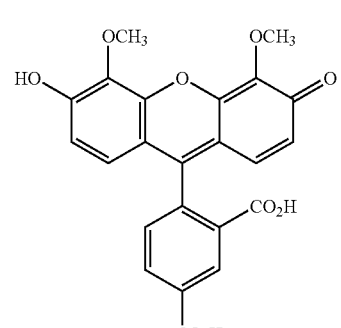 |

TABLE I-continued

| Name | Structure |
|---|---|
| 6-carboxy-2',4,4',5',7,7'-hexachlorofluorescein | (structure) |
| 5-carboxy-2',4,4',5',7,7'-hexachlorofluorescein | (structure) |

Note, that under certain conditions (e.g., when HEX labeled oligonucleotides are heated in ammonia at 55° C. for about 24 hours) the attachment of 6-carboxy-2',4,4',5',7,7'-hexachlorofluorescein and 5-carboxy-2',4,4',5',7,7'-hexachlorofluorescein to biomolecules is accompanied by the loss of at least one chlorine ion and the addition of at least one amino group and accordingly, these moieties are referred to herein as "6-carboxy-aminopentachlorofluorescein" and "5-carboxy-aminopentachlorofluorescein", respectively, or as "damaged HEX" or "Dam HEX" (e.g., 5-Dam HEX or 6-Dam HEX) when attached to biomolecules in these embodiments. Further, with regard to all of the molecular structures provided herein, it is intended that these molecular structures encompass not only the exact electronic structures presented, but also include all resonant structures and protonation states thereof.

Many substantially non-fluorescent donor moieties can be readily synthesized using chemistry that is known to persons of skill in the art. Various synthetic techniques that are optionally adapted for use in these synthetic protocols are generally known to persons skilled in the art and are also described in, e.g., March, *Advanced Organic Chemistry: Reactions, Mechanisms, and Structure*, $5^{th}$ Ed., John Wiley & Sons, Inc. (2000), Carey and Sundberg, *Advanced Organic Chemistry, Part A: Structure and Mechanism*, $4^{th}$ Ed., Plenum Publishing Corporation (2000), and Carey and Sundberg, *Advanced Organic Chemistry, Part B: Reaction and Synthesis*, $4^{th}$ Ed., Plenum Publishing Corporation (2001), which are each incorporated by reference. Chemical starting materials and other reaction components useful in the synthesis of substantially non-fluorescent donor moieties are readily available from various commercial suppliers including, e.g., Sigma-Aldrich, Inc. (St Louis, Mo., USA). Moreover, certain substantially non-fluorescent donor moieties are available pre-synthesized from various commercial suppliers, such as Molecular Probes, Inc. (Eugene, Oreg., USA).

Reagents Including Substantially Non-Fluorescent Donor Moieties

The present invention also relates to reagents that include the substantially non-fluorescent donor moieties described herein. These reagents may include any molecule or material to which these donor moieties can be covalently or non-covalently attached. Examples of these molecules and materials include, but are not limited to, solid supports (e.g., membranes or controlled pore glass), viral particles, tissues, cells (e.g., mammalian cells and bacteria or other microorganisms), organelles, and organic and inorganic monomers or polymers. In certain embodiments, for example, the reagents of the invention include biomolecules, such as lipids, nucleotides, nucleosides, amino acids, and sugars. In some embodiments, these biomolecules include biopolymers, such as peptides, proteins, polypeptides, enzymes, certain hormones, immunoglobulins, polysaccharides, oligosaccharides, polynucleotides, or oligonucleotides.

The reagents of the invention can be used in many different processes. Representative uses for nucleotide and nucleoside reagents, for example, include, but are not limited to, labeling oligonucleotides formed by enzymatic synthesis, e.g., nucleoside triphosphates used in the context of PCR amplification, nick translation reactions, and Sanger-type oligonucleotide sequencing. In certain embodiments, for example, these reagents are labeled nucleosides (NTP), such as cytosine, adenosine, guanosine, and thymidine, labeled with a substantially non-fluorescent donor moiety of the present invention. These reagents may be used in various methods involving oligonucleotide synthesis. These reagents are also labeled nucleotides, e.g., mono-, di- and triphosphate nucleoside phosphate esters in some embodiments. More specifically, these reagents include, e.g., deoxynucleoside triphosphates (dNTP), such as deoxyadenosine triphosphate, deoxycytosine triphosphate, deoxythymidine triphosphate, and deoxyguanosine triphosphate, labeled with a donor moiety as described herein. These reagents may be used, for example, as polymerase substrates in the preparation of dye labeled oligonucleotides. These reagents also include labeled dideoxynucleoside triphosphates (ddNTP) (e.g., dideoxyadenosine triphosphate, dideoxyguanosine triphosphate, dideoxycytosine triphosphate, and dideoxythymidine triphosphate) or other terminator nucleotides labeled with a substantially non-fluorescent donor moiety of the present invention. These reagents may be used, for example, in dye termination sequencing. Examples of uses for oligonucleotide reagents include, but are not limited to, as nucleic acid sequencing primers, PCR primers, hybridization probes, hairpin probes, and 5'-nuclease probes. Representative uses for polypeptides labeled with the substantially non-fluorescent donor moieties described herein include protein structural and conformational studies, receptor/ligand binding assays, and immunoassays. Examples of uses for lipid reagents labeled with the donor moieties described herein include lipid distribution and transport assays, membrane fusion assays, and membrane potential sensing analyses. In addition, exemplary uses for carbohydrate reagents labeled with the substantially non-fluorescent donor moieties described herein include receptor/ligand binding assays and structural analyses. Methods of using the reagents of the present invention are described further below.

In certain embodiments, a reagent of the invention includes one or more acceptor and/or quencher moieties in addition to one or more substantially non-fluorescent donor moieties. In other embodiments, a given reagent lacks the acceptor and/or quencher moieties. To further illustrate, FIGS. 1A-F schematically show representative embodiments of the reagents of the invention. More specifically, in each of FIGS. 1A-F biopolymer 100 is schematically illustrated with monomer units 102. As shown in the embodiment schematically depicted in FIG. 1A, biopolymer 100 includes substantially non-fluorescent donor moiety (D) 104 attached to monomer unit 102. In FIG. 1B, acceptor moiety (A) 106 is attached to monomer unit 102 of biopolymer 100 via substantially non-fluorescent donor moiety (D) 104, whereas in FIG. 1C, substantially non-fluorescent donor moiety (D) 104 is attached to monomer unit 102 of biopolymer 100 via acceptor moiety (A) 106. FIG. 1D shows another attachment of substantially non-fluorescent donor moiety (D) 104 and acceptor moiety (A) 106 to biopolymer 100. FIG. 1E schematically shows substantially non-fluorescent donor moiety (D) 104 and acceptor moiety (A) 106 separately attached to the same monomer unit 102. In addition, FIG. 1F schematically shows substantially non-fluorescent donor moiety (D) 104, acceptor moiety (A) 106, and quencher moiety (Q) 108 separately attached to different monomer units 102 of biopolymer 100. It will be appreciated that donor, acceptor, and quencher moieties are optionally covalently or non-covalently attached to reagents and/or to one another. In certain embodiments, for example, these moieties are attached to one another and/or to other components of reagents via linker moieties, whereas in other embodiments, they are not attached to one another or to other reagent components via linker moieties. It will also be appreciated that donor, acceptor, and quencher moieties can be attached to polymers via backbones or any other structural components of the molecules.

Acceptor and Quencher Moieties

The acceptor moieties of the reagents of the invention generally capable of absorbing excitation energy transferred from substantially non-fluorescent donor moieties and fluorescing in response. In some embodiments, peak visible absorbances of substantially non-fluorescent donor moieties and acceptor moieties differ from one another by about 100 nm or more. Representative general classes of acceptor moieties that may be used include, but are not limited to, xanthene dyes, cyanine dyes, phthalocyanine dyes, and squaraine dyes. Examples of acceptor moieties that are in these classes of dyes are also described in, e.g., U.S. Pat. No. 5,800,996, entitled "ENERGY TRANSFER DYES WITH ENHANCED FLUORESCENCE," issued Sep. 1, 1998 to Lee et al., which is incorporated by reference.

To further illustrate, more specific examples of acceptor moieties that may be used in certain embodiments of the reagents of the invention include, but are not limited to isomers of carboxyfluorescein (e.g., 5 and 6 carboxy), 4,7-dichlorofluoresceins, 4,7-dichlororhodamines (U.S. Pat. No. 5,847,162, entitled "4,7-DICHLORORHODAMINE DYES" issued Dec. 8, 1998 to Lee et al., which is incorporated herein by reference), fluoresceins, asymmetric benzoxanthene dyes, isomers of carboxy-HEX (e.g., 5 and 6 carboxy), NAN, CI-FLAN, TET, JOE, VIC, ZOE, rhodamine, isomers of carboxyrhodamine (e.g., 5 and 6 carboxy), isomers of carboxy R110 (e.g., 5 and 6 carboxy), isomers of carboxy R6G (e.g., 5 and 6 carboxy), isomers of N,N,N',N'-tetramethyl carboxyrhodamine (TAMRA) (e.g., 5 and 6 carboxy), isomers of carboxy-X-rhodamine (ROX) (e.g., 5 and 6 carboxy), LC-Red 610, LC-Red 640, LC-Red 670, LC-Red 705, JA-270, CY3, CY3.5, CY5, CY5.5, BODIPY® dyes (e.g., FL, 530/550, TR, and TMR), ALEXA FLUOR® dyes (e.g., 488, 532, 546, 568, 594, 555, 653, 647, 660, and 680), other energy transfer dyes (e.g., BIGDYE™ v 1 dyes, BIGDYE™ v 2 dyes, and BIGDYE™ v 3 dyes), Lucifer dyes (e.g., Lucifer yellow), CASCADE BLUE®, and Oregon Green. Additional examples of suitable acceptor moieties are provided in, e.g., Haugland, *Molecular Probes Handbook of Fluorescent Probes and Research Products*, 9$^{th}$ Ed. (2003) and the updates thereto, which are each incorporated by reference. Acceptor moieties are generally readily available from various commercial suppliers including, e.g., Molecular Probes, Inc. (Eugene, Oreg., USA), Amersham Biosciences Corp. (Piscataway, N.J., USA), and Applied Biosystems (Foster City, Calif., USA).

The substantially non-fluorescent donor moieties and the acceptor moieties are not attached to one another via linker moieties in certain embodiments. In other embodiments, these moieties are attached to one another via linker moieties. In some of these embodiments, for example, the linker moieties lack the structure:

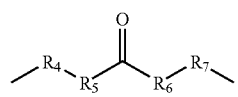

where $R_4$ is a $C_{1-5}$ alkyl attached to the substantially non-fluorescent donor moiety, $R_5$ is selected from the group consisting of: NH, S, and O, $R_6$ is selected from the group consisting of: an alkene, a diene, an alkyne, and a five or six membered ring having at least one unsaturated bond or a fused ring structure which is attached to the carbonyl carbon, and $R_7$ comprises a functional group that attaches the linker moiety to the acceptor moiety. Linker moieties are described further below.

In some embodiments, the reagents of the invention also include one or more quencher moieties. The question of whether a given fluorescent dye is a reporter or a quencher is generally defined by its excitation and emission spectra, and the fluorescent dye with which it is paired. Fluorescent molecules commonly used as quencher moieties include, but are not limited to, e.g., fluorescein, FAM, JOE, rhodamine, R6G, TAMRA, ROX, DABCYL, and EDANS. Many of these compounds are available from the commercial suppliers referred to above. Exemplary non-fluorescent or dark quenchers that dissipate energy absorbed from a fluorescent dye include the Black Hole Quenchers™ or BHQ™, which are commercially available from Biosearch Technologies, Inc. (Novato, Calif., USA).

In certain embodiments, the reagents of the invention may also include other labeling moieties. Examples of other labels include, but are not limited to, e.g., biotin, weakly fluorescent labels (Yin et al. (2003) *Appl Environ Microbiol.* 69(7):3938, Babendure et al. (2003) *Anal. Biochem.* 317(1): 1, and Jankowiak et al. (2003) *Chem Res Toxicol.* 16(3):304), radioactive labels, non-fluorescent labels, colorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Pat. Appl. No. 60/428,484, entitled "DETECTABLE LABELED NUCLEOSIDE ANALOGS AND METHODS OF USE THEREOF," filed on Nov. 22, 2002 by Bodepudi et al., which references are each incorporated by reference.

Linker Moieties

A large variety of linker moieties are available for linking other moieties (e.g., substantially non-fluorescent donor moieties, acceptor moieties, and quencher moieties) to the biomolecules and other reagents of the invention and will be apparent to one of skill in the art. A linker moiety is generally of a structure that is sterically and electronically suitable for attachment to a given biomolecule. To illustrate, linker moieties optionally include, e.g., ether, thioether, carboxamide, sulfonamide, urea, urethane, hydrazine, or other moieties. To further illustrate, linker moieties generally include between about one and about 25 nonhydrogen atoms selected from, e.g., C, N, O, P, Si, and S, and comprise essentially any combination of, e.g., ether, thioether, amine, ester, carboxamide, sulfonamide, hydrazide bonds and aromatic or heteroaromatic bonds. In some embodiments, for example, a linker moiety comprises a combination of single carbon-carbon bonds and carboxamide or thioether bonds. Although longer linear segments of linkers are optionally utilized, linear segments typically contain between about three to about 15 nonhydrogen atoms. Certain of these exemplary types of linkers are described further below.

To further illustrate, nonlimiting examples of linker moieties include substituted (e.g., functionalized) or unsubstituted groups. More specifically, exemplary linkers include imidazole/biotin linkers, polymethylene groups, arylene groups, alkylarylene groups, arylenealkyl groups, arylthio groups, amido alkyl groups, alkynyl alkyl groups, alkenyl alkyl groups, alkyl groups, alkoxyl groups, thio groups, amino alkyl groups, morpholine derivatized phosphates, peptide nucleic acids (e.g., N-(2-aminoethyl)glycine), and disulfide groups. In some embodiments, a linker moiety is isothiocyanate, sulfonyl chloride, 4,6-dichlorotriazinylamine, succinimidyl ester, or another active carboxylate when the complementary functionality or site of attachment to the biomolecule is an amine. Optionally, the linker moiety is maleimide, halo acetyl, or iodoacetamide when the complementary functionality is sulfhydryl. In certain embodiments, the linker moiety is an activated N-hydroxysuccinimide (NHS) ester formed from a carboxyl group on the donor, acceptor, or quencher moiety that can be reacted with an aminohexyl of the particular biomolecule. Certain of these and other linkers are described further in, e.g., U.S. Pat. No. 6,339,392 to Haugland et al., U.S. Pat. No. 5,047,519 to Hobbs, Jr. et al., U.S. Pat. No. 4,711,958 to Iizuka et al., U.S. Pat. No. 5,175,269 to Stavrianopoulos, U.S. Pat. No. 4,711,955 to Ward et al., U.S. Pat. No. 5,241,060 to Engelhardt et al., U.S. Pat. No. 5,328,824 to Ward et al., and U.S. Pat. Publication No. 2002/0151711 by Khan et al., which are each incorporated by reference. Additional details relating to biomolecule labeling and linker moieties are provided in, e.g., Hermanson, *Bioconjugate Techniques*, Elsevier Science (1996) and Haugland, *Molecular Probes Handbook of Fluorescent Probes and Research Products*, 9$^{th}$ Ed. (2003) and the updates thereto, which are each incorporated by reference.

In certain embodiments, suitable linkers comprise photocleavable moieties, such as 2-nitrobenzyl moieties, alpha-substituted 2-nitrobenzyl moieties (e.g., 1-(2-nitrophenyl) ethyl moieties), 3,5-dimethoxybenzyl moieties, thiohydroxamic acid, 7-nitroindoline moieties, 9-phenylxanthyl moieties, benzoin moieties, hydroxyphenacyl moieties, and NHS-ASA moieties. Photocleavable linkers are described further in, e.g., U.S. Pat. Publication No. 2003/0099972 by Olejnik et al., which is incorporated by reference. In some embodiments, linkers include metals, such as platinum atoms. These are described further in, e.g., U.S. Pat. No. 5,714,327 to Houthoff et al., which is incorporated by reference. A number of linkers of varying lengths are commercially available from various suppliers including, e.g., Operon Biotechnologies, Inc. (Huntsville, Ala., USA), BD Biosciences Clontech (Palo Alto, Calif., USA), and Molecular BioSciences (Boulder, Colo., USA).

In the context of nucleosides, nucleotides, and nucleic acids, substantially non-fluorescent donor moieties, acceptor moieties, and quencher moieties are optionally attached, e.g., to a homocyclic ring, a heterocyclic ring, or an aryl group of a nucleoside or nucleotide (e.g., via $C^5$ of a pyrimidine, $N^4$ of cytidine, $N^7$ of a purine, $N^6$ of adenosine, $C^8$ of a purine, or another attachment site known in the art), e.g., through an amide, ester, thioester, ether, thioether, carbon-carbon, or other type of covalent bond. In addition, or alternatively, the particular moiety is attached to a sugar moiety (e.g., a ribose sugar), or an analog thereof (e.g., a carbocyclic ring), of a nucleoside or nucleotide, and/or a phosphate group of a nucleotide, such as by a covalent bond that is an amide, ester, thioester, ether, thioether, carbon-carbon, or other bond. Covalent bonds are typically formed in reactions between electrophilic and nucleophilic groups of the moieties and nucleoside or nucleotides. In certain embodiments, substantially non-fluorescent donor moieties, acceptor moieties, and quencher moieties and nucleotides are directly conjugated to one another (e.g., via single, double, triple or aromatic carbon-carbon bonds, or via carbon-nitrogen bonds, nitrogen-nitrogen bonds, carbon-oxygen bonds, carbon-sulfur bonds, phosphorous-oxygen bonds, and phosphorous-nitrogen bonds).

In some embodiments, linker moieties are acetylenic amido or alkenic amido linkages, the linkage between the substantially non-fluorescent donor moiety, the acceptor moiety, or the quencher moiety and the nucleotide base is formed by reacting an activated NHS ester of the particular moiety with an alkynylamino-, alkynylethoxyamino- or alkenylamino-derivatized base of a nucleotide. Resulting linkages can include, e.g., propargyl-1-ethoxyamido(3-(amino) ethoxy-1-propynyl), 3-(carboxy)amino-1-propynyl, or 3-amino-1-propyn-1-yl.

To further illustrate, the synthesis of alkynylamino-derivatized nucleosides is also described in, e.g., Hobbs (1989) "Palladium-catalyzed synthesis of alkynylamino nucleosides. A universal linker for nucleic acids," *J. Org. Chem.* 54:3420-3422, which is incorporated by reference. In brief, the alkynylamino-derivatized nucleotides are formed by placing the appropriate halodideoxynucleoside (usually 5-iodopyrimidine and 7-iodo-7-deazapurine dideoxynucleosides) and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodideoxynucleoside. When an unprotected alkynylamine is used, the alkynylaminonucleoside can be isolated by concentrating the reaction mixture and chromatographing on silica gel using an eluting solvent that contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates can be obtained by using standard techniques known to those of skill in the art.

Biomolecule Preparation

The biomolecules or other reagents of the invention can be prepared using any suitable method, including being synthetically produced or obtained from natural sources (e.g., prior to labeling). For example, the synthesis of oligonucleotides labeled with substantially non-fluorescent donor moieties, acceptor moieties, and/or quencher moieties can be accomplished using any of a large number of known oligonucleotide labeling techniques. To illustrate, labeled oligonucleotides may be synthesized enzymatically, e.g., using a DNA polymerase or ligase, or by chemical synthesis, e.g., using a phosphoramidite method or a phosphite-triester method (Herdewijn, *Oligonucleotide Synthesis: Methods and Applications*, Humana Press (2005), Gait (Ed.), *Oligonucleotide Synthesis*, Oxford University Press (1984), Vorbruggen et al., *Handbook of Nucleoside Synthesis*, John Wiley & Sons, Inc. (2001), and Hermanson, *Bioconjugate Techniques*, Elsevier Science (1996), which are each incorporated by reference). Labels can be introduced during enzymatic synthesis utilizing, e.g., labeled nucleoside triphosphate monomers, or introduced during chemical synthesis using labeled non-nucleotide or nucleotide phosphoramidites, or may be introduced subsequent to synthesis. Approaches to synthesizing phosphoramidites that include substantially non-fluorescent donor moieties are also illustrated in the examples provided below.

An exemplary procedure for enzymatically synthesizing labeled oligonucleotides includes denaturing a template or target nucleic acid and annealing a primer to the template. A mixture of deoxynucleoside triphosphates (e.g., dGTP, dATP, dCTP, and dTTP) is typically added to the reaction mixture in which at least a fraction of one of the deoxynucleotides is labeled with a substantially non-fluorescent donor moiety, an acceptor moiety, and/or a quencher moiety as described herein. Next, a nucleotide incorporating catalyst, such as a polymerase enzyme is generally added to the reaction mixture under conditions where the enzyme is active. A labeled oligonucleotide is formed by the incorporation of the labeled deoxynucleotides during polymerase strand synthesis. In an alternative enzymatic synthesis method, two primers are used instead of one, one primer complementary to a portion of one strand and the other complementary to a portion of the other strand of a target double-stranded nucleic acid. The polymerase utilized in this method is generally thermostable, and the reaction temperature is typically cycled between denaturation and extension temperatures to effect the synthesis of labeled complementary strands of the target nucleic acid by PCR (Edwards et al. (Eds.), *Real-Time PCR: An Essential Guide*, Horizon Scientific Press (2004), Innis et al. (Eds.), *PCR Strategies*, Elsevier Science & Technology Books (1995), and Innis et al. (Eds.), *PCR Protocols*, Academic Press (1990), which are each incorporated by reference).

Labeled oligonucleotides made using chemical synthesis are generally produced using a phosphoramidite method, although other approaches are also optionally utilized. Phosphoramidite-based synthesis is commonly performed with growing oligonucleotide chains attached to solid supports, so that excess reagents, which are in the liquid phase, can be easily removed by filtration. This eliminates the need for other purification steps between cycles.

To briefly describe an exemplary solid-phase oligonucleotide synthesis cycle that utilizes a phosphoramidite method, a solid support including a protected nucleotide monomer is typically initially treated with acid (e.g., trichloroacetic acid) to remove a 5'-hydroxyl protecting group, freeing the hydroxyl for a subsequent coupling reaction. An activated intermediate is then generally formed by simultaneously adding a protected phosphoramidite nucleoside monomer and a weak acid (e.g., tetrazole) to the reaction. The weak acid protonates the nitrogen of the phosphoramidite forming a reactive intermediate. Nucleoside addition to the growing nucleic acid chain is generally completed within 30 seconds. Thereafter, a capping step is typically performed to terminate any oligonucleotide chains that did not undergo nucleoside addition. Capping can be performed with, e.g., acetic anhydride and 1-methylimidazole. The internucleotide linkage is then converted from the phosphite to the more stable phosphotriester by oxidation using, e.g., iodine as an oxidizing agent and water as the oxygen donor. Following oxidation, the hydroxyl protecting group is typically removed with a protic acid (e.g., trichloroacetic acid or dichloroacetic acid) and the cycle is repeated until chain elongation is complete. After synthesis, the synthesized oligonucleotide is generally cleaved from the solid support using a base, such as ammonium hydroxide, or t-butyl amine. The cleavage reaction also removes any phosphate protecting groups (e.g., cyanoethyl). Finally, protecting groups on exocyclic amines of the bases and hydroxyl protecting groups on the labeling moiety or moieties are removed by treating the oligonucleotide solution under basic conditions at an elevated temperature (e.g., up to about 55° C.).

Descriptions of the chemistry used to form oligonucleotides by phosphoramidite methods are also provided in, e.g., U.S. Pat. No. 4,458,066, entitled "PROCESS FOR PREPARING POLYNUCLEOTIDES," issued Jul. 3, 1984 to Caruthers et al., and U.S. Pat. No. 4,415,732, entitled "PHOSPHORAMIDITE COMPOUNDS AND PROCESSES," issued Nov. 15, 1983 to Caruthers et al., which are both incorporated by reference.

Any of the phosphoramidite nucleoside monomers may be labeled with the substantially non-fluorescent donor moieties, acceptor moieties, and/or quencher moieties described herein. In certain embodiments, if the 5'-terminus of the oligonucleotide is to be labeled, a labeled non-nucleotidic phosphoramidite may be used during the final condensation step. If an internal position of the oligonucleotide is to be labeled, a labeled nucleotidic phosphoramidite can be used during any of the condensation steps. In addition, following synthesis, oligonucleotides can also be labeled at essentially a number of positions (Eckstein et al. (Eds.), *Oligonucleotides and Analogues: A Practical Approach*, Oxford University Press (1992), Chu et al. (1983) "Derivatization of unprotected polynucleotides," *Nucleic Acids Res.* 11(18): 6513-6529, and U.S. Pat. No. 5,118,800, entitled "Oligonucleotides possessing a primary amino group in the terminal nucleotide," issued Jun. 2, 1992 to Smith et al., which is incorporated by reference. To further illustrate, oligonucleotides may also be labeled on their phosphodiester backbone (Eckstein et al. (1992), supra) or at the 3'-terminus (Nelson et al. (1992) "Oligonucleotide labeling methods. 3. Direct labeling of oligonucleotides employing a novel, non-nucleosidic, 2-aminobutyl-1,3-propanediol backbone," *Nucleic Acids Res.* 20(23):6253-6259, U.S. Pat. No. 5,401,837, entitled "Method for labeling the 3' terminus of a synthetic oligonucleotide using a unique multifunctional controlled pore glass (MF-CPG) reagent in solid phase oligonucleotide synthesis," issued Mar. 28, 1995 to Nelson, and U.S. Pat. No. 5,141,813, entitled "Multifunctional controlled pore glass reagent for solid phase oligonucleotide synthesis," issued Aug. 25, 1992 to Nelson, which are each incorporated by reference.

In certain embodiments, modified nucleotides are included in labeled oligonucleotides described herein (e.g., probes or primers). To illustrate, the introduction of modified nucleotide substitutions into oligonucleotide sequences can, e.g., increase the melting temperature of the oligonucleotides. In some embodiments, this can yield greater sensitivity relative to corresponding unmodified oligonucleotides even in the presence of one or more mismatches in sequence between the target nucleic acid and the particular oligonucleotide. Exemplary modified nucleotides that can be substituted or added in oligonucleotides include, e.g., C5-ethyl-dC, C5-methyl-dC, C5-ethyl-dU, 2,6-diaminopurines, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-O-methyl Ribo-U, 2'-O-methyl Ribo-C, an 8-aza-dA, an 8-aza-dG, a 7-deaza-dA, a 7-deaza-dG, N4-ethyl-dC, and N6-methyl-dA. To further illustrate, other examples of modified oligonucleotides include those having one or more LNA™ monomers. Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbæk, D K). Additional oligonucleotide modifications are referred to herein, including in the definitions provided above.

To further illustrate, essentially any nucleic acid (and virtually any labeled nucleic acid, whether standard or nonstandard) can be custom or standard ordered from any of a variety of commercial sources, such as The Midland Certified Reagent Company, Inc. (Midland, Tex., USA), Operon Biotechnologies, Inc. (Huntsville, Ala., USA), Proligo LLC (Boulder, Colo., USA), and many others.

The reagents of the invention can also include proteins and peptides that are labeled with substantially non-fluorescent donor moieties, acceptor moieties, and/or quencher moieties as described herein. Peptides are optionally synthesized and/or labeled using any known technique. For example, methods of preparing peptides with C-terminal alcohols typically involve either solution-phase synthesis, or solid-phase peptide synthesis. Solid-phase procedures generally utilize a covalent attachment of the starting material to a solid support (e.g., polystyrene or polyethylene glycol) through suitable linker moieties, which are generally known to those of skill in the art. The C-terminal anchoring strategy for peptide synthesis based on benzyl and benzhydrylamine linkers for Boc/Bzl (tert-butoxycarbonyl/benzyl) chemistry as well as the more labile alkoxybenzyl or 2,4-dimethoxybenzhydrylamine versions used in Fmoc/tBu (fluorenylmethoxycarbonyl/tert-butyl) protocols are optionally applied to the synthesis of peptides with either free carboxyl or carboxyl amide termini. Various aspects of peptide synthesis are also described in, e.g., Merrifield (1963) *J. Am. Chem. Soc.* 85:2149, Larsen et al. (1993) *J. Am. Chem. Soc.* 115:6247, Smith et al. (1994) *J. Peptide Protein Res.* 44:183, O'Donnell et al. (1996) *J. Am. Chem. Soc.* 118:6070, Mitchell et. al. (1976) *J. Am. Chem. Soc.* 98:7357-7362, Matsueda et. al. (1981) *Peptides* 2:45-50, Wang (1972) *J. Am. Chem. Soc.* 95:1328-1333, Rink (1987) *Tet. Let.* 28:3787-3790, Lloyd-Williams et al., *Chemical Approaches to the Synthesis of Peptides and Proteins*, CRC Press (1997), Jones, *Amino Acid and Peptide Synthesis*, $2^{nd}$ Ed., Oxford University Press (2002), and Howl, *Peptide Synthesis and Applications*, Humana Press (2005), which are each incorporated by reference. In addition, custom peptides and proteins can also be ordered from various commercial suppliers including, e.g., Sigma-Genesis Co. (The Woodlands, Tex., USA), Biopeptide Co., LLC (San Diego, Calif., USA), and Invitrogen Corp. (Carlsbad, Calif., USA).

In certain embodiments, reagents of the invention are immunoglobulins or antibodies that include substantially non-fluorescent donor moieties, acceptor moieties, and/or quencher moieties as described herein. Antibodies suitable for use in these embodiments of invention may be prepared and labeled by conventional methodology and/or by genetic engineering. Antibody fragments may be genetically engineered, e.g., from the variable regions of the light and/or heavy chains ($V_H$ and $V_L$), including the hypervariable regions, or from both the $V_H$ and $V_L$ regions. For example, the term "immunoglobulin" or "antibodies" as used herein includes polyclonal and monoclonal antibodies and biologically active fragments thereof including among other possibilities "univalent" antibodies (Glennie et al. (1982) *Nature* 295:712); Fab proteins including Fab' and F(ab')$_2$ fragments whether covalently or non-covalently aggregated; light or heavy chains alone, typically variable heavy and light chain regions ($V_H$ and $V_L$ regions), and more typically including the hypervariable regions (otherwise known as the complementarity determining regions (CDRs) of the $V_H$ and $V_L$ regions); $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques, mutagenic techniques, or other directed evolutionary techniques known in the art. Labeled immunoglobulins can be used in a variety of well known assays including, e.g., fluorescent immunoassays.

Other exemplary reagents of the invention include lipids and carbohydrates that include substantially non-fluorescent donor moieties, acceptor moieties, and/or quencher moieties as described herein. Aspects of lipid and/or carbohydrate chemistry and synthesis are also described in, e.g., Tyman (Ed.), *Surfactants in Lipid Chemistry: Recent Synthetic, Physical, and Biodegradative Studies*, The Royal Society of Chemistry (1992), Gurr et al., *Lipid Biochemistry*, 5th Ed., Iowa State Press (2001), Min Kuo et al. (Eds.), *Lipid Biotechnology*, Marcel Dekker (2002), Ogura et al. (Eds.), *Carbohydrates-Synthetic Methods and Applications in Medicinal Chemistry*, VCH Publishers, Inc. (1993), Derek Horton et al. (Eds.), *Trends in Synthetic Carbohydrate Chemistry*, American Chemical Society (1989), Gunstone et al., *Lipid Handbook*, 2nd Ed., CRC Press (1994), Scherz et al., *Analytical Chemistry of Carbohydrates*, John Wiley & Sons, Inc. (2002), Boons (Ed.), *Carbohydrate Chemistry*, Chapman & Hall (1997), Davis et al., *Carbohydrate Chemistry*, Oxford University Press (2002), which are each incorporated by reference.

Reaction Mixtures

The invention also provides many different reaction mixtures that can be used in a wide variety of applications. In some embodiments, for example, reaction mixtures are utilized in performing homogeneous amplification/detection assays (e.g., real-time PCR monitoring), nucleic acid sequencing procedures, biopolymer synthesis protocols (e.g., peptide synthesis or oligonucleotide synthesis), or biopolymer labeling reactions. Many of these applications are described further below or are otherwise referred to herein.

In certain embodiments, the reaction mixtures of the invention include selected amounts of nucleotides, primers, and/or probes. Typically, one or more of these nucleotides, primers, and/or probes are labeled with at least one substantially non-fluorescent donor moiety, acceptor moiety, and/or quencher moiety. The nucleotides of these reaction mixtures are typically extendible nucleotides and/or terminator nucleotides, e.g., for use in nucleic acid amplification reactions or nucleic acid sequencing reactions. Essentially any terminator nucleotide that is known to persons of skill in the art is optionally utilized. Some exemplary terminator nucleotides that can be used in some embodiments are also described in, e.g., U.S. Pat. No. 5,273,638, entitled "NUCLEOTIDE SEQUENCE DETERMINATION EMPLOYING MATCHED DIDEOXYNUCLEOTIDE TERMINATOR CONCENTRATIONS," issued Dec. 28, 1993 to Konrad et al., U.S. Patent Application Publication No. US2005/0037398, entitled "2'-TERMINATOR NUCLEOTIDE-RELATED METHODS AND SYSTEMS," filed Jun. 28, 2004 by Gelfand et al., and U.S. Patent Application Publication No. US2005/0037991, entitled "SYNTHESIS AND COMPOSITIONS OF 2'-TERMINATOR NUCLEOTIDES," filed Jun. 28, 2004 by Bodepudi et al., which are each incorporated by reference. Probes that are included in these reaction mixtures generally include, e.g., hybridization probes, 5'-nuclease probes, and/or hairpin probes.

In addition, reaction mixtures also generally include various reagents that are useful in performing nucleic acid amplification or detection reactions (e.g., real-time PCR monitoring or 5'-nuclease assays), or nucleic acid sequencing reactions. Exemplary types of these other reagents include, e.g., template or target nucleic acids, nucleotide incorporating biocatalysts (e.g., DNA polymerases), buffers, salts, amplicons, glycerol, metal ions, dimethyl sulfoxide (DMSO), and poly rA. Nucleic acid amplification and detection as well as other methods are also described further below.

Reaction mixtures are generally produced by combining selected nucleotides, primers, and/or probes, as described above, with quantities of the other reagents that are sufficient for performing the particular application that is selected. The quantities of reagents to be included in a given reaction mixture will be apparent to persons of skill in the art in view of the selected method to be performed. To illustrate, however, primer nucleic acids and extendible nucleotides (e.g., four dNTPs (dGTP, dCTP, dATP, dTTP)) are each typically present in a large molar excess in these reaction mixtures. Probes and primers that can be utilized in the reaction mixtures of the invention are described herein. Suitable extendible and/or terminator nucleotides are readily available from many different commercial suppliers including, e.g., Roche Diagnostics Corporation (Indianapolis, Ind., USA), Amersham Biosciences Corp. (Piscataway, N.J., USA), and Applied Biosystems (Foster City, Calif., USA).

The nucleotide incorporating biocatalysts utilized in the reaction mixtures and other aspects of the invention typically comprise enzymes, such as polymerases, terminal transferases, reverse transcriptases, telomerases, and polynucleotide phosphorylases. In certain embodiments, for example, the enzyme includes a 5'-3' nuclease activity, a 3'-5' exonuclease activity, and/or is a thermostable enzyme. The enzyme is optionally derived from an organism, such as *Thermus antranikianii*, *Thermus aquaticus*, *Thermus caldophilus*, *Thermus chliarophilus*, *Thermus filiformis*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Anaerocellum thermophilum*, *Bacillus caldotenax*, and *Bacillus stearothermophilus*.

In certain embodiments, additional reagents are also added to the reaction mixtures of the invention. To illustrate, reaction mixtures also optionally include pyrophosphatases (e.g., a thermostable pyrophosphatase), e.g., for use in minimizing pyrophosphorolysis, uracil N-glycosylase (UNG) (e.g., a thermostable UNG), e.g., to protect against carry-over contamination.

Additional exemplary reaction mixtures of the present invention include biopolymer synthesis reagents as described herein (e.g., nucleic acid synthesis reagents, such as phosphoramidites, or polypeptide synthesis reagents). These reaction mixtures are typically used in biopolymer synthesis processes as referred to herein or otherwise known to those of skill in the art.

Many reaction mixtures that can be adapted for use with the biomolecules and other reagents of the invention are also described in, e.g., *Current Protocols in Molecular Biology* (Ausubel et al., ed., J. Wiley & Sons Inc., New York, 1997 and supplemented through Supplement No. 75, August 2006) (Ausubel 1), Ausubel et al. (Eds.), *Short Protocols in Molecular Biology: A Compendium of Methods from Current Protocols in Molecular Biology*, 5th Ed., John Wiley & Sons, Inc. (2002) (Ausubel 2), Sambrook et al., *Molecular Cloning: A Laboratory Manual*, 3rd Ed., Cold Spring Harbor Laboratory Press (2000) (Sambrook), Berger and Kimmel, *Guide to Molecular Cloning Techniques: Methods in Enzymology*, Volume 152, Academic Press, Inc. (Berger), Vorbruggen et al., *Handbook of Nucleoside Synthesis*, Organic Reactions Series, #60, John Wiley & Sons, Inc. (2001), Gait (Ed.) *Oligonucleotide Synthesis*, Oxford University Press (1984), Hames and Higgins, *Nucleic Acid Hybridization*, Practical Approach Series, Oxford University Press (1997), and Hames and Higgins (Eds.) *Transcription and Translation*, Practical Approach Series, Oxford University Press (1984), all of which are incorporated by reference.

Methods of Using Biomolecules Comprising Substantially Non-Fluorescent Donor Moieties The invention also provides methods of using the labeled biomolecules described herein. In some embodiments, for example, these biomolecules are used to perform assays that involve the detection of target nucleic acids or other biomolecules, e.g., to provide diagnostic, genetic, or other information about subjects from which these targets were derived. The use of substantially non-fluorescent donor moieties in these methods generally leads to reduced background fluorescence relative to procedures that utilize conventional donor moieties. Accordingly, this typically improves performance characteristics, such as the sensitivity and dynamic range of the particular assay in which these substantially non-fluorescent donor moieties are utilized. These aspects are also illustrated in the examples provided below.

The biomolecules described herein are optionally used or adapted for use in essentially any application that involves the transfer of energy to effect analyte detection. Examples of nucleic acid-related types of applications, include the analysis of the structure and conformation of nucleic acids, real-time PCR assays, and SNP detection (Myakishev et al. (2001) "High-throughput SNP genotyping by allele-specific PCR with universal energy-transfer-labeled primers," *Genome Res* 11:163-169, Lee et al. (1999) "Seven-color, homogeneous detection of six PCR products," *Biotechniques* 27:342-349, Thelwell et al. (2000) "Mode of action and application of Scorpion primers to mutation detection," *Nucleic Acids Res* 28:3752-3761, Whitcombe et al. (1999) "Detection of PCR products using self-probing amplicons and fluorescence," *Nat Biotechnol* 17:804-807, Heid et al. (1996) "Real time quantitative PCR," *Genome Res* 6:986-994, Nazarenko et al. (1997) "A closed tube format for amplification and detection of DNA based on energy transfer," *Nucleic Acids Res* 25:2516-2521, which are each incorporated by reference); detection of nucleic acid hybridization (Parkhurst et al. (1995) "Kinetic studies by fluorescence resonance energy transfer employing a double-labeled oligonucleotide: hybridization to the oligonucleotide complement and to single-stranded DNA," *Biochemistry* 34:285-292, Tyagi et al. (1996) "Molecular beacons: probes that fluoresce upon hybridization," *Nat Biotechnol* 14:303-308, Tyagi et al. (1998) "Multicolor molecular beacons for allele discrimination," *Nat Biotechnol* 16:49-53, Sixou et al. (1994) "Intracellular oligonucleotide hybridization detected by fluorescence resonance energy transfer (FRET)," *Nucleic Acids Res* 22:662-668, and Cardullo et al. (1988) "Detection of nucleic acid hybridization by nonradiative fluorescence resonance energy transfer," *Proc Natl Acad Sci USA* 85:8790-8794, which are each incorporated by reference); primer-extension assays for detecting mutations (Chen et al. (1997) "Fluorescence energy transfer detection as a homogeneous DNA diagnostic method," *Proc Natl Acad Sci USA* 94:10756-10761, which is incorporated by reference); and automated DNA sequencing (Woolley et al. (1995) "Ultra-high-speed DNA sequencing using capillary electrophoresis chips," *Anal Chem* 67:3676-3680, Hung et al. (1998) "Comparison of fluorescence energy transfer primers with different donor-acceptor dye combinations," *Anal Biochem* 255:32-38, and Ju et al. (1995) "Fluorescence energy transfer dye-labeled primers for DNA sequencing and analysis," *Proc Natl Acad Sci USA* 92:4347-4351, which are each incorporated by reference).

Examples of protein-related types of applications, include the analysis of the structure and conformation of proteins (Xing et al. (1995) "Internal movement in myosin subfragment 1 detected by fluorescence resonance energy transfer," *Biochemistry* 34:6475-6487, Luo et al. (1998) "Localization of Cys133 of rabbit skeletal troponin-I with respect to troponin-C by resonance energy transfer," *Biophys J* 74:3111-3119, Erickson et al. (1995) "Use of resonance energy transfer to determine the proximity of the guanine nucleotide binding site of transducin relative to a conformationally-sensitive site on the gamma subunit of the cyclic GMP phosphodiesterase," *Biochemistry* 34:8693-8700, and Taniguchi et al. (1993) "Reversible changes in the fluorescence energy transfer accompanying formation of reaction intermediates in probe-labeled (Na+,K+)-ATPase," *J Biol Chem* 268:15588-15594, which are each incorporated by reference); the analysis of the spatial distribution and assembly of protein complexes (Moens et al. (1994) "Determination of the radial coordinate of Cys-374 in F-actin using fluorescence resonance energy transfer spectroscopy: effect of phalloidin on polymer assembly," *Biochemistry* 33:13102-13108, Watson et al. (1995) "Macromolecular arrangement in the aminoacyl-tRNA.elongation factor Tu.GTP ternary complex. A fluorescence energy transfer study," *Biochemistry* 34: 7904-7912, Adair et al. (1994) "Glycophorin A helical transmembrane domains dimerize in phospholipid bilayers: a resonance energy transfer study," *Biochemistry* 33:5539-5544, and Matyus (1992) "Fluorescence resonance energy transfer measurements on cell surfaces. A spectroscopic tool for determining protein interactions," *J Photochem Photobiol* 12:323-337, which are each incorporated by reference); the analysis of receptor/ligand interactions (Berger et al. (1994) "Complex molecular mechanism for dihydropyridine binding to L-type Ca(2+)-channels as revealed by fluorescence resonance energy transfer," *Biochemistry* 33:11875-11883, Gagne et al. (2002) "Use of fluorescence polarization detection for the measurement of Fluopeptide™ binding to G protein-coupled receptors," *J Recept Signal Transduct Res* 22:333-343, and Poo et al. (1994) "Ligation of CD3 triggers transmembrane proximity between LFA-1 and cortical microfilaments in a cytotoxic T cell clone derived from tumor infiltrating lymphocytes: a quantitative resonance energy transfer microscopy study," *J Cell Physiol* 159:176-180, which are each incorporated by reference); and immunoassays (Morrison (1988) "Time-resolved detection of energy transfer: theory and application to immunoassays," *Anal Biochem* 174:101-120 and Khanna et al. (1980) "4',5'-Dimethoxy-6-carboxyfluorescein: a novel dipole-dipole coupled fluorescence energy transfer acceptor useful for fluorescence immunoassays," *Anal Biochem* 108:156-161, which are both incorporated by reference).

Examples of lipid-related and other types of applications, include the analysis analyses of the distribution and transport of lipids (Gutierrez-Merino et al. (1995) "Preferential distribution of the fluorescent phospholipid probes NBD-phosphatidylcholine and rhodamine-phosphatidylethanolamine in the exofacial leaflet of acetylcholine receptor-rich membranes from Torpedo marmorata," *Biochemistry* 34:4846-4855 and Wolf et al. (1992) "Determination of the transbilayer distribution of fluorescent lipid analogues by nonradiative fluorescence resonance energy transfer," *Biochemistry* 31:2865-2873, which are both incorporated by reference); membrane fusion assays (Pecheur et al. (1998) "Membrane fusion induced by 11-mer anionic and cationic peptides: a structure-function study," *Biochemistry* 37:2361-2371 and Partearroyo et al. (1994) "Real-time measurements of chemically-induced membrane fusion in cell monolayers, using a resonance energy transfer method," *Biochim Biophys Acta* 1189:175-180, which are both incorporated by reference); membrane potential sensing assays (Gonzalez et al. (1995) "Voltage sensing by fluorescence resonance energy transfer in single cells," *Biophys J* 69:1272-1280, which is incorporated by reference); the analysis of fluorogenic protease substrates (Kurth et al. (1998) "Engineering the S1' subsite of trypsin: design of a protease which cleaves between dibasic residues," *Biochemistry* 37:11434-11440 and Gulnik et al. (1997) "Design of sensitive fluorogenic substrates for human cathepsin D," *FEBS Lett* 413:379-384, which are both incorporated by reference); the analysis of indicators for cyclic AMP (Adams et al. (1991) "Fluorescence ratio imaging of cyclic AMP in single cells," *Nature* 349:694-697, which is incorporated by reference) and zinc (Godwin et al. (1996) "A Fluorescent Zinc Probe Based on Metal-Induced Peptide Folding," *J Am Chem Soc* 118:6514, which is incorporated by reference); and the analysis of probing interactions of single molecules (Ha et al. (1996) "Probing the interaction between two single molecules: fluorescence resonance energy transfer between a single donor and a single acceptor," *Proc Natl Acad Sci USA* 93:6264-6268, which is incorporated by reference).

To further illustrate, examples of general types of nucleic acid analysis technologies that can be used or adapted for use to analyze target nucleic acids in or from, e.g., the reactions mixtures of the invention include various nucleic acid amplification assays. A common characteristic among nucleic acid amplification assays is that they are typically designed to amplify nucleic acid sequences that are specific for the organism being detected. Nucleic acid amplification tests generally have greater sensitivity than other approaches to nucleic acid analysis. This sensitivity, which is further improved with the use of the substantially non-fluorescent donor moieties describe herein, is typically attributable to their ability to produce a positive signal from as little as a single copy of the target nucleic acid. Amplification methods that are optionally utilized or adapted to detect target nucleic acids include, e.g., various polymerase, ligase, or reverse-transcriptase mediated amplification methods, such as the polymerase chain reaction (PCR), the ligase chain reaction (LCR), and/or the reverse-transcription PCR (RT-PCR). Additional details regarding the use of these and other amplification methods and various approaches to sample preparation for these assays can be found in any of a variety of standard texts, including, e.g., Berger, Sambrook, Ausubel 1 and 2, and Innis, which are referred to above.

Various commercial nucleic acid amplification assays that are optionally adapted for use with the reagents and methods of the invention generally differ in their amplification methods and their target nucleic acid sequences. Examples of these commercial tests include hybridization probe assays (e.g., using the LightCycler® system) and the AMPLICOR® and COBAS AMPLICOR® assays (Roche Diagnostics Corporation, Indianapolis, Ind., USA), which use polymerase chain reactions (PCR); the LCx® test (Abbott Laboratories, Abbott Park, Ill., USA), which uses ligase chain reactions (LCR); the BDProbeTec™ ET test (Becton, Dickinson and Company, Franklin Lakes, N.J., USA), which uses strand displacement amplification (SDA); and the APTIMA™ assay (Gen-Probe, Inc., San Diego, Calif., USA), which uses transcription-mediated amplification (TMA). Nucleic acid amplification and detection is described further below.

In certain embodiments, for example, the 5'-nuclease probes of the invention are utilized in various 5'-nuclease reactions. Many 5'-nuclease assays are well known to those of skill in the art. Examples of such reactions are also described in, e.g., U.S. Pat. No. 6,214,979, entitled "HOMOGENEOUS ASSAY SYSTEM," issued Apr. 10, 2001 to Gelfand et al., U.S. Pat. No. 5,804,375, entitled "REACTION MIXTURES FOR DETECTION OF TARGET NUCLEIC ACIDS," issued Sep. 8, 1998 to Gelfand et al., U.S. Pat. No. 5,487,972, entitled "NUCLEIC ACID DETECTION BY THE 5'-3' EXONUCLEASE ACTIVITY OF POLYMERASES ACTING ON ADJACENTLY HYBRIDIZED OLIGONUCLEOTIDES," issued Jan. 30, 1996 to Gelfand et al., and U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., which are each incorporated by reference.

Figure 2:
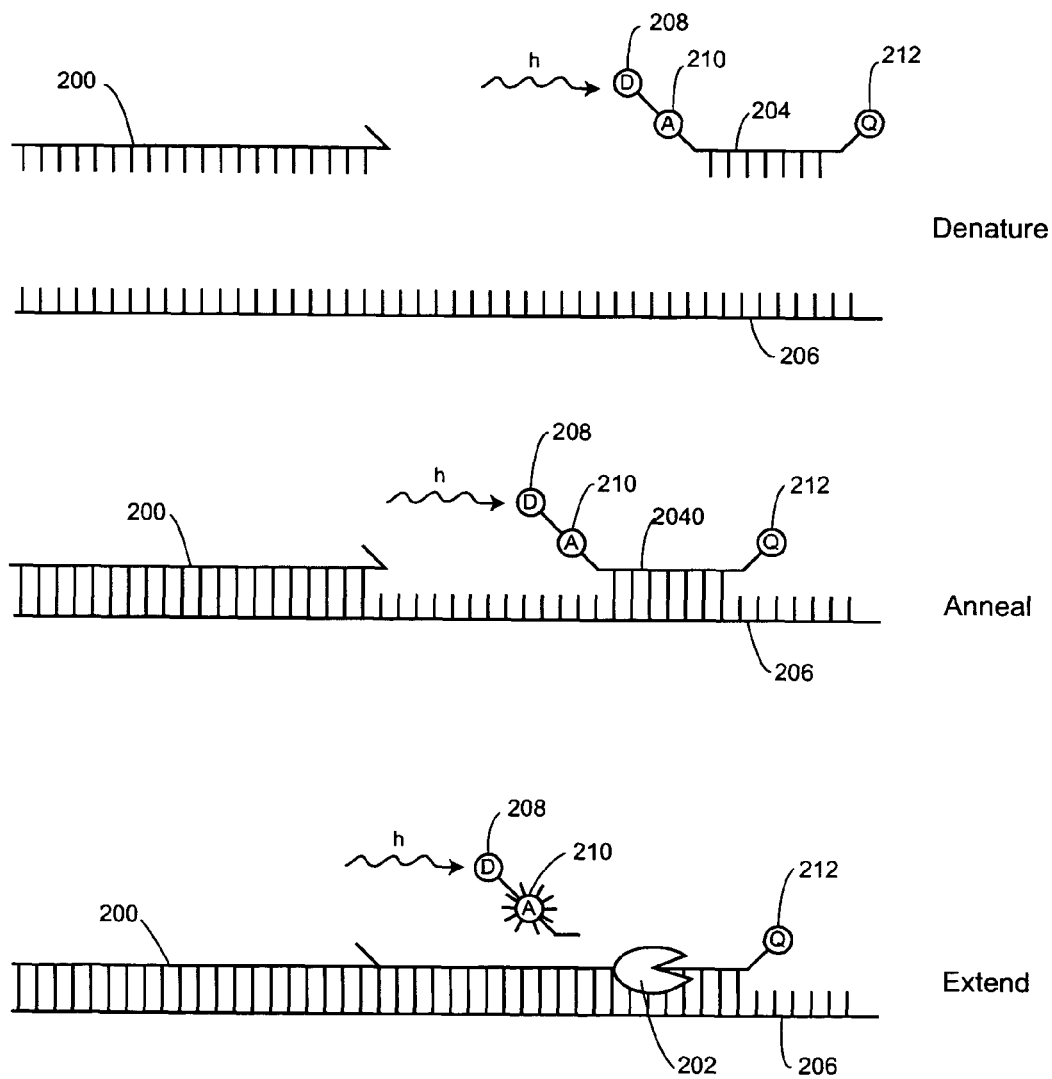
FIG. 2 schematically depicts certain steps performed in a 5'-nuclease reaction according to one embodiment of the invention.

To briefly illustrate, in a 5'-nuclease reaction, a target nucleic acid is contacted with a primer and a probe (e.g., a 5'-nuclease probe of the invention) under conditions in which the primer and probe hybridize to a strand of the target nucleic acid. The target nucleic acid, primer and probe are also contacted with a nucleic acid polymerase having 5' to 3' nuclease activity. Nucleic acid polymerases possessing 5' to 3' nuclease activity can cleave the probe hybridized to the target nucleic acid downstream of the primer. The 3' end of the primer provides the initial binding site for the polymerase. The bound polymerase cleaves fragments from the probe upon encountering the 5' end of the probe. This process is also schematically depicted in FIG. 2. As shown, during the extension of primer 200, polymerase 202 cleaves 5'-nuclease probe 204, which is annealed to target or template 206, to release substantially non-fluorescent donor moiety (D) 208 and acceptor moiety (A) 210 from the remaining portion of 5'-nuclease probe 204, which includes quencher moiety (Q) 212. Prior to cleavage, quencher moiety (Q) 212 quenches fluorescent emissions from acceptor moiety (A) 210, whereas as shown, following this cleavage process quencher moiety (Q) 212 no longer quenches fluorescent emissions from acceptor moiety (A) 210. In another exemplary embodiment, 5'-nuclease probes include only substantially non-fluorescent donor and acceptor moieties. In these embodiments, the intensity of fluorescent emissions from the acceptor moieties generally decreases following cleavage as the donor and acceptor moieties separate from one another.

The primer and probe can be designed so that they anneal in close proximity on the target nucleic acid such that binding of the nucleic acid polymerase to the 3' end of the primer puts it in contact with the 5' end of the probe in the absence of primer extension. The term "polymerization-independent cleavage" refers to this process. Alternatively, if the primer and probe anneal to more distantly spaced regions of the target nucleic acid, polymerization typically occurs before the nucleic acid polymerase encounters the 5' end of the probe. As the polymerization continues, the polymerase progressively cleaves fragments from the 5' end of the probe. This cleavage continues until the remainder of the probe has been destabilized to the extent that it dissociates from the template molecule. The term "polymerization-dependent cleavage" refers to this process.

One advantage of polymerization-independent cleavage lies in the elimination of the need for amplification of the nucleic acid. Provided the primer and probe are adjacently bound to the nucleic acid, sequential rounds of probe annealing and cleavage of fragments can occur. Thus, a sufficient amount of fragments can be generated, making detection possible in the absence of polymerization.

In either process, a sample is provided which is thought to contain the target nucleic acid. The target nucleic acid contained in the sample may be first reverse transcribed into cDNA, if necessary, and then denatured, using any suitable denaturing method, including physical, chemical, or enzymatic methods, which are known to those of skill in the art. An exemplary physical approach to effect strand separation involves heating the nucleic acid until it is completely (>99%) denatured. Typical heat denaturation involves temperatures ranging from about 85° C. to about 105° C., for periods of time ranging from about 1 to about 10 minutes. As an alternative to denaturation, the nucleic acid may exist in a single-stranded form in the sample, such as when the sample comprises single-stranded RNA or DNA viruses.

The denatured target nucleic acid strand is typically incubated with a primer and a probe under hybridization conditions that permit the primer and probe to bind to the target nucleic acid strand. In some embodiments, two primers can be used to amplify the target nucleic acid. The two primers are typically selected so that their relative positions along the target nucleic acid are such that an extension product synthesized from one primer, when the extension produce is separated from its template (complement), serves as a template for the extension of the other primer to yield a replicate strand of defined length.

Because the complementary strands are typically longer than either the probe or primer, the strands have more points of contact and thus a greater chance of binding to each other over a given period of time. Accordingly, a high molar excess of probe and primer is typically utilized to favor primer and probe annealing over template strand reannealing. In multiplexing formats, multiple probes are typically used in a single reaction vessel to simultaneously detect multiple target nucleic acids.

Primers are generally of sufficient length and complementarity so that they selectively bind to target nucleic acids under selected conditions to permit polymerization-independent cleavage or polymerization-dependent cleavage to proceed. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the primer typically includes about 15-30 nucleotides, although it may contain more or fewer nucleotides.

The probe is generally annealed to its complementary target nucleic acid before the nucleic acid polymerase encounters that region of the target nucleic acid, thereby permitting the 5' to 3' nuclease activity of the enzyme to cleave fragments from the probe. To enhance the likelihood that the probe will anneal to the target nucleic acid before the polymerase reaches this region of hybridization, a variety of techniques may be utilized. For example, short primers generally require cooler temperature to form sufficiently stable hybrid complexes with the nucleic acid. Therefore, the probe can be designed to be longer than the primer so that the probe preferentially anneals to the target nucleic acid at higher temperatures relative to primer annealing. To further illustrate, the nucleotide composition of the probe can be chosen to have greater G/C content and, consequently, greater thermal stability than the primer. Optionally, modified nucleotides may be incorporated into primers or probes to effect either greater or lesser thermal stability in comparison to primers or probes having only unmodified nucleotides. Exemplary modified nucleotides are described further above. The thermocycling parameters can also be varied to take advantage of the differential thermal stability of the probe and primer. For example, following a thermocycling denaturation step, an intermediate temperature may be introduced which permits probe binding, but not primer binding. Thereafter, the temperature can be further reduced to permit primer annealing. To preferentially favor binding of the probe before the primer, a high molar excess of probe to primer concentration can also be used. Such probe concentrations are typically in the range of about 2 to about 20 times higher than the respective primer concentration, which is generally about $0.5-5\times10^{-7}$ M.

Template-dependent extension of primers is generally catalyzed by a nucleotide incorporating biocatalyst (e.g., a polymerase) in the presence of adequate amounts of the four deoxyribonucleoside triphosphates (dATP, dGTP, dCTP, and dTTP) or analogs in a reaction mixture that also includes appropriate salts, metal cations, and buffers. Reaction mixtures are described further above. Suitable nucleotide incorporating biocatalysts are enzymes known to catalyze primer and template-dependent DNA synthesis and possess the 5' to 3' nuclease activity. Exemplary DNA polymerases of this type include *E. coli* DNA polymerase I, Tth DNA polymerase, *Bacillus stearothermophilus* DNA polymerase, Taq DNA polymerase, *Thermus* sp. Z05 DNA polymerase, *Thermatoga maritima* DNA polymerase, *Thermatoga neopolitana* DNA polymerase, and *Thermosipho africanus* DNA polymerase. The reaction conditions for catalyzing DNA synthesis with these DNA polymerases are well known in the art. Typically, the nucleotide incorporating biocatalyst efficiently cleaves the probe and releases labeled fragments so that a detectable signal is directly or indirectly generated.

The products of the synthesis are generally duplex molecules that include the template strands and the primer extension strands. Byproducts of this synthesis are probe fragments, which can include a mixture of mono-, di- and larger nucleotide fragments. Repeated cycles of denaturation, probe and primer annealing, and primer extension and probe cleavage result in the exponential accumulation of the region defined by the primers and the exponential generation of labeled fragments. Sufficient cycles are run to achieve a detectable amount of probe fragments, which is generally several orders of magnitude greater than background signal. The use of the donor moieties as described herein can effectively reduce the number of cycles run before a detectable signal is produced relative to assays that do not reduce these background signals.

In certain embodiments, PCR reactions are carried out as an automated process, which utilizes a thermostable enzyme. In this process the reaction mixture is cycled through a denaturing step, a probe and primer annealing step, and a synthesis step in which cleavage and displacement occur concurrently with primer dependent template extension. In some embodiments, the methods described herein are performed using a system. Such systems are described in greater detail below. Optionally, thermal cyclers, such as those commercially available from, e.g., Applied Biosystems (Foster City, Calif., USA), which are designed for use with thermostable enzymes, may be utilized.

Thermostable polymerases are typically used in automated processes that effect the denaturation of double stranded extension products by exposing them to a elevated temperatures (e.g., about 95° C.) during the PCR cycle. For example, U.S. Pat. No. 4,889,818, entitled "PURIFIED THERMOSTABLE ENZYME," issued to Dec. 26, 1989 to Gelfand et al., which is incorporated by reference, discloses a representative thermostable enzyme isolated from *Thermus aquaticus*. Additional representative thermostable polymerases include, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermatoga*

*neopolitana, Thermosipho africanus, Thermococcus littoralis,* and *Methanothermus fervidus.*

Hybridization of probes to target nucleic acids can be accomplished by choosing appropriate hybridization conditions. The stability of the probe:target nucleic acid hybrid is typically selected to be compatible with the assay and washing conditions so that stable, detectable hybrids form only between the probes and target nucleic acids. Manipulation of one or more of the different assay parameters determines the exact sensitivity and specificity of a particular hybridization assay.

More specifically, hybridization between complementary bases of nucleic acids (e.g., DNA, RNA, PNA, or combinations thereof), occurs under a wide variety of conditions that vary in temperature, salt concentration, electrostatic strength, and buffer composition. Examples of these conditions and methods for applying them are described in, e.g., Tijssen, *Hybridization with Nucleic Acid Probes*, Vol. 24, Elsevier Science (1993), and Hames and Higgins, supra, which are both incorporated by reference. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. Hybridization between nucleic acids may be facilitated using buffers such as Tris-EDTA (TE), Tris-HCl and HEPES, salt solutions (e.g. NaCl, KCl, $MgCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin.

Essentially any available method for detecting target nucleic acids can be used in the present invention. Common approaches include real-time amplification detection with 5'-nuclease probes, hybridization probes, or hairpin probes (e.g., molecular beacons), detection of labels incorporated into the amplification primers or the amplified nucleic acids themselves, e.g., following electrophoretic separation of the amplification products from unincorporated labels, hybridization based assays (e.g., array based assays), and/or detection of secondary reagents that bind to the nucleic acids. These general approaches are also described in, e.g., Sambrook, and Ausubel 1 and 2, supra.

Hairpins probes, such as molecular beacons, are oligonucleotides designed for real-time detection and quantification of target nucleic acids. The 5' and 3' termini of hairpin probes generally comprise the labeling moieties, which confer the detectable properties of the probe. In an exemplary embodiment, one of the termini is attached to a substantially non-fluorescent donor moiety and to an acceptor moiety (e.g., a fluorescent dye) and the other terminus is attached to a quencher moiety capable of quenching fluorescent emissions from the acceptor moiety. When the hairpin probe is present free in solution, i.e., not hybridized to a second nucleic acid, the stem of the probe is stabilized by complementary base pairing. This self-complementary pairing results in a "hairpin loop" structure for the probe in which the acceptor and quencher moieties are proximal to one another. In this confirmation, the quencher moiety quenches the acceptor moiety.

The loop of a hairpin probe typically comprises a sequence that is complementary to the sequence to be detected in the target nucleic acid, such that hybridization of the loop to its complementary sequence in the target forces disassociation of the stem, thereby distancing the acceptor and quencher moieties from each other. This unquenches the acceptor moiety, causing an increase in fluorescence from the hairpin probe.

Figure 3:
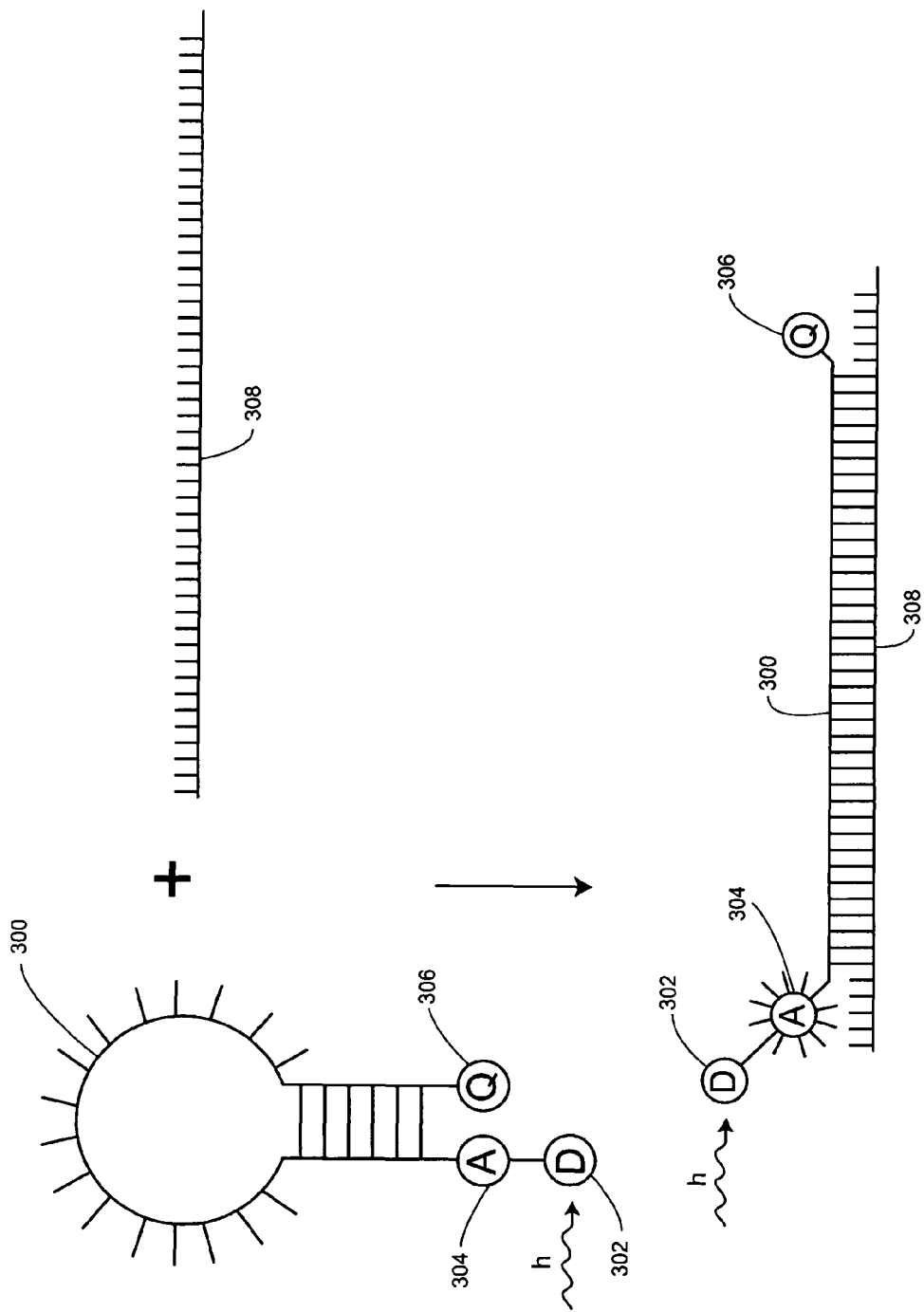
FIG. 3 schematically depicts some steps performed in an assay that involves hairpin probes according to one embodiment of the invention.

To further illustrate, FIG. 3 schematically shows hairpin probe 300, which includes substantially non-fluorescent donor moiety (D) 302, acceptor moiety (A) 304, and quencher moiety (Q) 306. As shown, quencher moiety (Q) 306 quenches fluorescent emissions from acceptor moiety (A) 304 when hairpin probe 300 is free in solution, but not when hairpin probe 300 is hybridized with target nucleic acid 308. In another representative embodiment, hairpin probes include only substantially non-fluorescent donor and acceptor moieties. In these embodiments, the intensity of fluorescence from the acceptor moieties typically decreases when the probes hybridize with the target nucleic acids due to the conformational changes in the probes.

Details regarding standard methods of making and using hairpin probes are generally known to persons of skill in the art and are also described in, e.g., Leone et al. (1995) "Molecular beacon probes combined with amplification by NASBA enable homogenous real-time detection of RNA," *Nucleic Acids Res.* 26:2150-2155, Kostrikis et al. (1998) "Molecular beacons: spectral genotyping of human alleles" *Science* 279:1228-1229, Fang et al. (1999) "Designing a novel molecular beacon for surface-immobilized DNA hybridization studies" *J. Am. Chem. Soc.* 121:2921-2922, and Marras et al. (1999) "Multiplex detection of single-nucleotide variation using molecular beacons" *Genet. Anal. Biomol. Eng.* 14:151-156, which are each incorporated by reference. A variety of commercial suppliers produce standard and custom hairpin probes that can be adapted for use in the methods described herein, including Oswel Research Products Ltd. (UK), Research Genetics (a division of Invitrogen, Huntsville, Ala., USA), and the Midland Certified Reagent Company (Midland, Tex., USA). A variety of kits that utilize hairpin probes are also commercially available, such as the Sentinel™ Molecular Beacon Allelic Discrimination Kits from Stratagene (La Jolla, Calif., USA) and various kits from Eurogentec SA (Belgium) and Isogen Bioscience BV (Netherlands). These kits are also optionally adapted for use in the methods described herein.

Hybridization probes generally function in pairs and can be used to effect various types of real-time target nucleic acid detection, including quantification, mutation detection, melting temperature ($T_m$) multiplexing, and color multiplexing. Aspects of certain hybridization probe assays are also described in, e.g., Brega et al. (2004) "Real-time PCR for dihydrofolate reductase gene single-nucleotide polymorphisms in *Plasmodium vivax* isolates," *Antimicrob Agents Chemother.* 48(7):2581-2587, Perelle et al. (2004) "A Light-Cycler real-time PCR hybridization probe assay for detecting food-borne thermophilic Campylobacter," *Mol Cell Probes.* 18(5):321-327, and Whiley et al. (2003) "Detection of Neisseria Meningitidis in clinical samples by a duplex real-time PCR targeting the porA and ctrA genes," *Mol Diagn.* 7(3-4): 141-145, which are each incorporated by reference.

Figure 4:
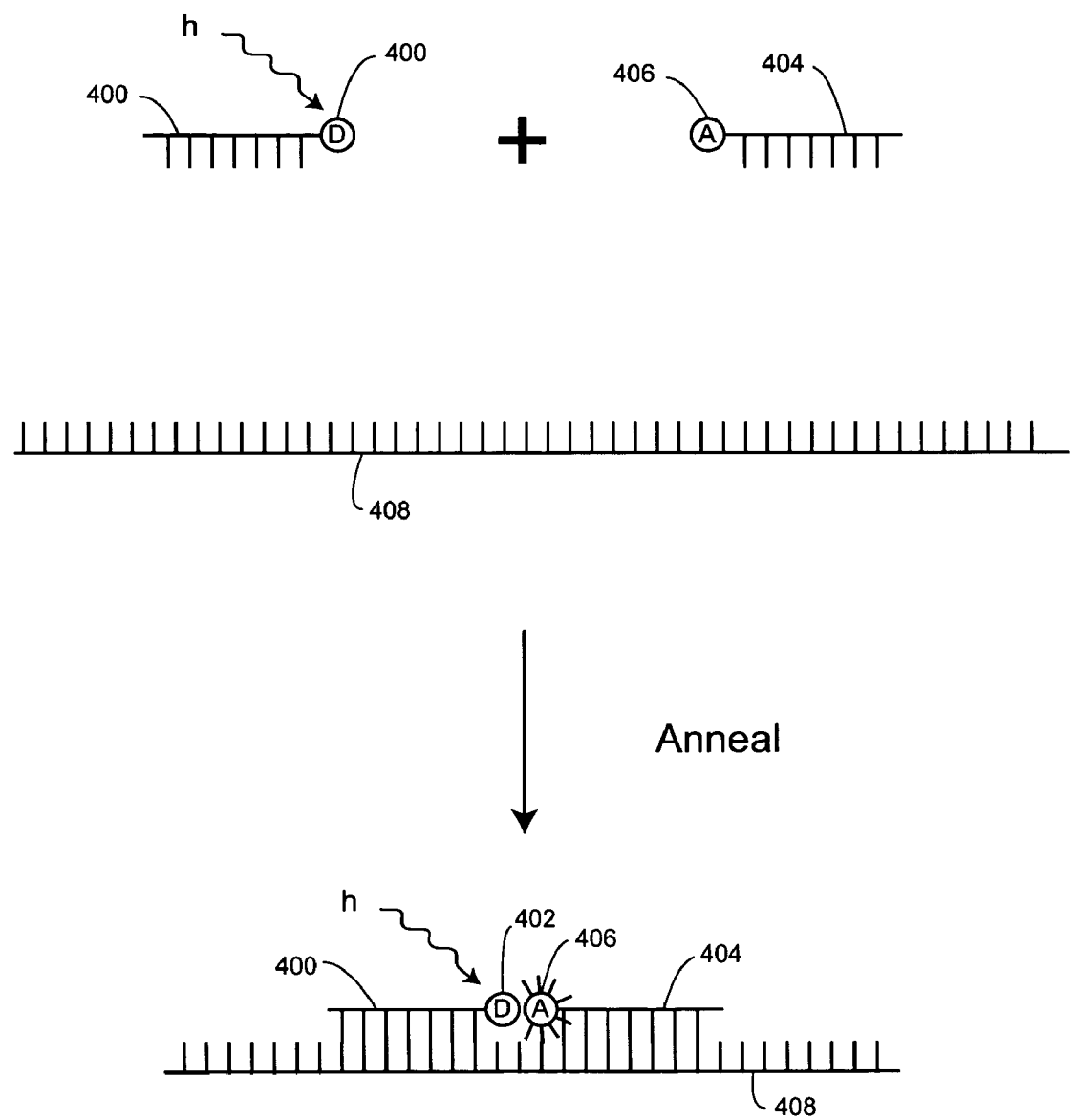
FIG. 4 schematically shows certain steps performed in an assay that involves hybridization probes according to one embodiment of the invention.

Hybridization probe assays typically include hybridizing a pair of labeled probes with a target or template nucleic acid within sufficient proximity to one another for energy transfer to occur between the labeling moieties. More specifically, one hybridization probe (a "donor probe") of the pair generally includes at least one substantially non-fluorescent donor moiety (e.g., 5- or 6-carboxy DmF), while the other hybridization probe (an "acceptor probe") of the pair includes at least one acceptor moiety (e.g., LC-Red 610, LC-Red 640, LC-Red 670, LC-Red 705, JA-270, CY5, or CY5.5). To further illustrate, FIG. 4 schematically shows that when donor probe 400 with substantially non-fluorescent donor moiety (D) 402 and acceptor probe 404 with acceptor moiety (A) 406 are free in solution, non-fluorescent excitation energy is not transferred from substantially non-fluorescent donor moiety (D) 402 to acceptor moiety (A) 406. In contrast, when donor probe 400 and acceptor probe 404 are both hybridized with target or template nucleic acid 408, acceptor moiety (A) 406 emits fluorescent energy in response to receiving non-fluorescent excitation energy transferred from substantially non-fluorescent donor moiety (D) 402, which is sufficiently proximal to acceptor moiety (A) 406 on target or template nucleic acid 408. In another exemplary embodiment, one hybridization probe of a pair includes both substantially non-fluorescent donor and acceptor moieties, while the other probe of the pair includes a quencher moiety. In this embodiment, detectable fluorescent emission from the acceptor moiety decreases when the pair of probes hybridizes with a target nucleic acid, because the quencher moiety quenches the fluorescence. The fluorescence emitted by the acceptor moieties of hybridization probes can be detected using various known methods, including those that utilize a LightCycler® system (Roche Diagnostics Corporation, Indianapolis, Ind., USA).

Figure 5:
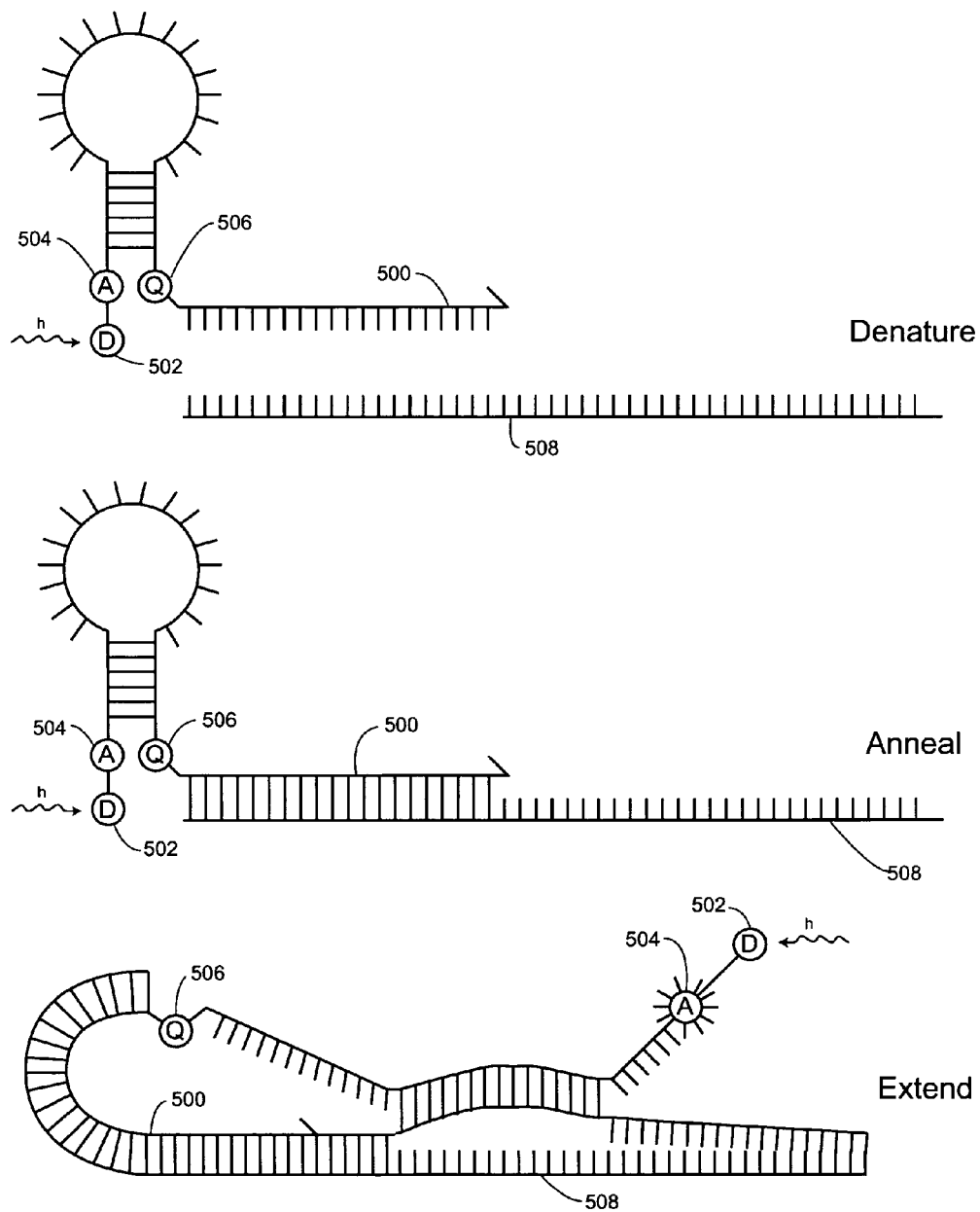
FIG. 5 schematically depicts certain steps performed in an assay that involves labeled primers according to one embodiment of the invention.

In other illustrative embodiments of using the biomolecules described herein, labeled primers are used to effect real-time target nucleic acid detection. For example, FIG. 5 schematically shows primer 500, which includes substantially non-fluorescent donor moiety (D) 502, acceptor moiety (A) 504, and quencher moiety (Q) 506. Prior to primer extension, primer 500 forms a hairpin loop structure such that quencher moiety (Q) 506 quenches fluorescence emitted by acceptor moiety (A) 504. Upon extension of primer 500 (bound to template nucleic acid 508), the hairpin loop structure dissociates and hybridizes to the newly formed complementary sequence, separating acceptor moiety (A) 504 from quencher moiety (Q) 506 such that fluorescent emissions from acceptor moiety (A) 504 can be detected. In other embodiments, primers comprise only substantially non-fluorescent donor and acceptor moieties. Primer-based approaches to real-time target nucleic acid detection that can be adapted for use with the biomolecules of the invention are also described in, e.g., Huang et al. (2004) "Real-time quantitative assay of telomerase activity using the duplex scorpion primer," Biotechnol Lett. 26(11):891-895, Asselbergs et al. (2003) "Rapid detection of apoptosis through real-time reverse transcriptase polymerase chain reaction measurement of the small cytoplasmic RNA Y1," Anal Biochem. 318(2): 221-229, and Nuovo et al. (1999) "In situ amplification using universal energy transfer-labeled primers," J Histochem Cytochem. 47(3):273-280, which are each incorporated by reference.

Another exemplary application of certain embodiments of the biomolecules described herein is in nucleic acid sequencing. In general, nucleic acid sequencing protocols involve an extension/termination reaction of a primer nucleic acid. Included in the reaction mixture are typically deoxynucleoside triphosphates (dNTPs) and polymerase enzymes, which are used to extend the primer. In addition, also included in the reaction mixture is at least one dideoxynucleoside triphosphate (ddNTP) or other terminator nucleotide, which when incorporated onto the extended primer prevents the further extension of the primer. After the extension reaction has been terminated, the different termination products that are formed are separated and analyzed in order to determine the base sequence of the target nucleic acid.

Nucleic acid sequencing is generally be divided into two classes, "dye primer sequencing" and "dye terminator sequencing". In dye primer sequencing, a fluorescent dye (e.g., a pair of acceptor and substantially non-fluorescent donor moieties as described herein) is incorporated onto the primer being extended. Four separate extension/termination reactions are then run in parallel, each extension reaction containing a different terminator nucleotide to terminate the extension reaction. Following termination, the reaction products are typically separated by gel electrophoresis and analyzed (Ansorge et al. (1987) Nucleic Acids Res. 15:4593-4602, which is incorporated by reference).

In one variation of dye primer sequencing, different primers are used in the four separate extension/termination reactions, each primer containing a different spectrally resolvable dye. After termination, the reaction products from the four extension/termination reactions are typically pooled, electrophoretically separated, and detected in a single lane (Smith et al. (1986) Nature 321:674-679, which is incorporated by reference). Thus, in this variation of dye primer sequencing, by using primers containing a set of spectrally resolvable dyes, products from more than one extension/termination reactions can be simultaneously detected.

In dye terminator sequencing, a fluorescent dye (e.g., a pair of acceptor and substantially non-fluorescent donor moieties as described herein) is attached to each of the terminator nucleotides (e.g., 2'-terminators or dideoxynucleoside triphosphates). An extension/termination reaction is then conducted where a primer is extended using deoxynucleoside triphosphates until the labeled terminator nucleotide is incorporated into the extended primer to prevent further extension of the primer. Once terminated, the reaction products for each terminator nucleotide are separated and detected. In one embodiment, separate extension/termination reactions are conducted for each of the four terminator nucleotides. In another embodiment, a single extension/termination reaction is conducted which contains the four terminator nucleotides, each labeled with a different, spectrally resolvable fluorescent dye as described herein.

Thus, according to one aspect of the invention, methods are provided for conducting dye primer sequencing using one or more oligonucleotide reagents of the present invention. According to this method, a mixture of extended labeled primers are formed by hybridizing a target nucleic acid with a labeled primer in the presence of deoxynucleoside triphosphates, at least one terminator nucleotide, and a polymerase. The labeled primer includes an oligonucleotide sequence complementary to a portion of the target nucleic acid sequence being sequenced, and an energy transfer fluorescent dye (e.g., a pair of acceptor and substantially non-fluorescent donor moieties as described herein) attached to the oligonucleotide.

According to this exemplary method, the polymerase extends the primer with the deoxynucleoside triphosphates until a terminator nucleotide is incorporated, which terminates extension of the primer. After termination, the extended primers in the mixture are typically separated (e.g., electrophoretically and/or chromatographically). The sequence of the target nucleic acid is then determined by detecting the extended primers.

In another exemplary embodiment of this method, four dye primer sequencing reactions are run, each primer sequencing reaction including a differently labeled primer and a different terminator nucleotide (e.g., ddATP, ddCTP, ddGTP and ddTTP). After the four dye primer sequencing reactions are run, the resulting mixtures of extended primers may be pooled. The extended primers in the mixture may then be separated and the fluorescent signal from each of the four differently labeled primers detected in order to determine the sequence of the target nucleic acid.

According to another embodiment of the invention, a method is provided for conducting dye terminator sequencing using one or more terminator nucleotides (e.g., 2'-terminator nucleotides or dideoxynucleoside triphosphates) labeled with an energy transfer dye of the present invention (e.g., a pair of acceptor and substantially non-fluorescent donor moieties as described herein). According to this method, a mixture of extended primers is formed by hybridizing a target nucleic acid with a primer in the presence of deoxynucleoside triphosphates, at least one labeled terminator nucleotide, and a polymerase. In some embodiments of this method, the step of forming a mixture of extended primers includes hybridizing the target nucleic acid with four differently labeled terminator nucleotides. The polymerase extends the primer with the deoxynucleoside triphosphates until a labeled terminator nucleotide is incorporated into the extended primer. After termination, the extended primers in the mixture are typically separated. The sequence of the target nucleic acid is then determined by detecting fluorescence from the labeled terminator nucleotide incorporated into the extended primer.

Figure 6:
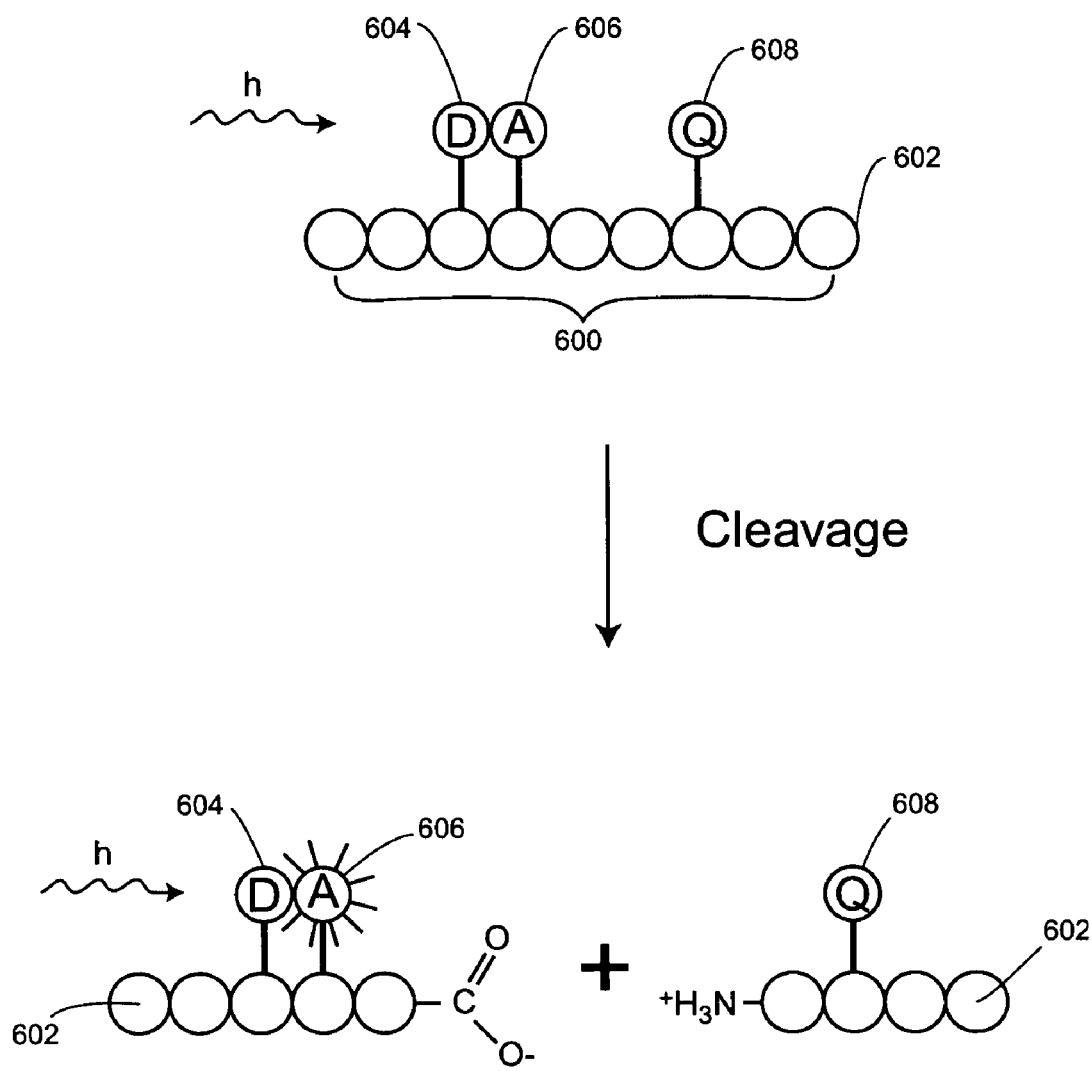
FIG. 6 schematically illustrates some steps performed in an assay that involves labeled proteins according to certain embodiments of the invention.

Other exemplary uses of the biomolecules of the invention include the analysis of proteins. For example, FIG. 6 schematically depicts an assay that can be used to assess responses to protein cleavage. As shown, certain amino acids 602 of protein 600 include substantially non-fluorescent donor moiety (D) 604, acceptor moiety (A) 606, or quencher moiety (Q) 608. Prior to cleavage (e.g., via protease cleavage and/or chemical cleavage), quencher moiety (Q) 608 quenches fluorescent emissions from acceptor moiety (A) 606, which accepts excitation energy transferred from substantially non-fluorescent donor moiety (D) 604. Following cleavage, quencher moiety (Q) 608 no longer quenches this fluorescence, which can be detected by various methods known to persons skilled in the art. In an exemplary variation of this process, proteins are labeled only with substantially non-fluorescent donor and acceptor moieties such that upon cleavage the intensity of fluorescence emitted from the acceptor moiety decreases. Aspects of protease cleavage assays, which can be adapted for use with the biomolecules of the present invention are also described in, e.g., Jenny et al. (2003) "A critical review of the methods for cleavage of fusion proteins with thrombin and factor Xa," *Protein Expr Purif.* 31(1): 1-11 and Funovics et al. (2003) "Protease sensors for bioimaging," *Anal Bioanal Chem.* 377(6):956-963, which are both incorporated by reference.

Figure 7:
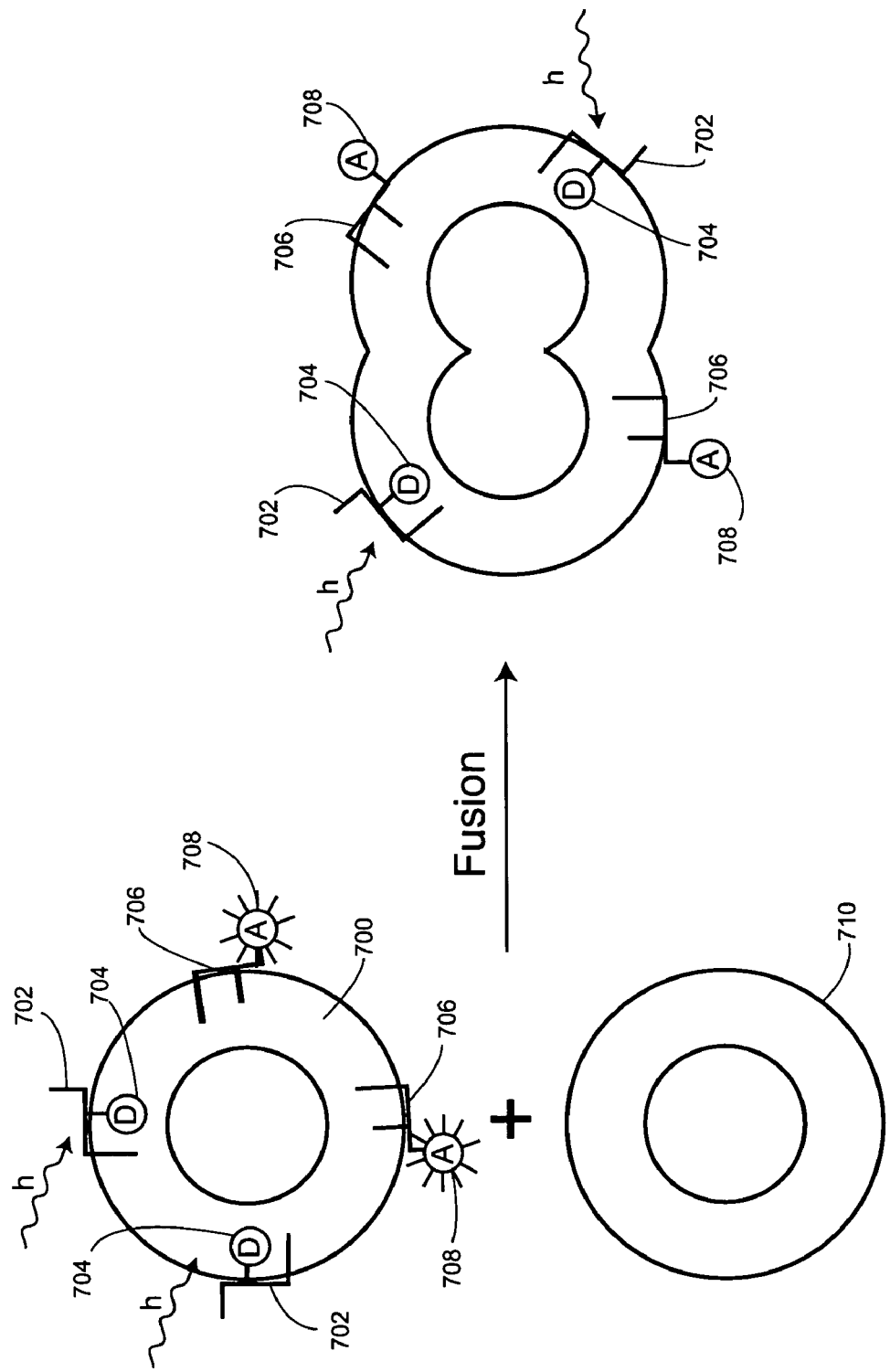
FIG. 7 schematically shows some steps performed in a lipid-mixing assay according to one embodiment of the invention.

Other representative proximity assays that can be performed using certain biomolecules of the invention, include lipid-mixing assays based on energy transfer. To illustrate, FIG. 7 schematically shows certain steps performed in a lipid-mixing assay according to one embodiment of the invention. As shown, labeled membrane 700 includes donor lipids 702 that include substantially non-fluorescent donor moieties (D) 704, and acceptor lipids 706 that include acceptor moieties (A) 708. Prior to fusing labeled membrane 700 with unlabeled membrane 710, acceptor moieties (A) 708 fluoresce in response to absorbing excitation energy transferred from substantially non-fluorescent donor moieties (D) 704, which are sufficiently proximal to acceptor moieties (A) 708 in labeled membrane 700. This fluorescence decreases once the membranes are fused as the distance between donor lipids 702 and acceptor lipids 706 increases.

Approaches to detecting fluorescence from acceptor moieties in these and other proximity assays are generally known to persons of skill in the art. Certain of these detection methods and related systems, which include the use of photomultiplier tubes, or charged coupled devices are described further below.

Figure 8:
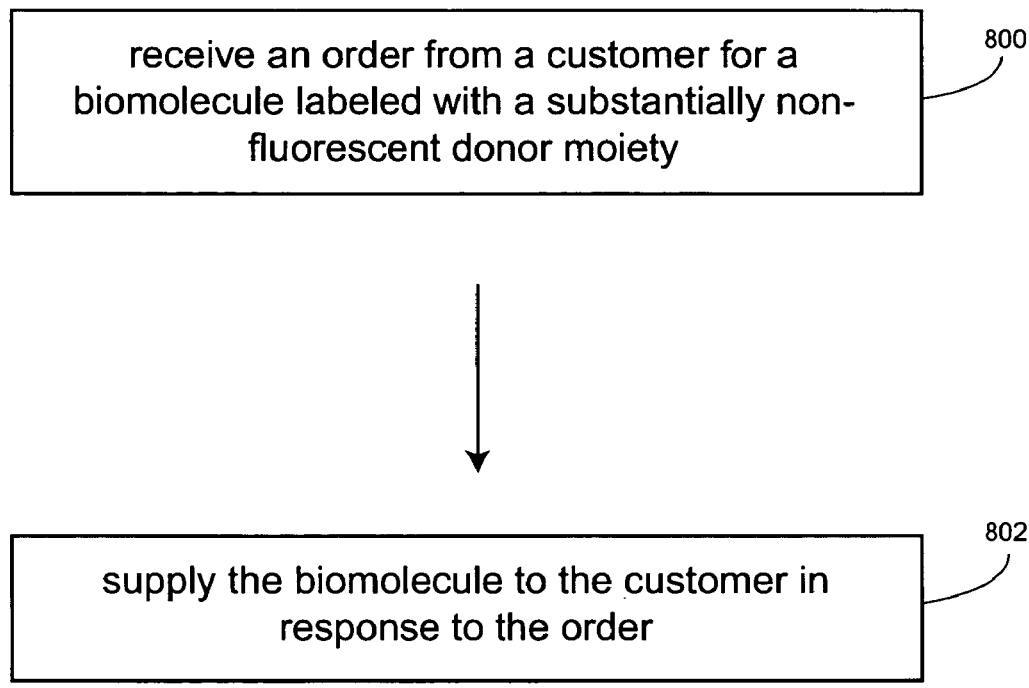
FIG. 8 is a block diagram that shows certain steps performed in a business method according to one embodiment of the invention.

In other representative embodiments, the invention provides methods of doing business that involve the biomolecules described herein. For example, FIG. 8 is a block diagram that shows certain steps performed in a business method according to one embodiment of the invention. As shown in step 800, the method includes receiving an order from a customer for at least one biomolecule as described herein. In addition, the method also includes supplying the biomolecule to the customer in response to the order (step 802). In some embodiments, for example, a business entity receives the order via a personal appearance by the customer or an agent thereof, via a postal or other delivery service (e.g., a common carrier), via a telephonic communication, via an email communication or another electronic medium, or any other suitable method. In some embodiments, the biomolecules that are ordered and/or supplied are included in the kits described herein. Furthermore, biomolecules are supplied or provided to customers (e.g., in exchange for a form of payment) by any suitable method, including via a personal appearance by the customer or an agent thereof, via a postal or other delivery service, such as a common carrier.

Systems

The invention also provides systems for detecting energy emissions from acceptor moieties in response to non-fluorescent energy transferred from substantially non-fluorescent donor moieties. The systems can be used to perform many different assays, including the proximity assays referred to herein. The systems include one or more biomolecules labeled at least with one or more substantially non-fluorescent donor moieties. In certain embodiments, the biomolecules are arrayed on solid supports, whereas in others, they are provided in one or more containers, e.g., for assays performed in solution. The systems also include radiation sources and at least one detector or detection component (e.g., a spectrometer) that at least detects energy emitted from acceptor moieties when the acceptor moieties are sufficiently proximal to the substantially non-fluorescent donor moieties. In addition, the systems also optionally include at least one thermal modulator (e.g., a thermal cycling device) operably connected to the containers or solid supports to modulate temperature in the containers or on the solid supports, and/or at least one fluid transfer component (e.g., an automated pipettor) that transfers fluid to and/or from the containers or solid supports, e.g., for performing one or more proximity assays in the containers or on the solid supports.

Detectors are typically structured to detect detectable signals produced, e.g., in or proximal to another component of the given assay system (e.g., in a container and/or on a solid support). Suitable signal detectors that are optionally utilized, or adapted for use, herein detect, e.g., fluorescence, phosphorescence, radioactivity, absorbance, refractive index, luminescence, or mass. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, or scanning detectors. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, and photometers. Detectors are also described in, e.g., Skoog et al., *Principles of Instrumental Analysis*, 5$^{th}$ Ed., Harcourt Brace College Publishers (1998), Currell, *Analytical Instrumentation: Performance Characteristics and Quality*, John Wiley & Sons, Inc. (2000), Sharma et al., *Introduction to Fluorescence Spectroscopy*, John Wiley & Sons, Inc. (1999), Valeur, *Molecular Fluorescence: Principles and Applications*, John Wiley & Sons, Inc. (2002), and Gore, *Spectrophotometry and Spectrofluorimetry: A Practical Approach*, 2$^{nd}$ Ed., Oxford University Press (2000), which are each incorporated by reference.

The systems of the invention also typically include controllers that are operably connected to one or more components (e.g., detectors, thermal modulators, and/or fluid transfer components) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers. Controllers and/or other system components are optionally coupled to an appropriately programmed processor, computer, digital device, information appliance, or other logic device (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display or liquid crystal display), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales.

Figure 9:
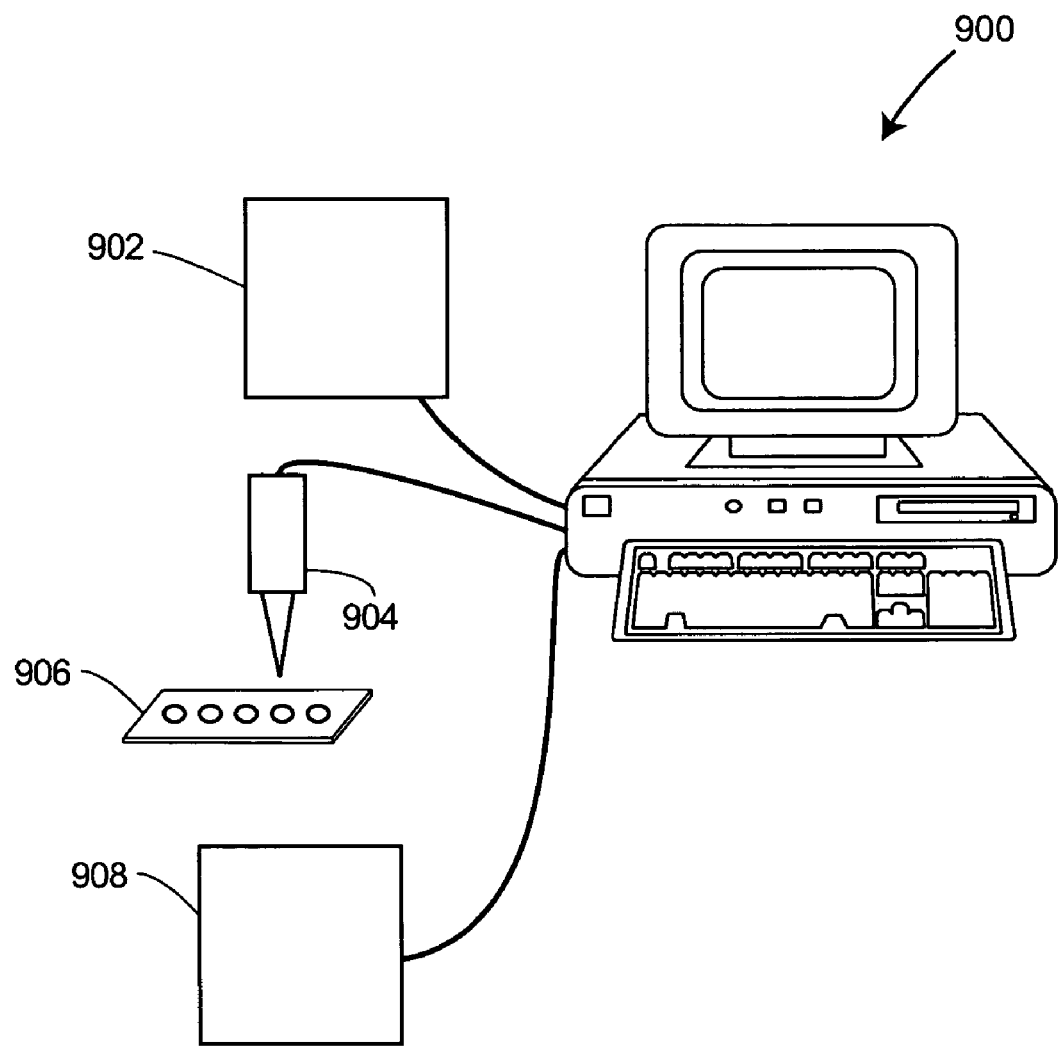
FIG. 9 is a block diagram showing a representative system for performing proximity assays.

FIG. 9 is a schematic showing a representative system that includes a logic device in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform as desired. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

More specifically, FIG. 9 schematically illustrates computer 900 to which detector 902 (e.g., a spectrometer, such as a spectrofluorometer), fluid transfer component 904, and thermal modulator 908 are operably connected. Optionally, one or more of these components are operably connected to computer 900 via a server (not shown in FIG. 9). During operation, fluid transfer component 904 typically transfers reaction mixtures or components thereof to multi-well container 906. Thermal modulation (e.g., thermal cycling) is typically effected by thermal modulator 908, which thermally communicates with multi-well container 906. Detector 902 typically detects detectable signals (e.g., fluorescent emissions) produced prior to, during, and/or after a given proximity assay is performed in the system. It will be apparent to one of skill in the art that one or more components of the system schematically depicted in FIG. 9 are optionally fabricated integral with one another (e.g., in the same housing).

Kits

The reaction mixtures or components thereof (e.g., biomolecules) employed in the methods of the present invention are optionally packaged into kits. In certain embodiments, different biomolecules included in kits are labeled with spectrally resolvable acceptor moieties, e.g., to perform certain multiplexing applications using these kits. In some embodiments of these kits, only one type of suitable substantially non-fluorescent donor moiety is included so that only a single energy source is needed to excite each of the different acceptor moieties.

In addition, the kits may also include suitably packaged reagents and materials used to perform biopolymer synthesis, nucleic acid sequencing reactions, real-time monitoring of nucleic acid amplification or other proximity assays, such as buffers, enzymes, standards or controls, salts, metal ions, primers, probes, extendible nucleotides, terminator nucleotides, glycerol, dimethyl sulfoxide, and/or poly rA. as well as instructions for conducting a particular process or assay. In some of these embodiments, the kits further include at least one pyrophosphatase (e.g., a thermostable pyrophosphatase), e.g., for use in minimizing pyrophosphorolysis, and/or uracil N-glycosylase (UNG) and optionally dUTP, e.g., for use in applications where protection against carry-over contamination is desirable. Kit components, such as biomolecules are typically provided in one or more containers.

To further illustrate, the kits of the invention include many different embodiments for performing a wide variety of assays and/or synthesis reactions. Some of these applications are also described above. In some embodiments, for example, kits include immunoglobulins labeled as described herein and instructions for detecting the binding of the immunoglobulins to target epitopes as part of a given immunoassay. Optionally, kits include labeled lipids and instructions for performing a particular proximity assay using the lipid, such as a membrane fusion assay. In certain embodiments, kits include primers and instructions for extending the primers, e.g., in nucleic acid sequencing reactions or nucleic acid amplification reactions. In these embodiments, the primers and/or optionally included extendible nucleotides, terminator nucleotides (e.g., dideoxycytosine triphosphate, dideoxyadenosine triphosphate, dideoxyguanosine triphosphate, and dideoxythymidine triphosphate), and/or probes (e.g., hybridization probes, 5'-nuclease probes, and hairpin probes) are typically labeled as described herein. In some other exemplary embodiments, kits include biopolymer synthesis reagents (e.g., polypeptide synthesis reagents or nucleic acid synthesis reagents) and instructions for synthesizing biopolymers using these reagents.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example I

Comparisons of Detected Fluorescence

Figure 10:
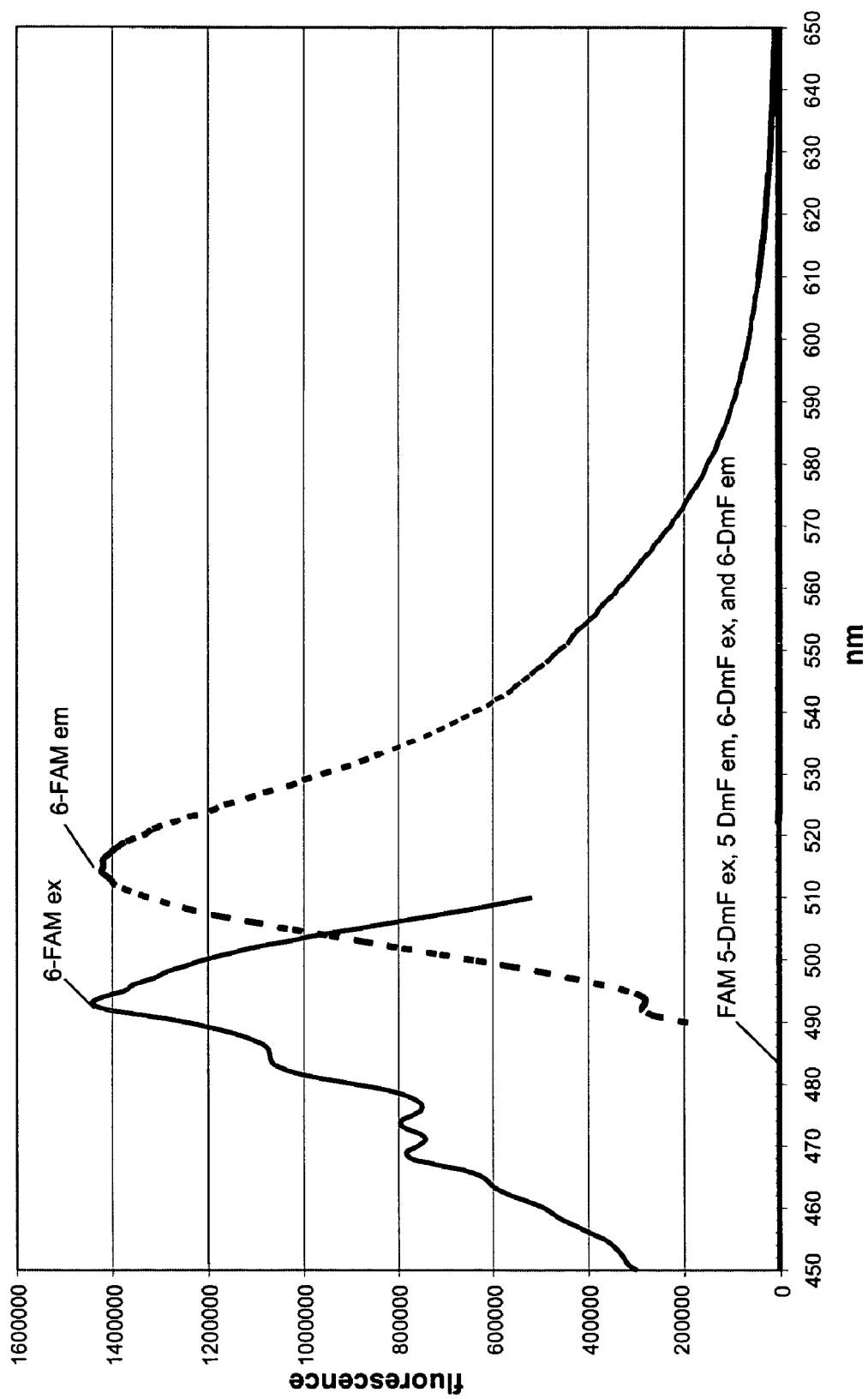
FIG. 10 is a plot of overlaid spectra obtained from oligonucleotides labeled with 6-carboxyfluorescein (or 6-FAM), 4',5'-dimethoxy-5-carboxyfluorescein (or 5-DmF), or 4',5'-dimethoxy-6-carboxyfluorescein (or 6-DmF).
Figure 11:
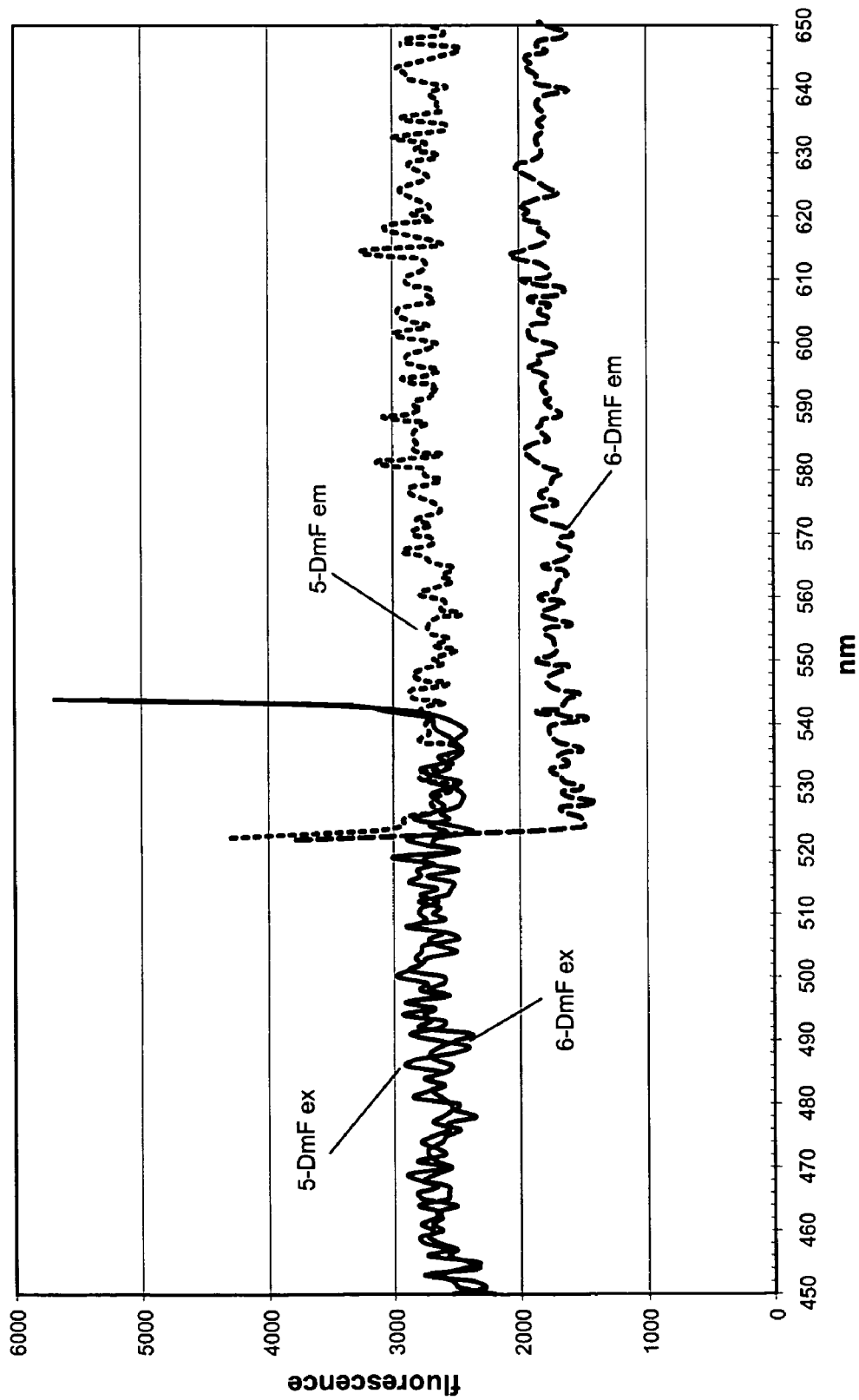
FIG. 11 is a detailed excerpt from the graph depicted in FIG. 10 that shows the overlaid spectra obtained from the excitation and emission scans of oligonucleotides labeled with 5-DmF or 6-DmF.

This example shows fluorescent emissions that were separately detected from oligonucleotides labeled with fluorescent moieties and oligonucleotides labeled with substantially non-fluorescent moieties in different samples. In particular, FIG. 10 is a graph of overlaid spectra obtained from excitation and emission scans of oligonucleotides labeled with 6-carboxyfluorescein (6-FAM), 4',5'-dimethoxy-5-carboxyfluorescein (5-DmF), or 4',5'-dimethoxy-6-carboxyfluorescein (6-DmF). The ordinate of the graph shown in FIG. 10 represents absolute fluorescence, while the abscissa represents wavelength (nm). As shown, the plot for an excitation scan of 6-FAM labeled oligonucleotides obtained at 515 nm is labeled "6-FAM ex", whereas the plot for an emission scan of 6-FAM labeled oligonucleotides obtained at 493 nm is labeled "6-FAM em". The plot for an excitation scan of 5-DmF labeled oligonucleotides obtained at 545 nm is labeled "5-DmF ex", whereas the plot for an emission scan of 5-DmF labeled oligonucleotides obtained at 520 nm is labeled "5-DmF em". The plot for an excitation scan of 6-DmF labeled oligonucleotides obtained at 545 nm is labeled "6-DmF ex", whereas the plot for an emission scan of 6-DmF labeled oligonucleotides obtained at 520 nm is labeled "6-DmF em". To further illustrate, FIG. 11 is a detailed excerpt from the graph depicted in FIG. 10 that shows the overlaid spectra obtained from the excitation and emission scans of the 5-DmF and 6-DmF labeled oligonucleotides, respectively. The concentration of labeled nucleotides in each of the respective scanned samples was 0.15 µM.

Example II

Synthesis of Biopolymer Synthesis Reagents

Figure 12:
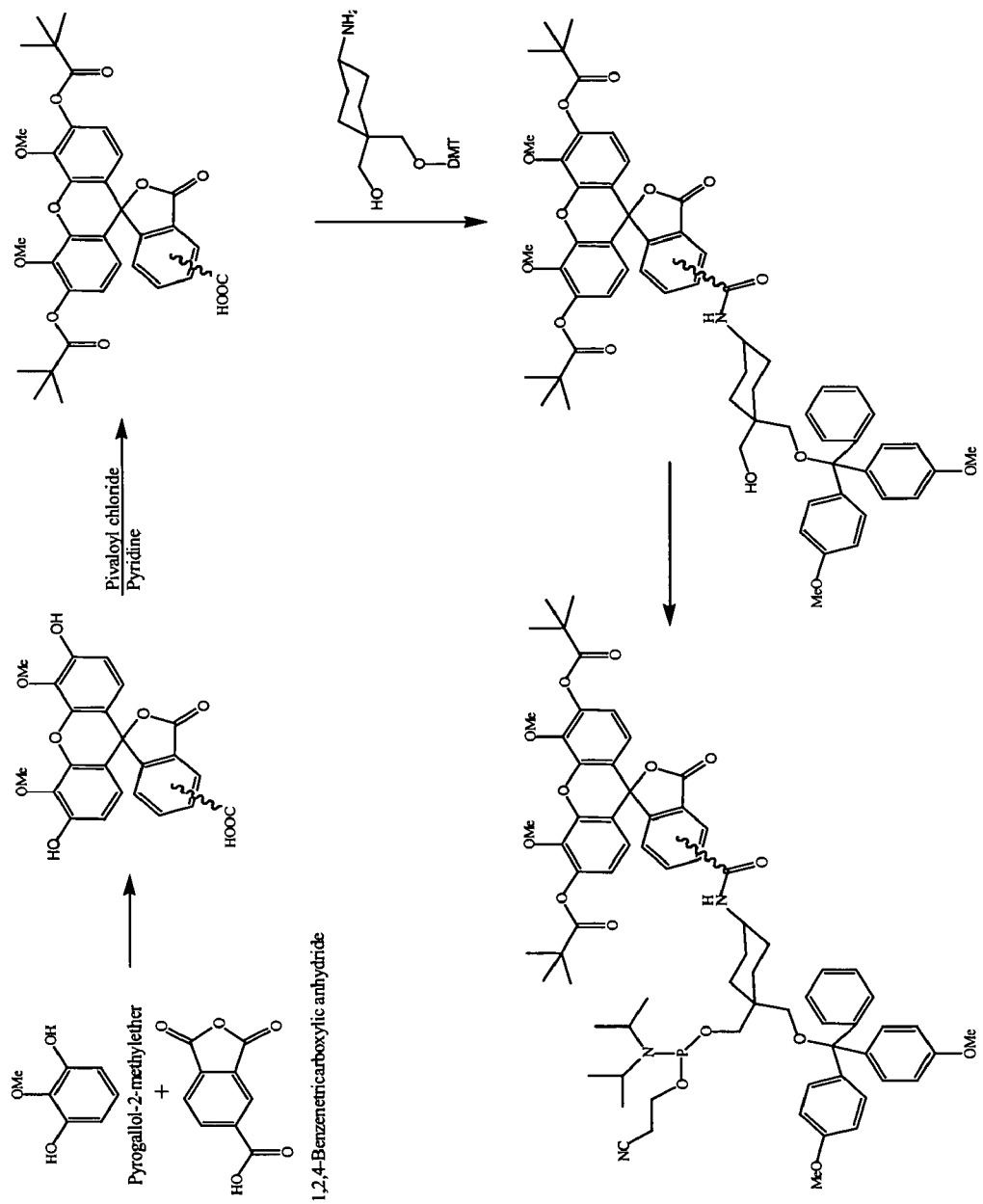
FIG. 12 schematically illustrates certain steps in a synthetic scheme of 5- and 6-DmF-DMT-CX-Linker-phosphoramidites according to one embodiment of the invention.

This example describes a representative synthesis pathway for biopolymer synthesis reagents that comprise substantially non-fluorescent donor moieties. In particular, synthetic schemes for 5- and 6-dimethoxyfluorescein-DMT-CX-Linker-phosphoramidites are described in this example according to one embodiment of the invention. As an overview, FIG. 12 schematically illustrates certain steps in this synthetic scheme.

Synthesis of 5 and 6-Dimethoxyfluorescein (DmF) Isomers

Figure 13:
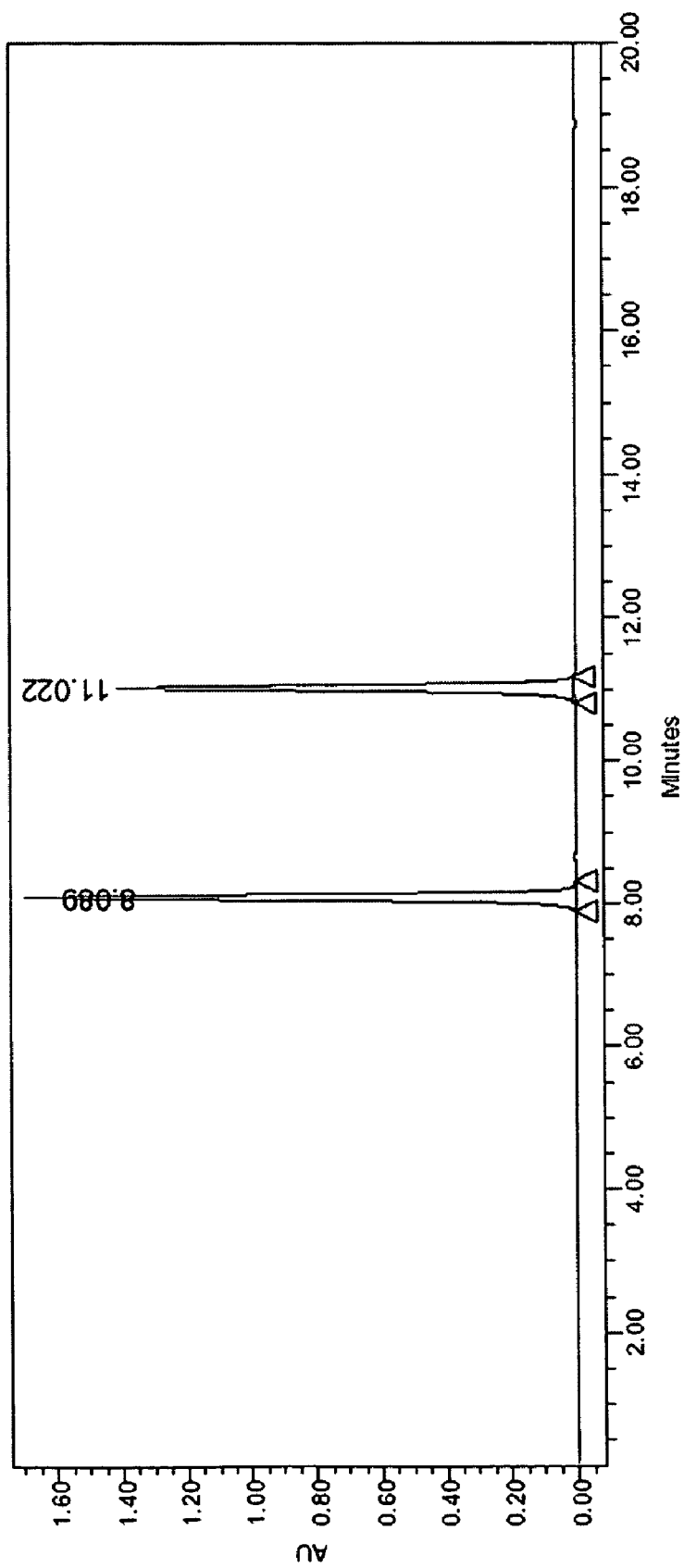
FIG. 13 is a high performance liquid chromatography (HPLC) trace that shows the detection of 5-DmF and 6-DmF.

The synthesis of DmF was performed according to the procedure of U.S. Pat. No. 4,318,846, entitled "NOVEL ETHER SUBSTITUTED FLUORESCEIN POLYAMINO ACID COMPOUNDS AS FLUORESCERS AND QUENCHERS," issued Mar. 9, 1982 to Khanna et al. After the work-up, the product was purified by column chromatography. As shown in FIG. 13 (ordinate represents absorbance units, abscissa represents retention time (minutes)), the HPLC analysis of purified DmF showed two peaks due to positional isomers, as expected. These positional isomers were attributed to 5-DmF and 6-DmF. Further, the identity of these compounds was established by mass spectroscopy data.

Pivalation of 5- and 6-DmF Isomers

Figure 14:
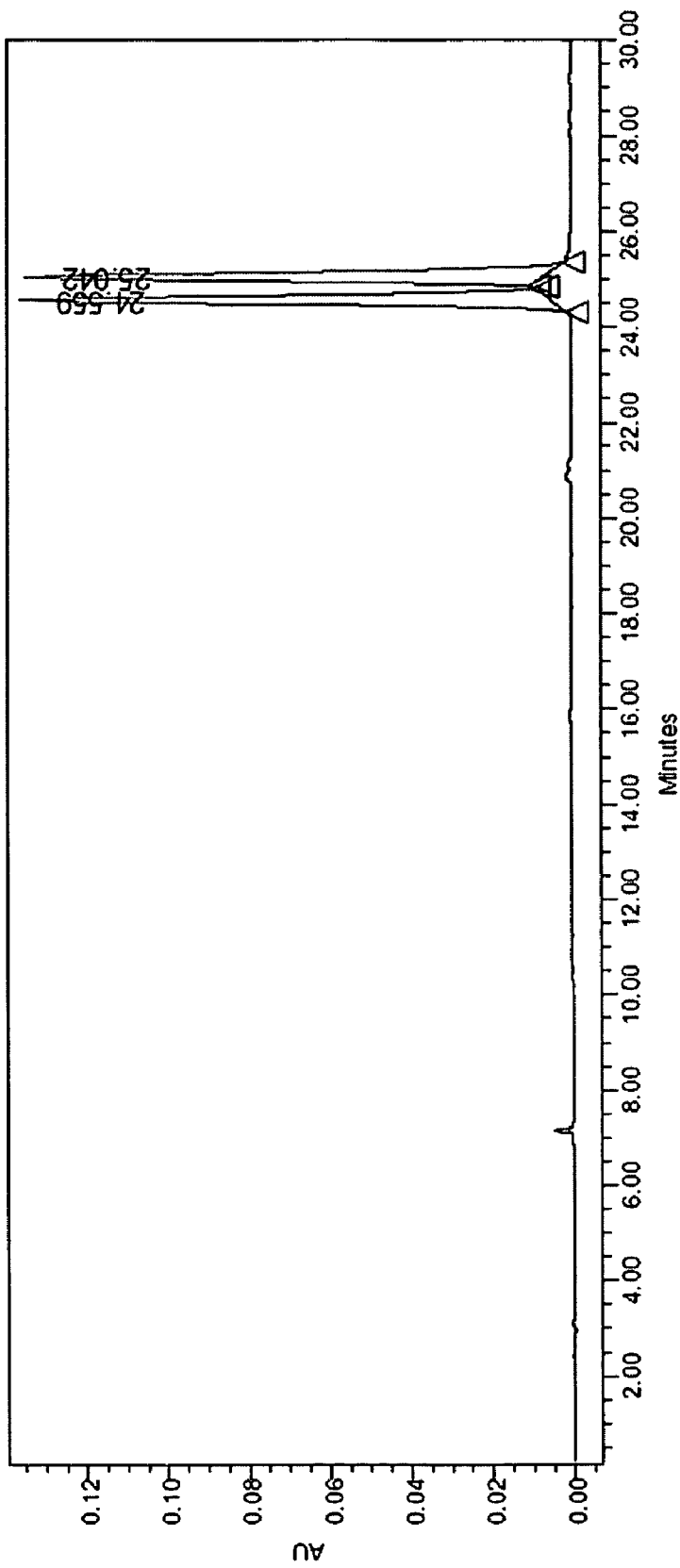
FIG. 14 is an HPLC trace that shows the detection of pivaloyl 5-DmF and pivaloyl 6-DmF.

To the solution of DmF (200 mg, 0.46 mmol) in pyridine (5 ml) was added N,N-diisopropylethylamine (3.0 ml). Then, the reaction mixture was cooled in an ice-cold water bath for 20 minutes. To this reaction mixture was added pivaloyl chloride (500 mg, 4.15 mmol) in a drop-wise fashion. After the addition, the reaction mixture was stirred under cooling conditions for additional 5 minutes. The cooling bath was then removed and the reaction mixture was stirred at room temperature overnight. The solvent was removed under reduced pressure and then purified by column chromatography. See, FIG. 14, which is an HPLC trace that shows the detection of pivaloyl 5-DmF and pivaloyl 6-DmF (ordinate represents absorbance units, abscissa represents retention time (minutes)). The identity of these compounds was confirmed by mass spectral analysis.

Pivaloyl-5- and -6-DmF-DMT-CX-Linker

Figure 15:
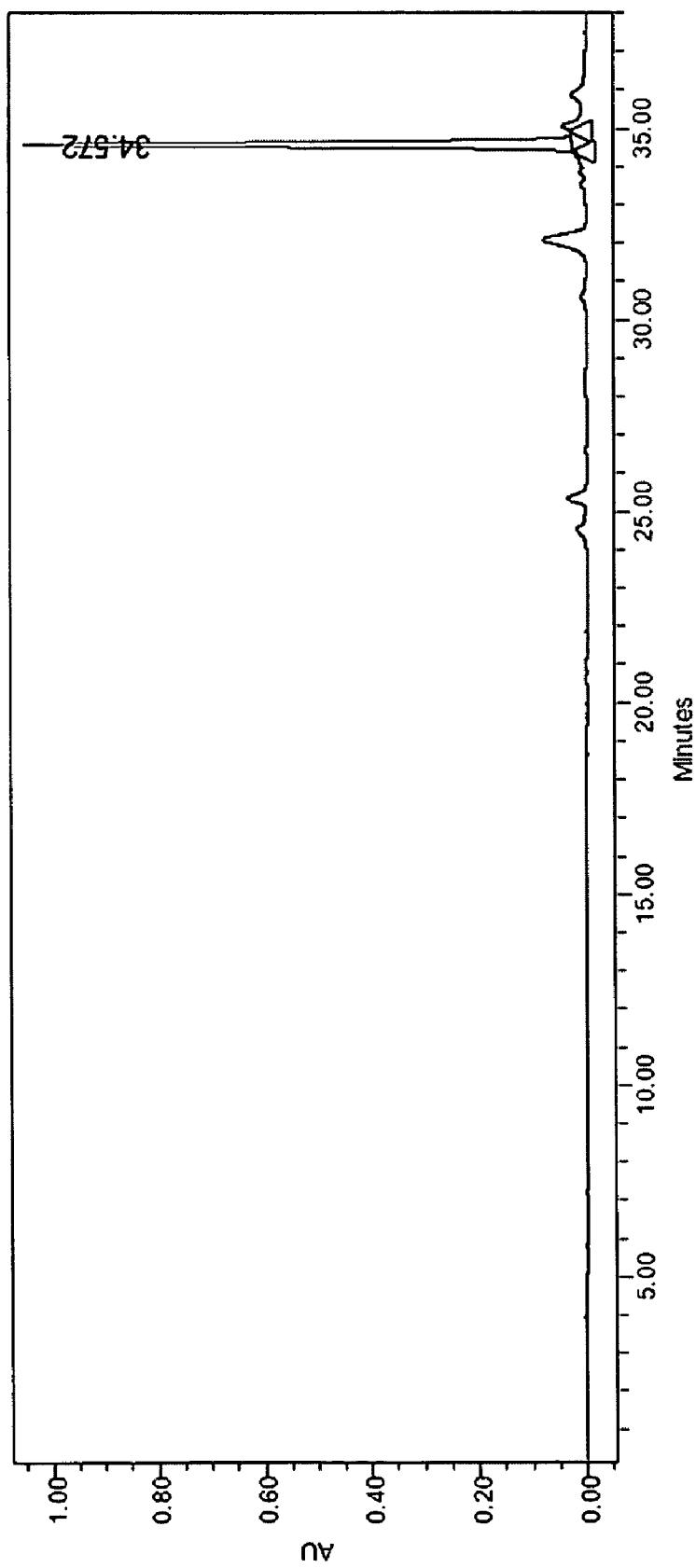
FIG. 15 is an HPLC trace that shows the detection of pivalated DmF+CX-Linker.
Figure 16:
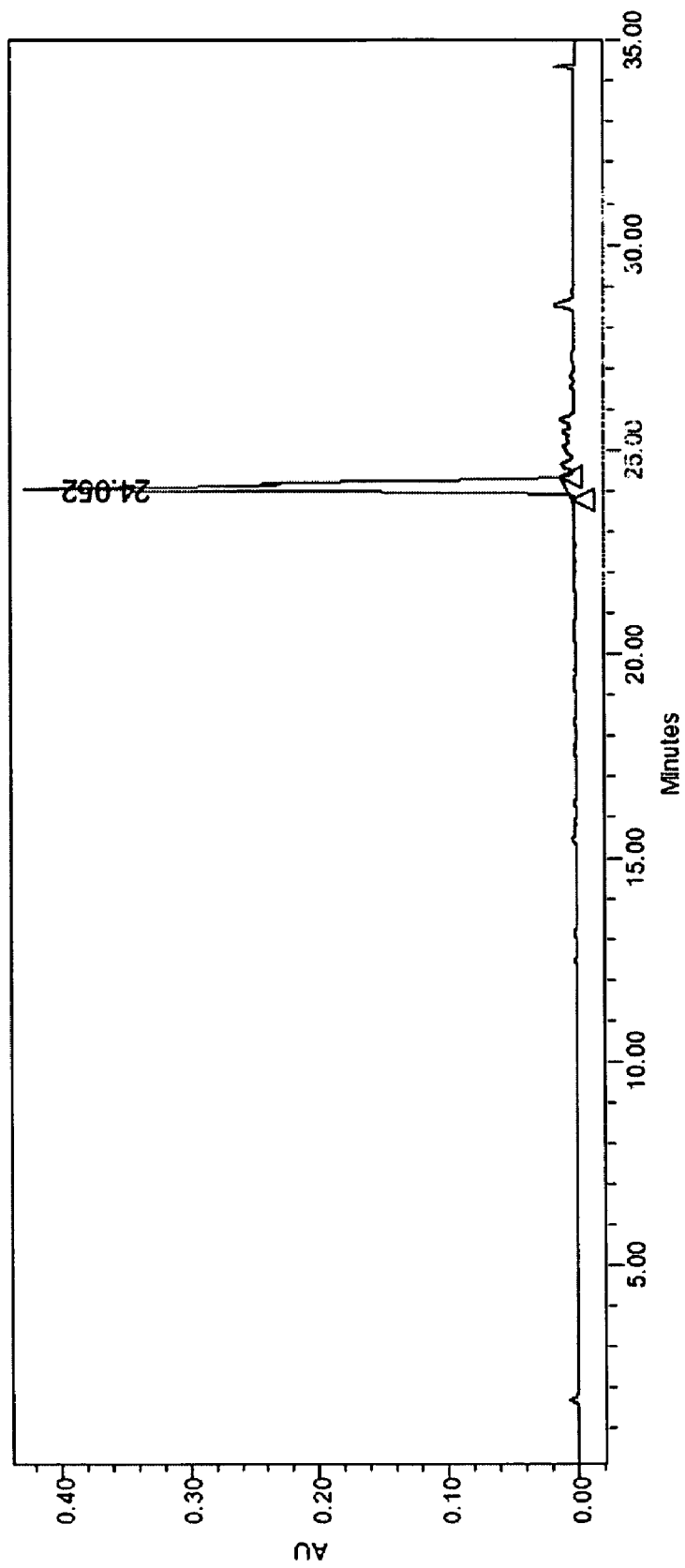
FIG. 16 is an HPLC trace that shows the detection of DmF–CX-Linker.

To the solution of pivaloyl DmF (220 mg) and DMT-CX-linker (195 mg, prepared in Roche, Penzberg) in DMSO (2 ml), dimethylformamide (3 ml) was added HBTU (3 ml) under cooling conditions. Approximately 5 minutes later diisopropylethylamine (0.4 ml) was added and the stirring was continued for 3 hours under cooling conditions (0-5° C., bath temperature). As shown in FIG. 15 (ordinate represents absorbance units, abscissa represents retention time (minutes)), no starting material was observed after 3 hours. Solvents in the reaction mixture (DMF and DMSO) were removed under high vacuum. The product was purified by column chromatography (see, the HPLC chromatogram of FIG. 16 (ordinate represents absorbance units, abscissa represents retention time (minutes))) and confirmed by mass spectral analysis. The isolated yield was 84% (320 mg).

5 and 6-DmF-DMT-CX-Linker-Phosphoramidite

Figure 17:
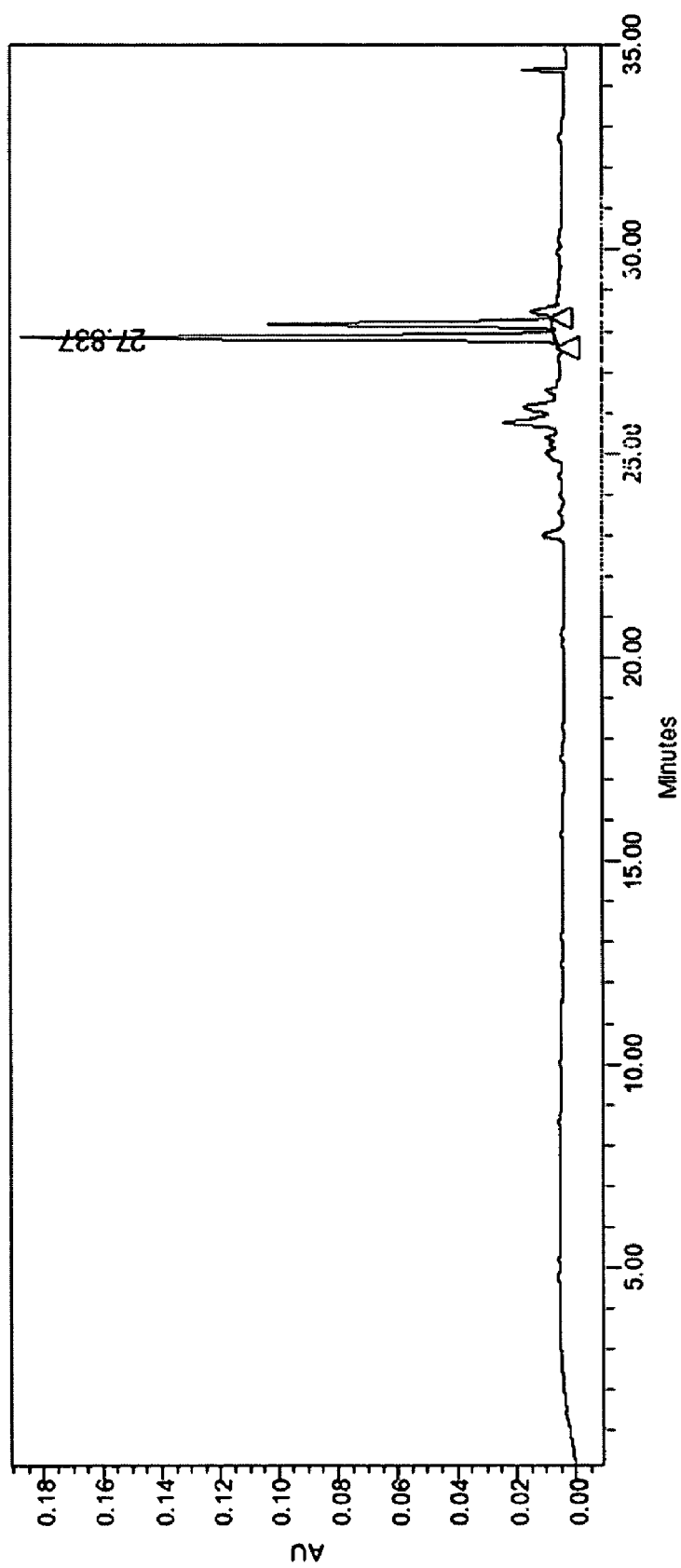
FIG. 17 is an HPLC trace that shows the detection of DmF–CX-Linker-phosphoramidite.
Figure 18:
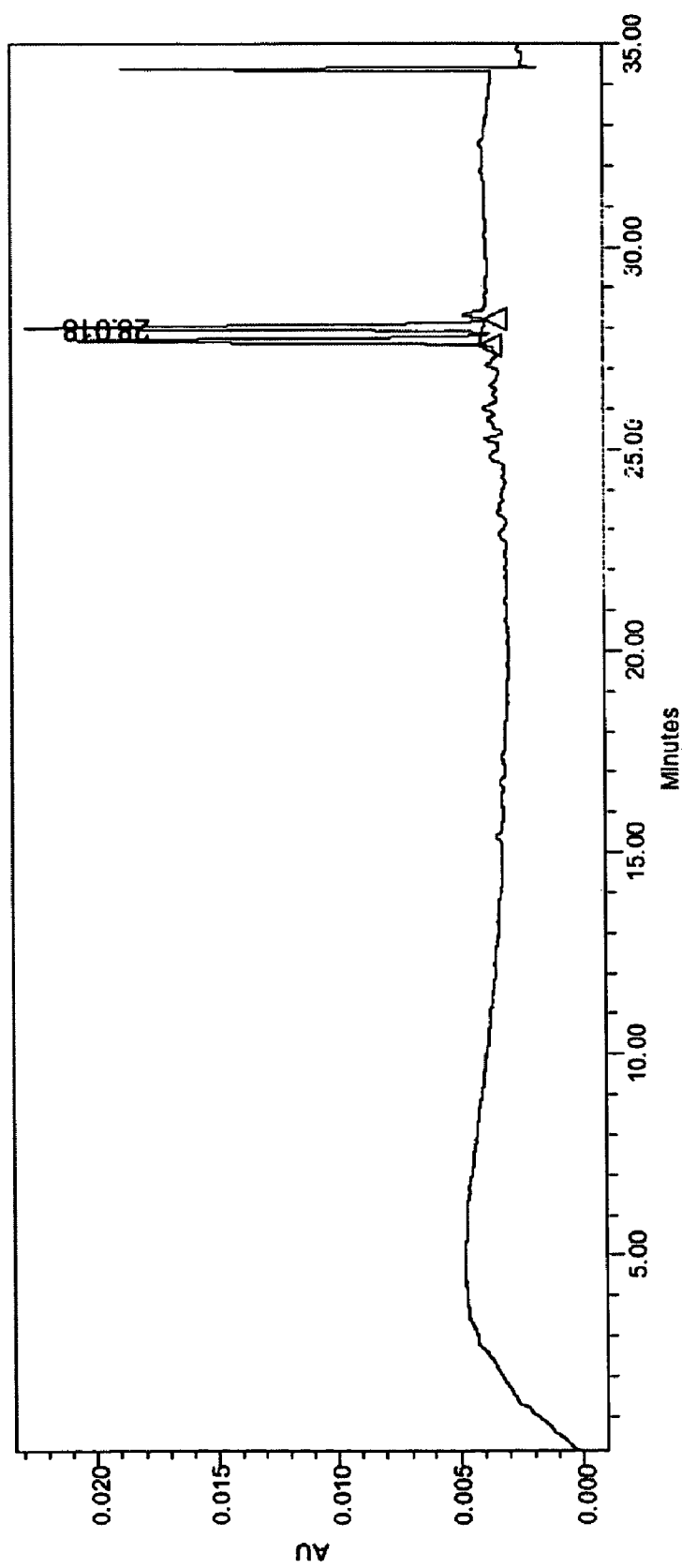
FIG. 18 is an HPLC trace that shows the detection of DmF–CX-Linker-phosphoramidite.
Figure 19:
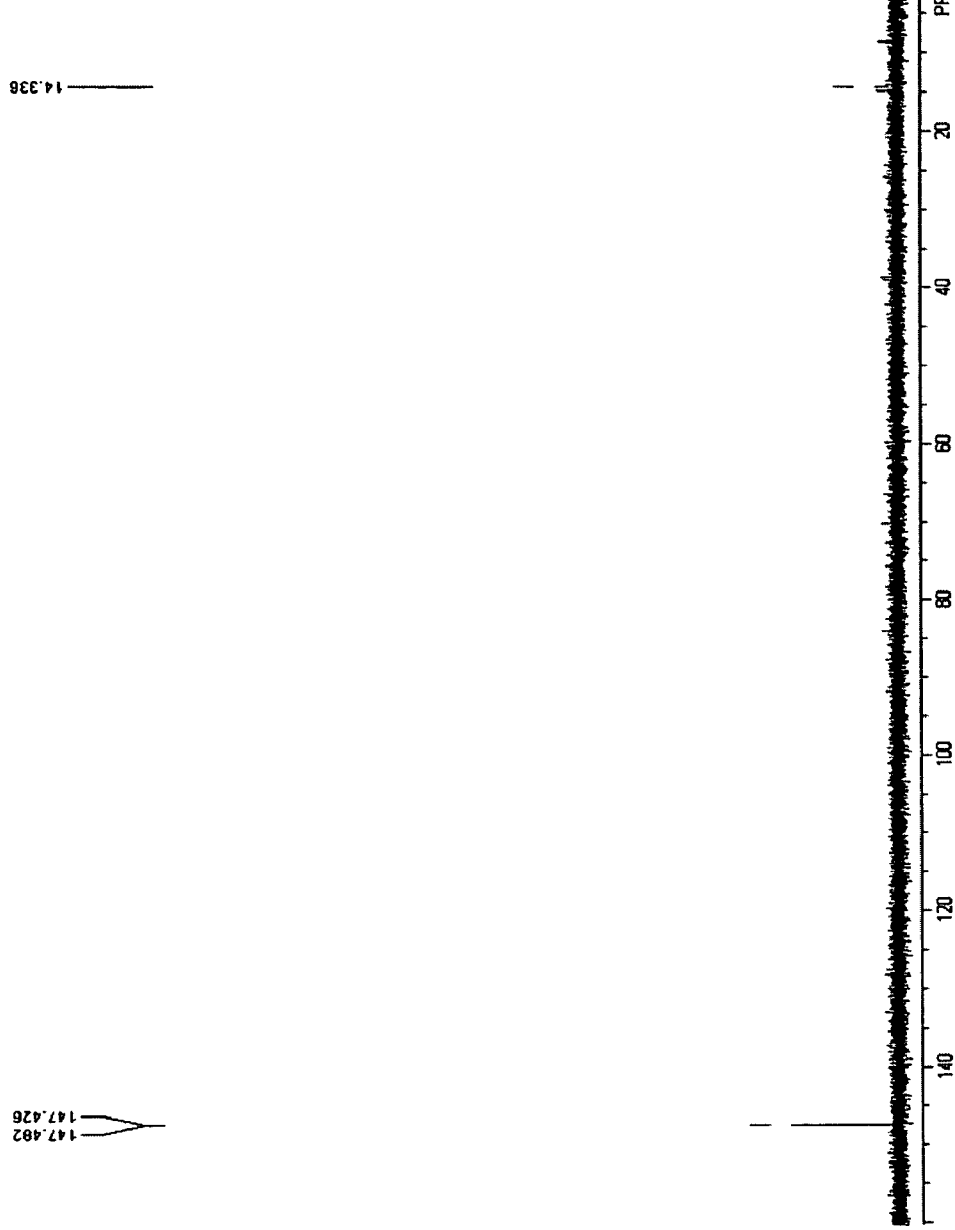
FIG. 19 is a $^{31}$P NMR spectrum that shows the detection of DmF–CX-Linker-phosphoramidites.

To the solution of pivaloyl-DmF-DMT-CX-Linker (100 mg, 0.095 mmol) in dichloromethane (6 ml) at room temperature was added diisopropylethylamine (300 mg, 0.84 mmol) and the reaction mixture cooled to 5° C. (bath temperature) in ice cold water. To the reaction mixture was added cyanoethyl diisopropylchlorophosphoramidite reagent (28 mg, 0.12 mmol) and stirring was continued at 5° C. After one hour, an additional cyanoethyl diisopropylchlorophosphoramidite (28 mg, 0.12 mmol) reagent was added and the reaction mixture was left at 0° C. for additional 16 hours. FIG. 17 is an HPLC trace that shows the detection of the product after this 16-hour period. As shown in FIG. 18 (ordinate represents absorbance units, abscissa represents retention time (minutes)), the HPLC analysis of the reaction mixture, after 18 hours, showed no starting material and the appearance of a new peak at 28 minutes. The product was purified by flash column chromatography (isolated yield 100 mg, 80%) and confirmed by mass spectral analysis and $^{31}$P NMR analysis (see, FIG. 19).

Separation of Dimethoxyfluorescein Isomers by Chromatography

Figure 20:
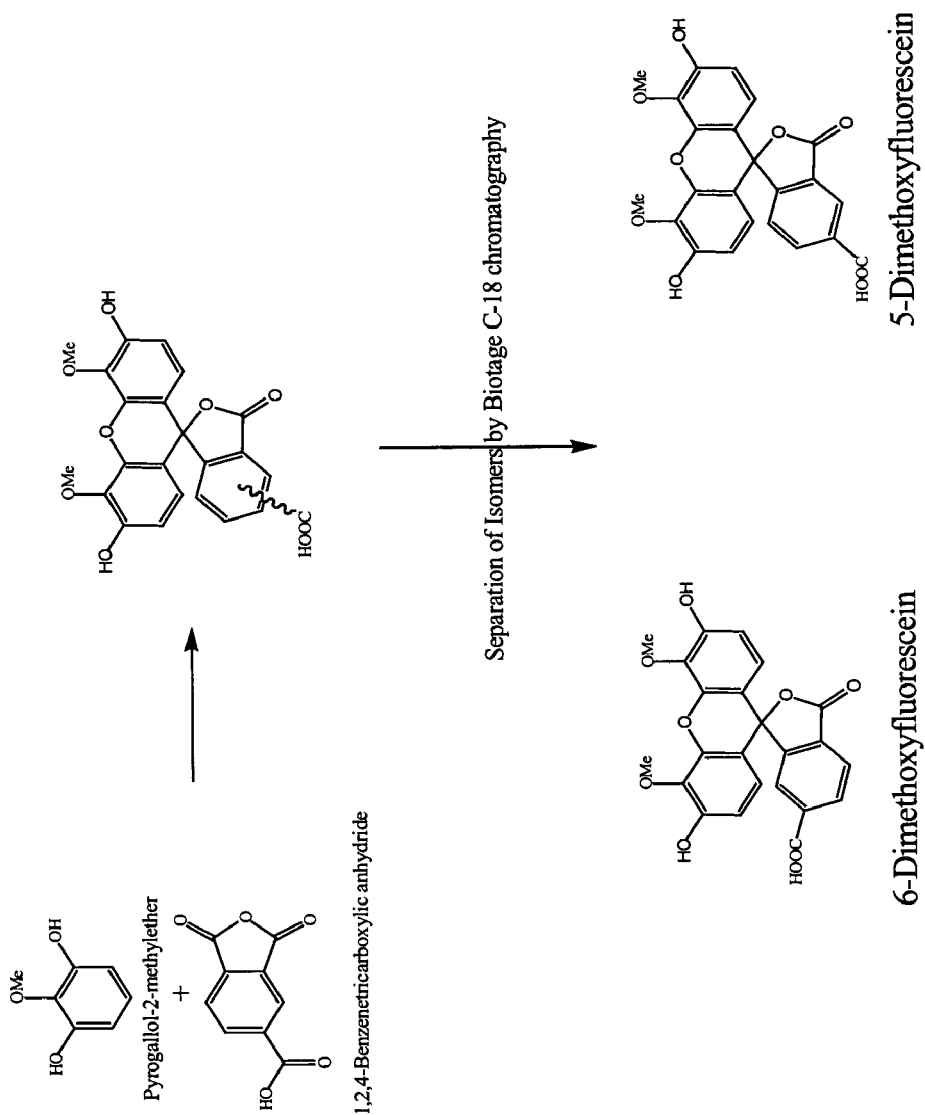
FIG. 20 schematically illustrates certain steps in a purification scheme to separate 5- and 6-DmF isomers from one another according to one embodiment of the invention.
Figure 21:
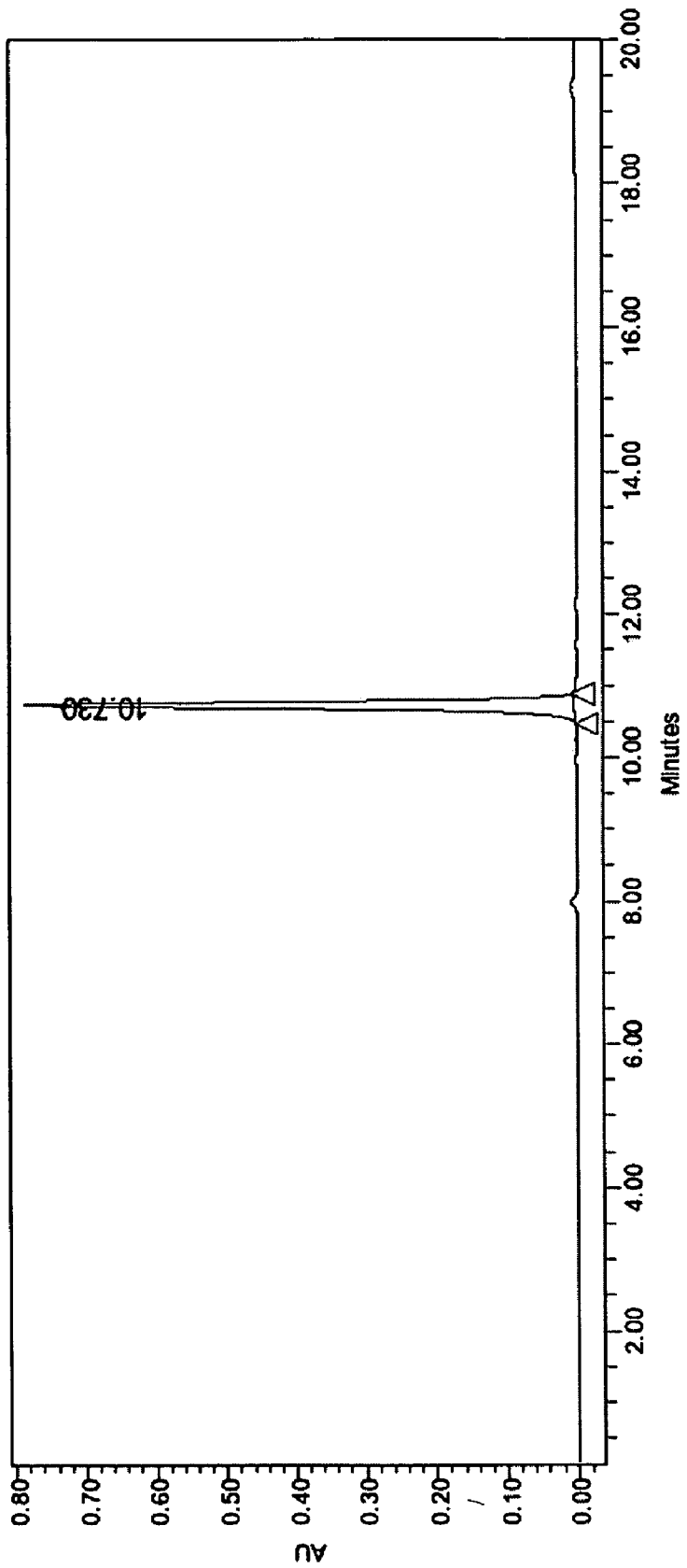
FIG. 21 is a chromatogram that shows the detection of 5-DmF.
Figure 22:
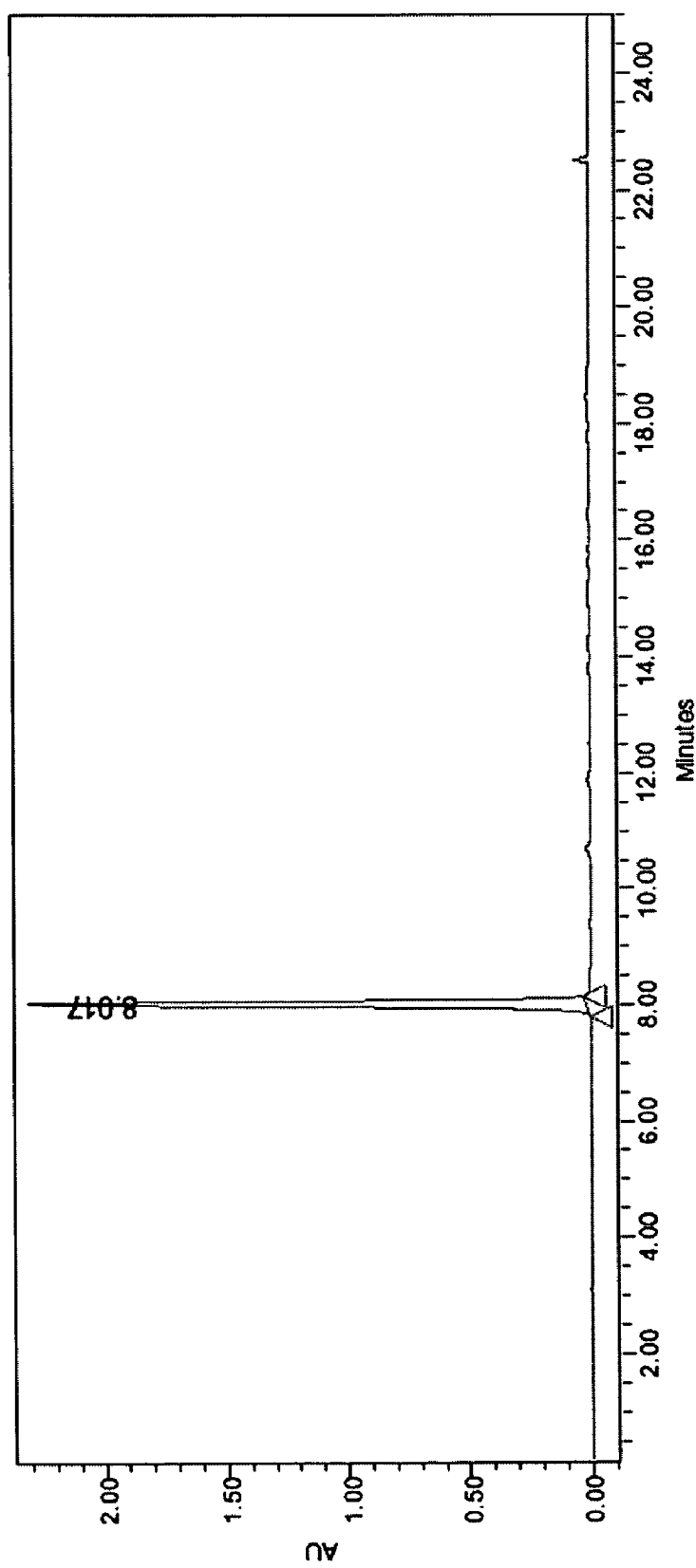
FIG. 22 is a chromatogram that shows the detection of 6-DmF.

FIG. 20 schematically illustrates certain steps in a purification scheme that was used to separate 5- and 6-dimethoxyfluorescein isomers from one another. More specifically, the separation of DmF isomers was achieved by flash column chromatography using Biotage C-18 column and 0.1 M TEAA—acetonitrile as an elution buffer. FIGS. 21 and 22 are chromatograms that show the detection of 5-DmF and 6-DmF, respectively (ordinates represent absorbance units, abscissas represent retention time (minutes)). The fractions corresponding to 5-DmF and the fractions corresponding to 6-DmF were pooled separately and then lyophilized. These isomers were further confirmed by 1H NMR data [(NMR Data of 5-DmF: δ 8.34 (1H, s, Ar), 8.25 (1H, d, Ar), 7.24 (1H, d, Ar), 6.63 (2H, Ar), 6.30 (2H, d, Ar), 3.95 (6H, s, OMe)) and NMR Data of 6-DmF: δ 8.13 (1H, d, Ar), 7.89 (1H, d, Ar), 7.56 (1H, s, Ar), 6.63 (2H, d, Ar), 6.29 (2H, d, Ar), 3.95 (6H, s, OMe)].

Synthesis of 6-Dimethoxyfluorescein-DMT-CX-Linker-Phosphoramidite

Figure 23:
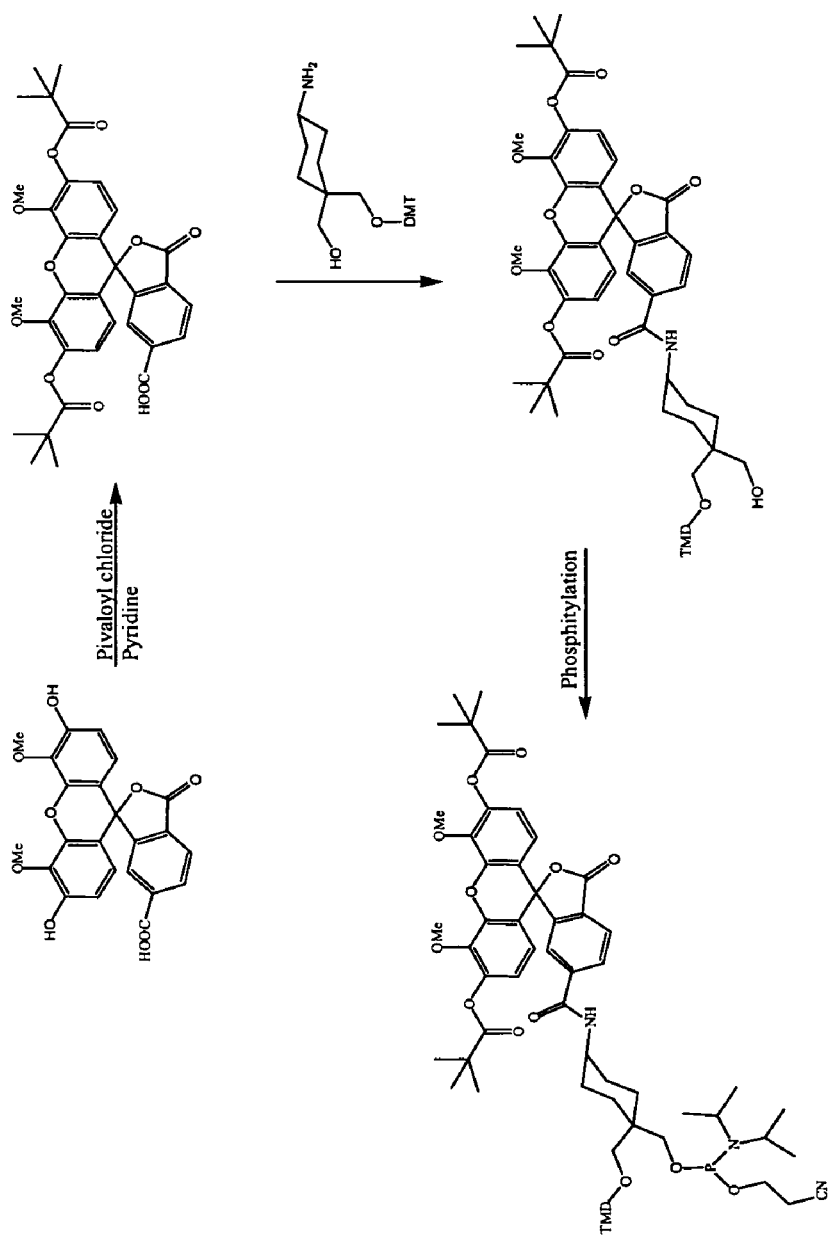
FIG. 23 schematically illustrates certain steps in a synthetic scheme of 6-DmF-DMT-CX-Linker-phosphoramidites according to one embodiment of the invention.
Figure 24:
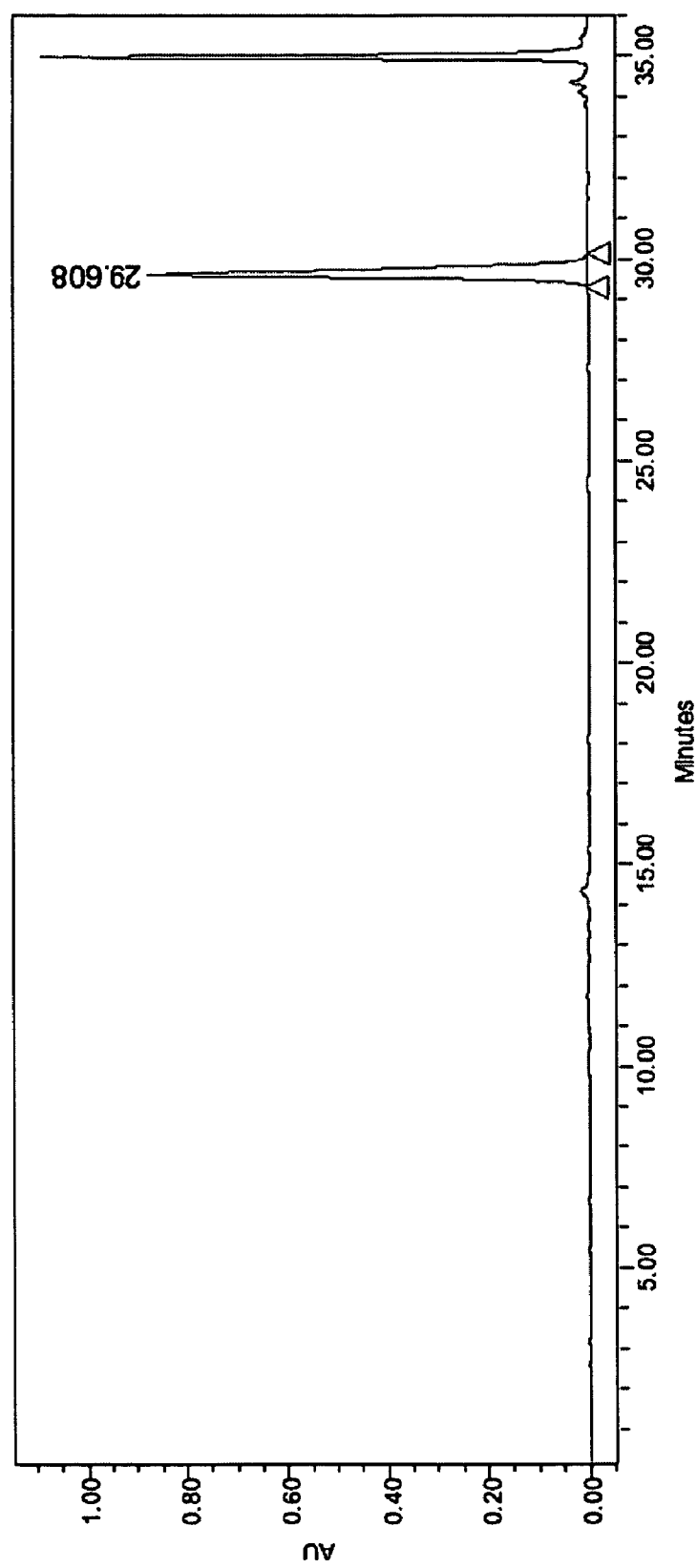
FIG. 24 is an HPLC trace that shows the detection of pivalated 6-DmF.
Figure 25:
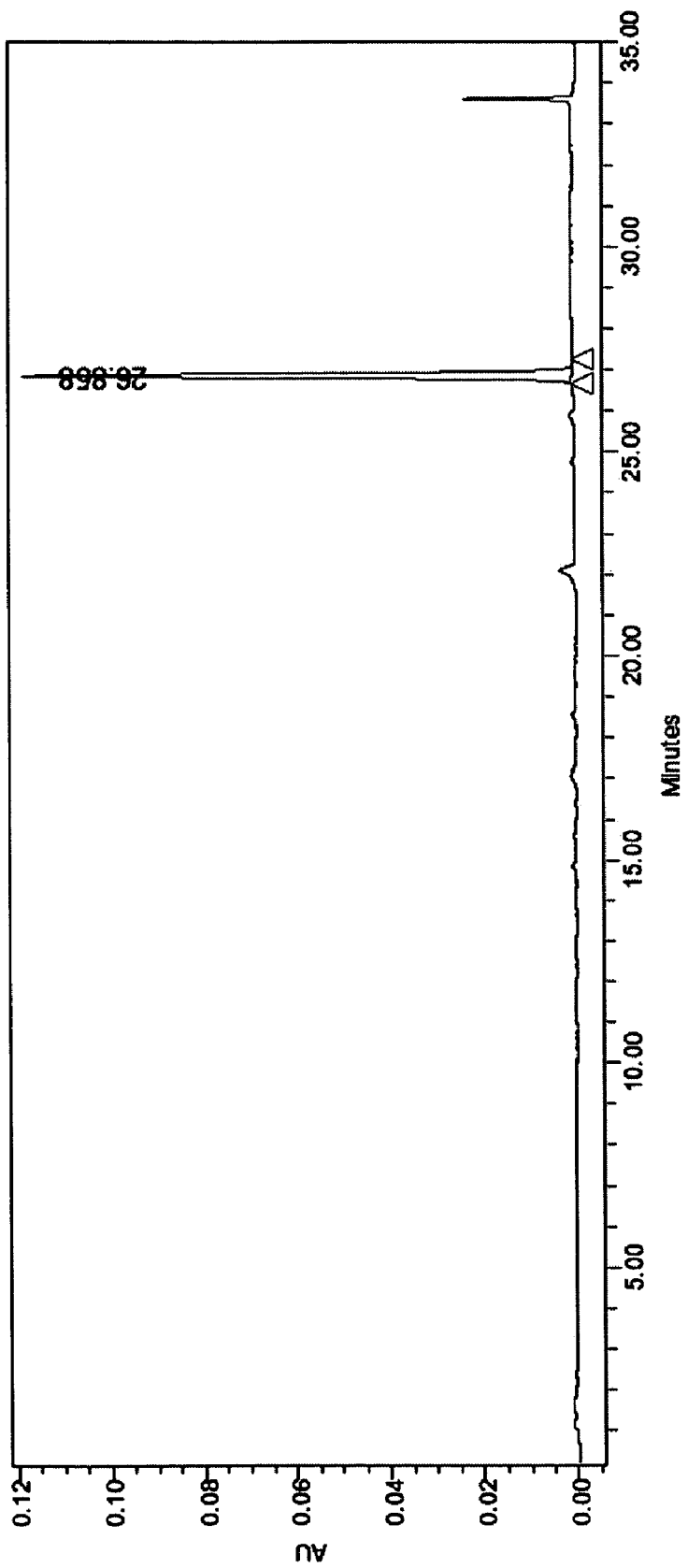
FIG. 25 is an HPLC trace that shows the detection of 6-DmF–CX-linker.
Figure 26:
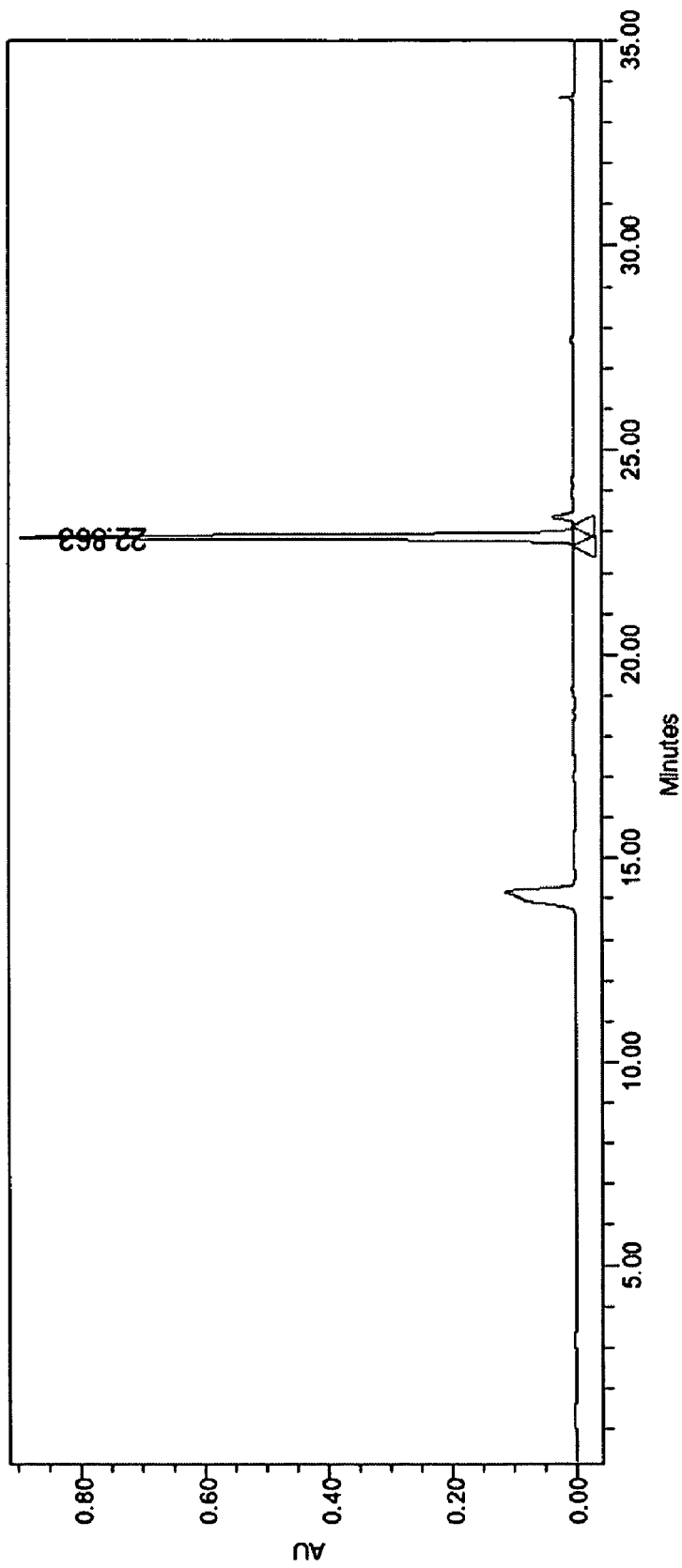
FIG. 26 is an HPLC trace that shows the detection of 6-DmF–CX-linker-phosphoramidite.

The methods for the synthesis of 6-DmF-DMT-CX-linker-phosphoramidite are identical to the methods, described above, for 5- and 6-DmF-DMT-CX-linker-phosphoramidites. In particular, FIG. 23 schematically illustrates certain steps in this synthetic scheme. In addition, FIGS. 24-26 are HPLC traces that show the detection of pivalated 6-DmF, 6-DmF–CX-linker, and 6-DmF–CX-linker-phosphoramidite, respectively (ordinates represent absorbance units, abscissas represent retention time (minutes)).

Synthesis of 5-Dimethoxyfluorescein-DMT-CX-Linker-Phosphoramidite

Figure 27:
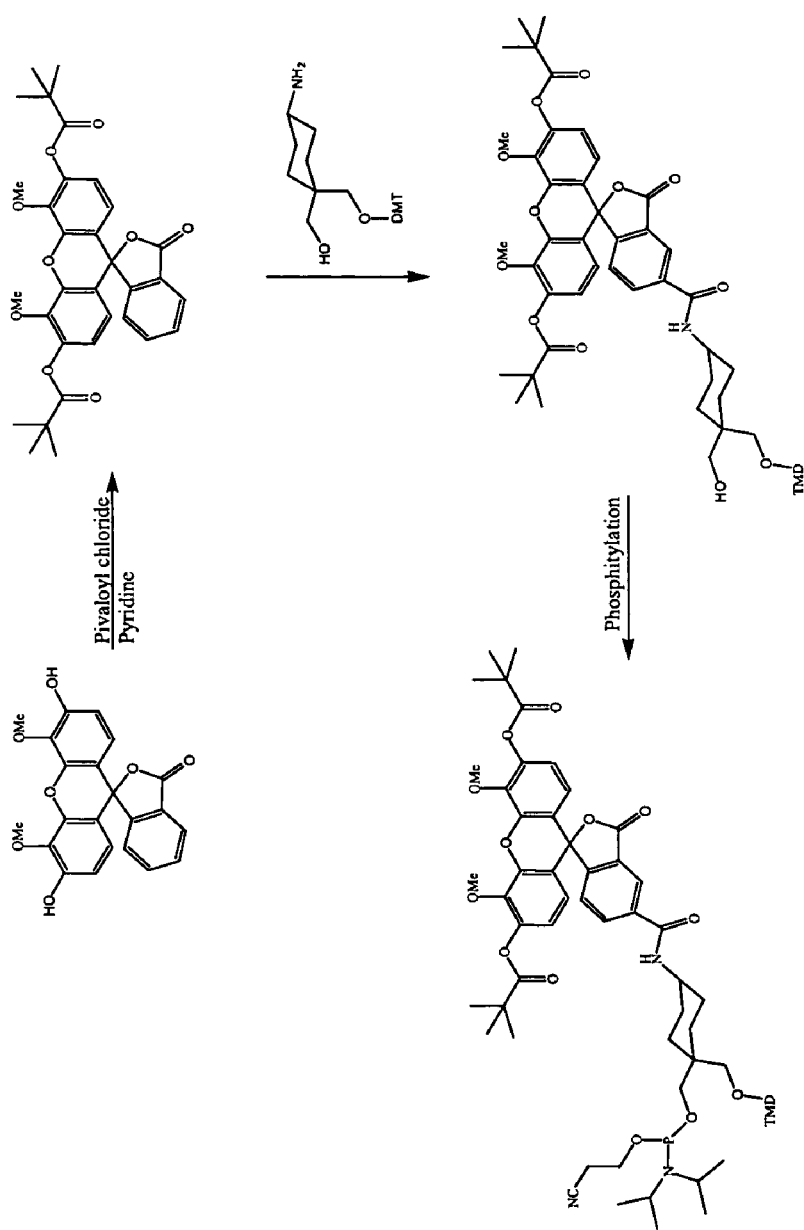
FIG. 27 schematically illustrates certain steps in a synthetic scheme of 5-DmF-DMT-CX-Linker-phosphoramidites according to one embodiment of the invention.
Figure 28:
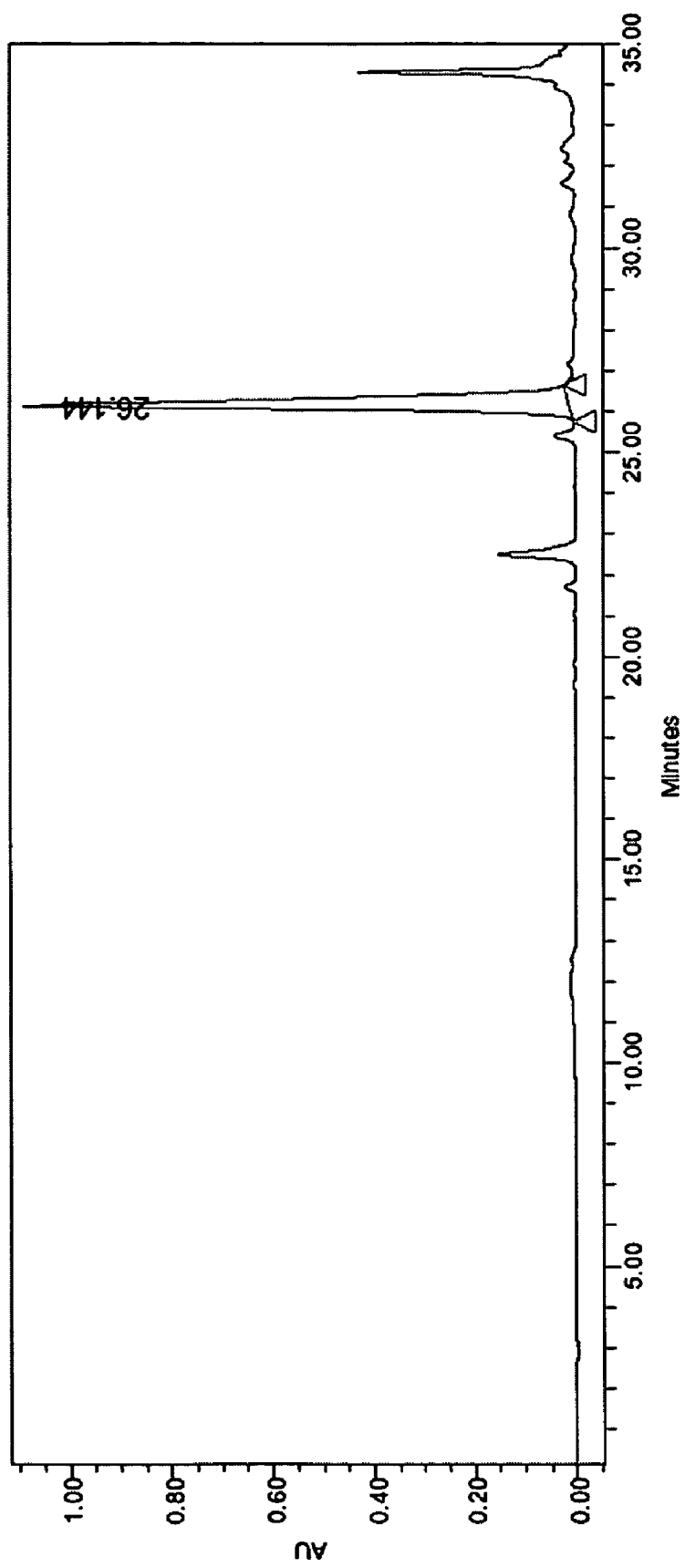
FIG. 28 is an HPLC trace that shows the detection of pivalated 5-DmF.
Figure 29:
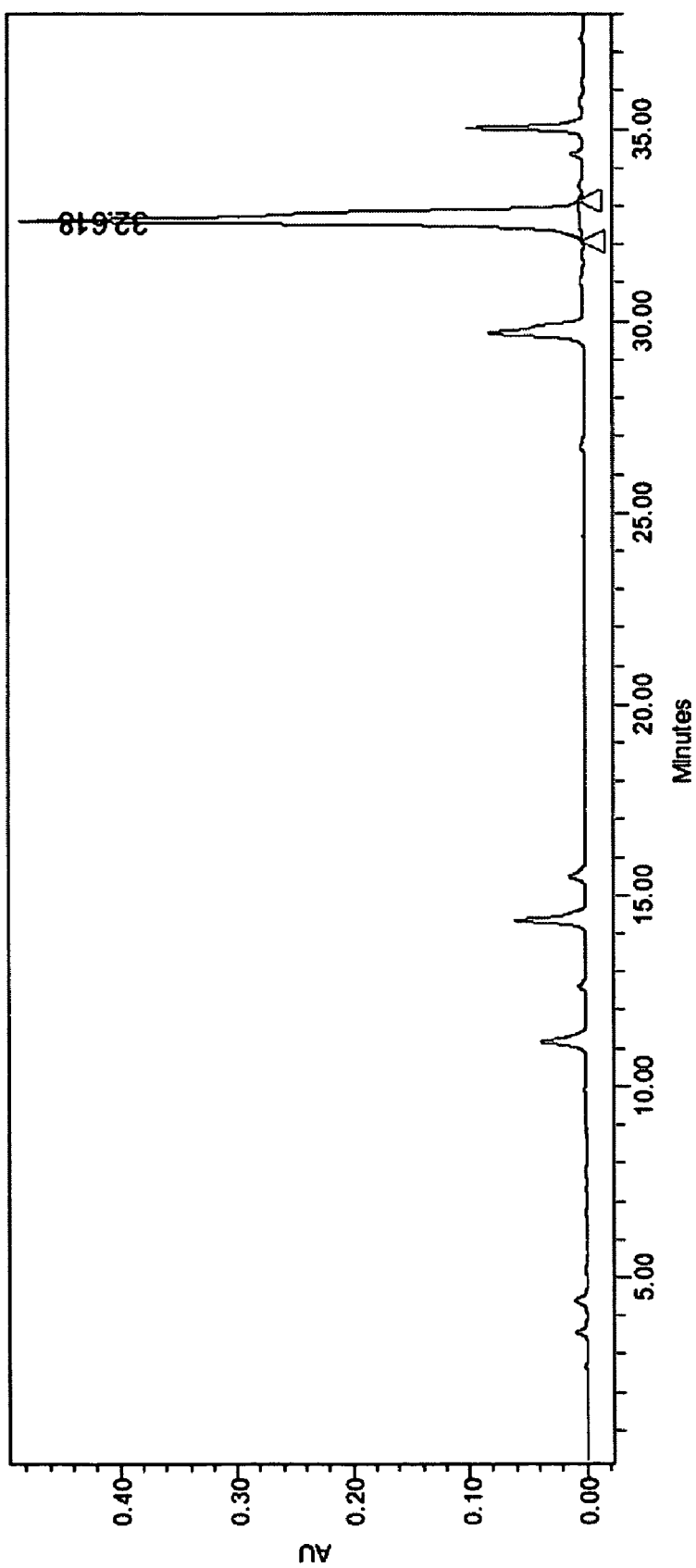
FIG. 29 is an HPLC trace that shows the detection of 5-DmF–CX-linker.

The methods for the synthesis of 5-DmF-DMT-CX-linker-phosphoramidite are identical to the methods, described above, for 5- and 6-DmF-DMT-CX-linker-phosphoramidites. In particular, FIG. 27 schematically illustrates certain steps in this synthetic scheme. In addition, FIGS. 28 and 29 are HPLC traces that show the detection of pivalated 5-DmF and 5-DmF–CX-linker, respectively (ordinates represent absorbance units, abscissas represent retention time (minutes)).

Example III

Hybridization Probe Assays

Figure 30:
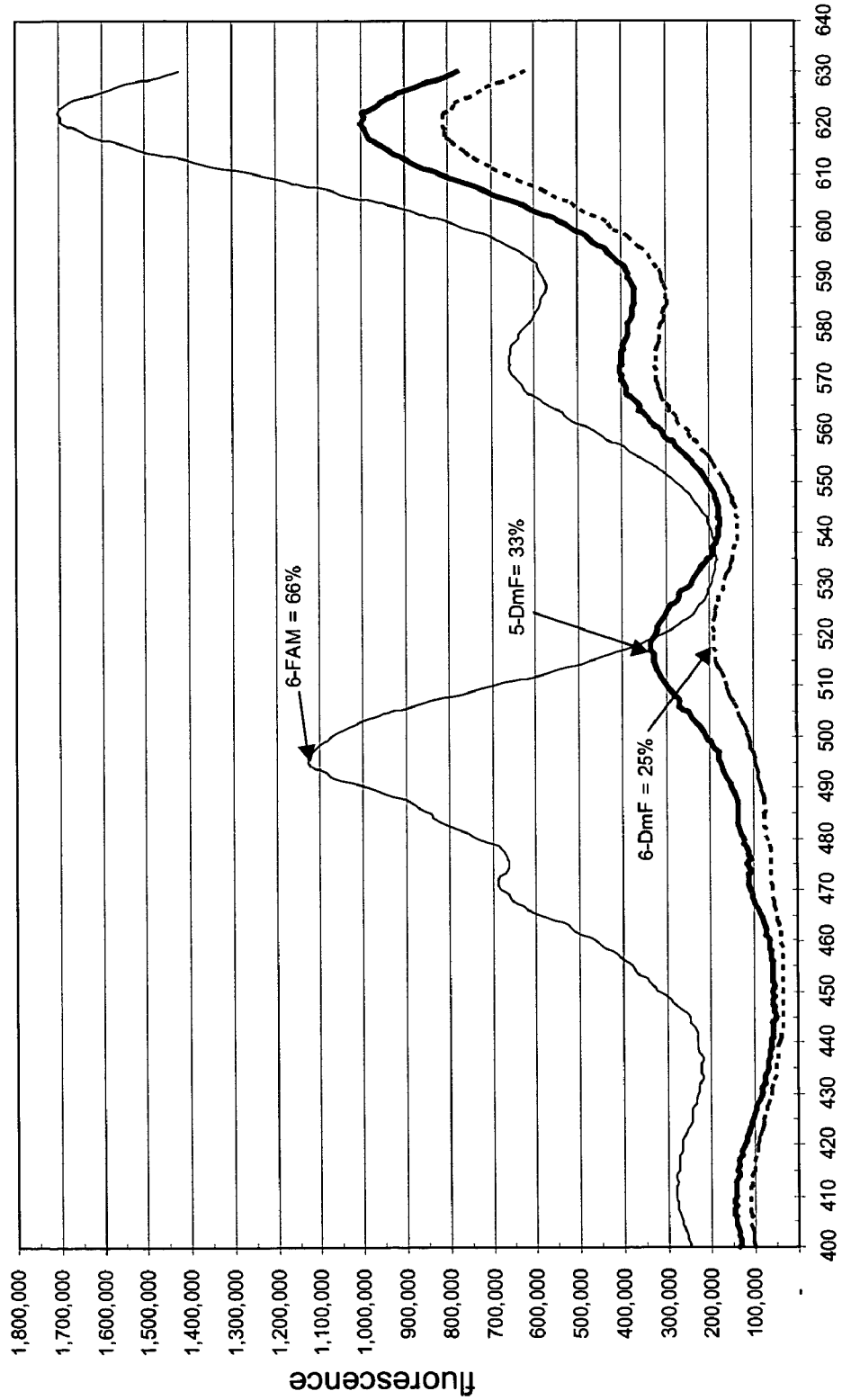
FIG. 30 is a plot of overlaid spectra obtained from excitation scans of various hybridization probe assays that included donor probes labeled with 6-FAM, 5-DmF, or 6-DmF.
Figure 31:
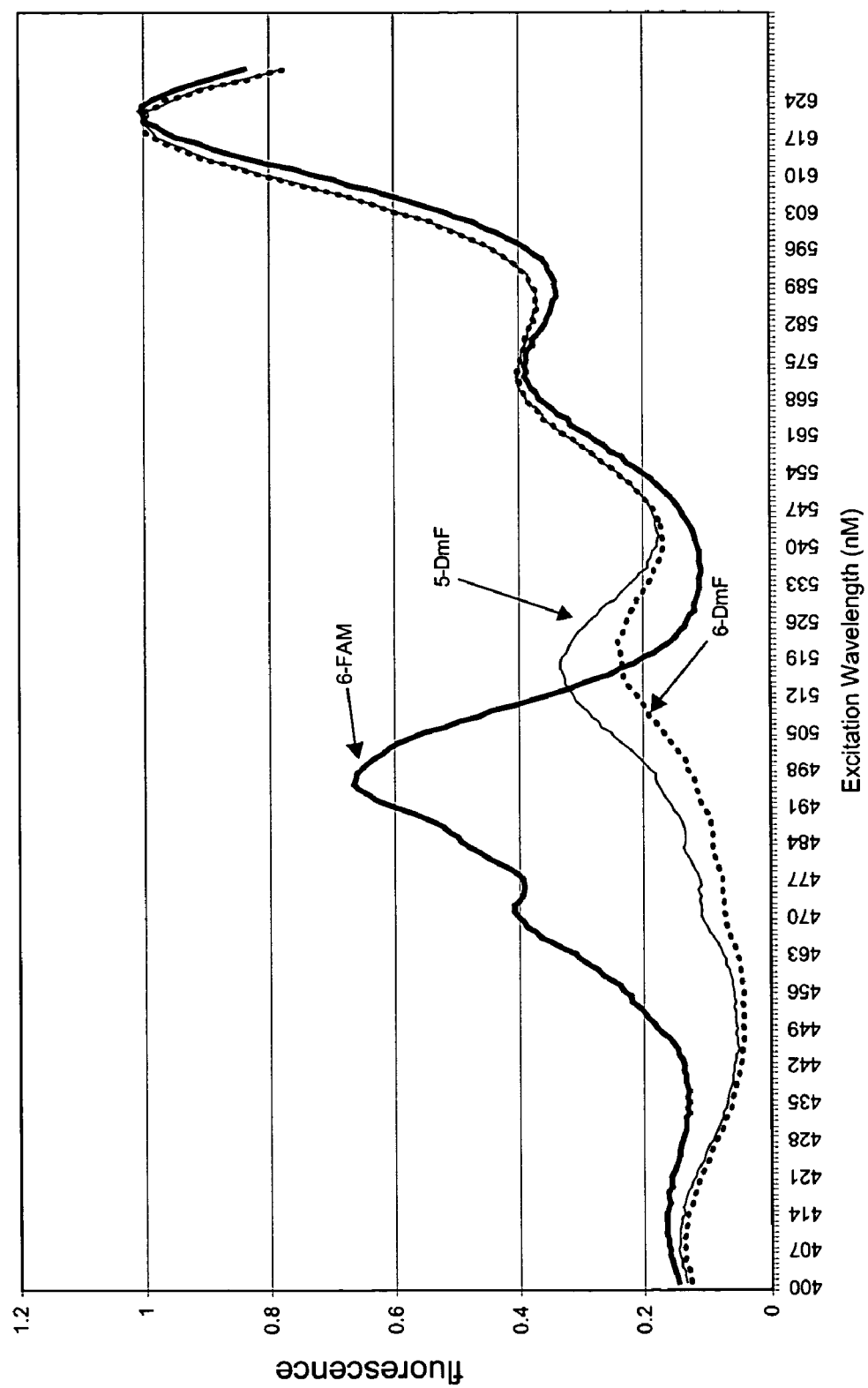
FIG. 31 is a plot of the overlaid spectra shown in FIG. 30 in which the detected fluorescence excitation scans have been normalized.

A phosphoramidite of the dye dimethoxyfluorescein (DmF) was synthesized as described in Example II and incorporated into an oligonucleotide at the 3'-end. This oligonucleotide or donor probe was hybridized to a target oligonucleotide along with an acceptor probe labeled with LightCycler® Red 640 (LC-Red 640). Fluorescence measurements were taken along with control experiments in which the analogous 6-carboxyfluorescein (6-FAM) donor probe was examined. The results show that the donor probe with DmF had no detectable fluorescence. In particular, when an excitation scan was performed, observing the fluorescence emission of the LC-Red 640 dye of the acceptor probe (at 640 nm) while scanning the excitation wavelength from 400-630 nm, an excitation peak was observed at approximately 520 nm, which coincides with the absorbance maximum of the DmF dye. This suggested that the substantially non-fluorescent DmF transferred absorbed light as non-fluorescent energy to LC-Red 640. The intensity of the new excitation peak was about half that of 6-FAM for one of the isomers of the DmF dye (i.e., 5-DmF). Plots of overlaid spectra obtained from these excitation scans are shown in FIG. 30 in which the ordinate of the graph represents absolute fluorescence, while the abscissa represents wavelength (nm). As shown, the trace for the scan that involved the 6-FAM donor probe is labeled "6-FAM", while the traces for the scans that involved the DmF donor probes are labeled "5-DmF" and "6-DmF". To further illustrate, FIG. 31 is a plot of the overlaid spectra shown in FIG. 30 in which the fluorescence excitation scans have been normalized (i.e., the ordinate of the graph represents normalized fluorescence, while the abscissa represents excitation wavelength (nm)).

Figure 32:
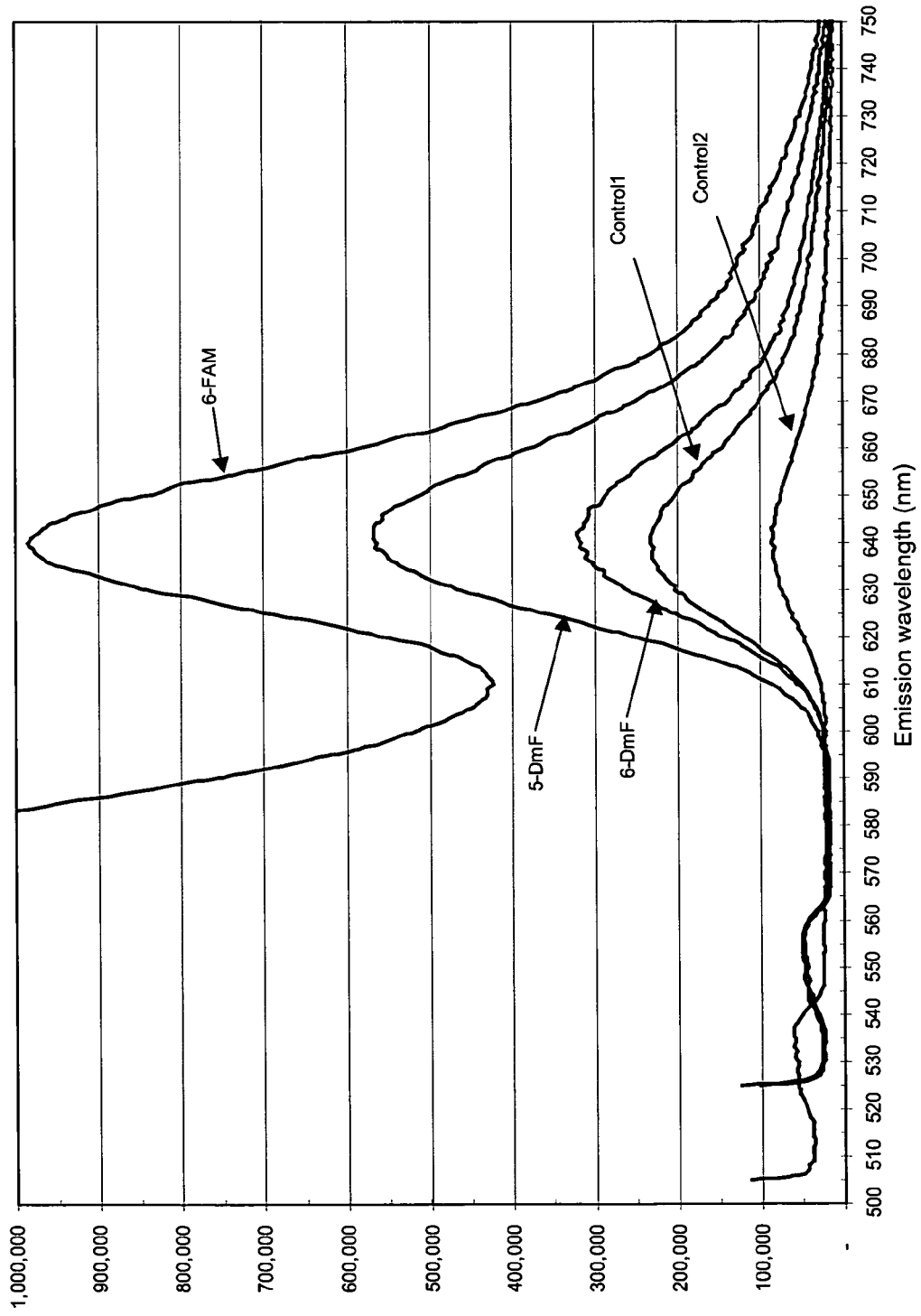
FIG. 32 is a plot of the overlaid spectra obtained from emission scans of various hybridization probe assays that included donor probes labeled with 6-FAM, 5-DmF, 6-DmF, or lacked donor probes.

When emission scans were performed, no signal was obtained from the DmF-labeled donor probes. In contrast, enormous emission was detected from the 6-FAM label in the control experiment. A plot of the overlaid spectra obtained from these scans is presented in FIG. 32 in which the ordinate of the graph represents absolute fluorescence, while the abscissa represents wavelength (nm). In particular, the trace for the emission scan obtained at an excitation wavelength of 493 nm from the hybridization probe assay that included 6-FAM-labeled donor probes is labeled "6-FAM". Traces for scans obtained at excitation wavelengths of 514 nm from the assays that included the DmF-labeled donor probes are labeled "5-DmF" and "6-DmF". As negative controls, assays were also performed in which donor probes were absent from the reaction mixtures. The trace for the emission scan obtained at an excitation wavelength of 514 nm from one of these control assays is labeled "Control 1", while the trace for the emission scan obtained at an excitation wavelength of 493 nm from another of these control assays is labeled "Control 2".

Example IV

Melting Curve Analyses

Figure 33:
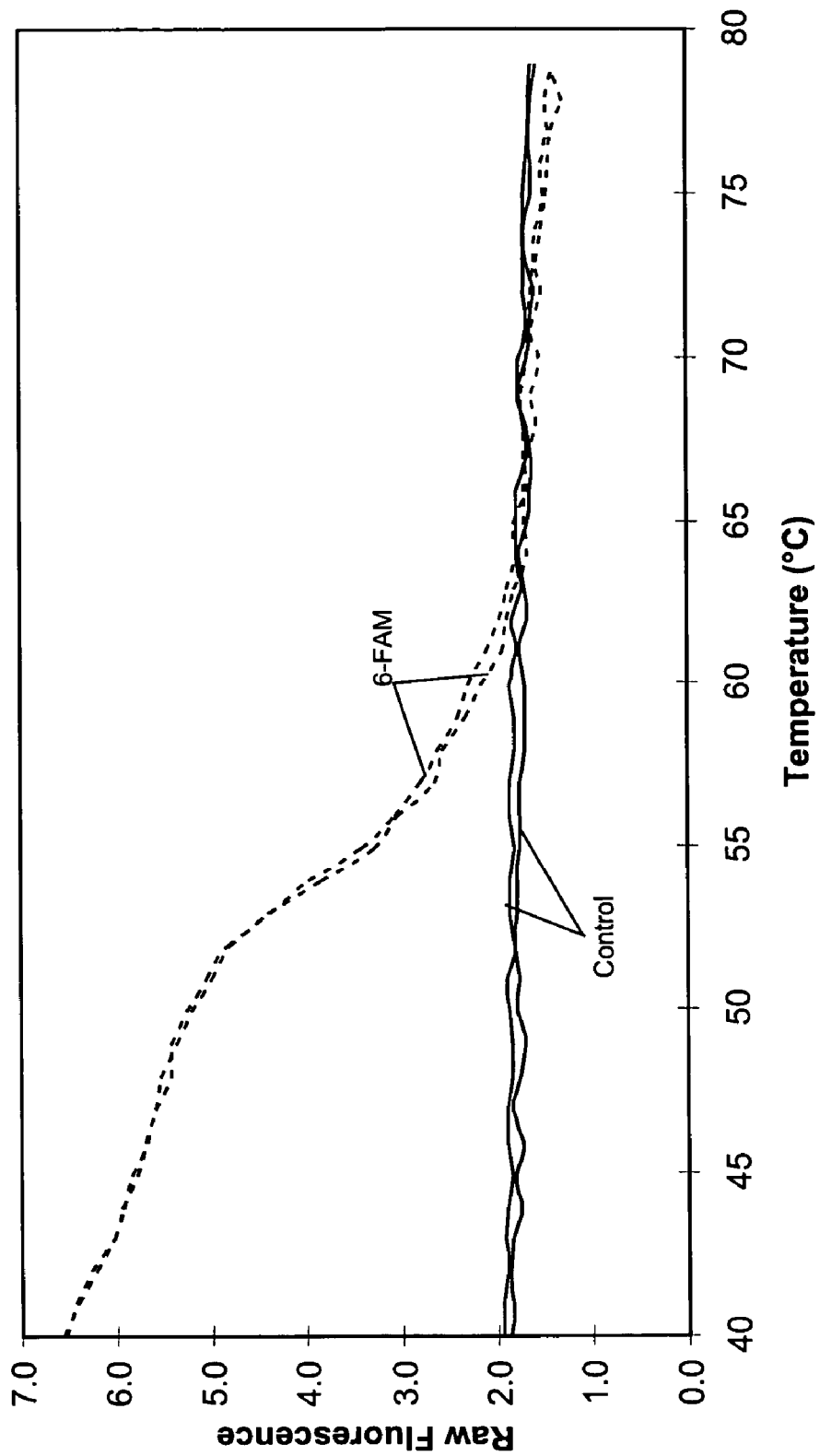
FIG. 33 is a plot of overlaid spectra obtained from a melting curve analysis that included donor probes labeled with 6-FAM.
Figure 34:
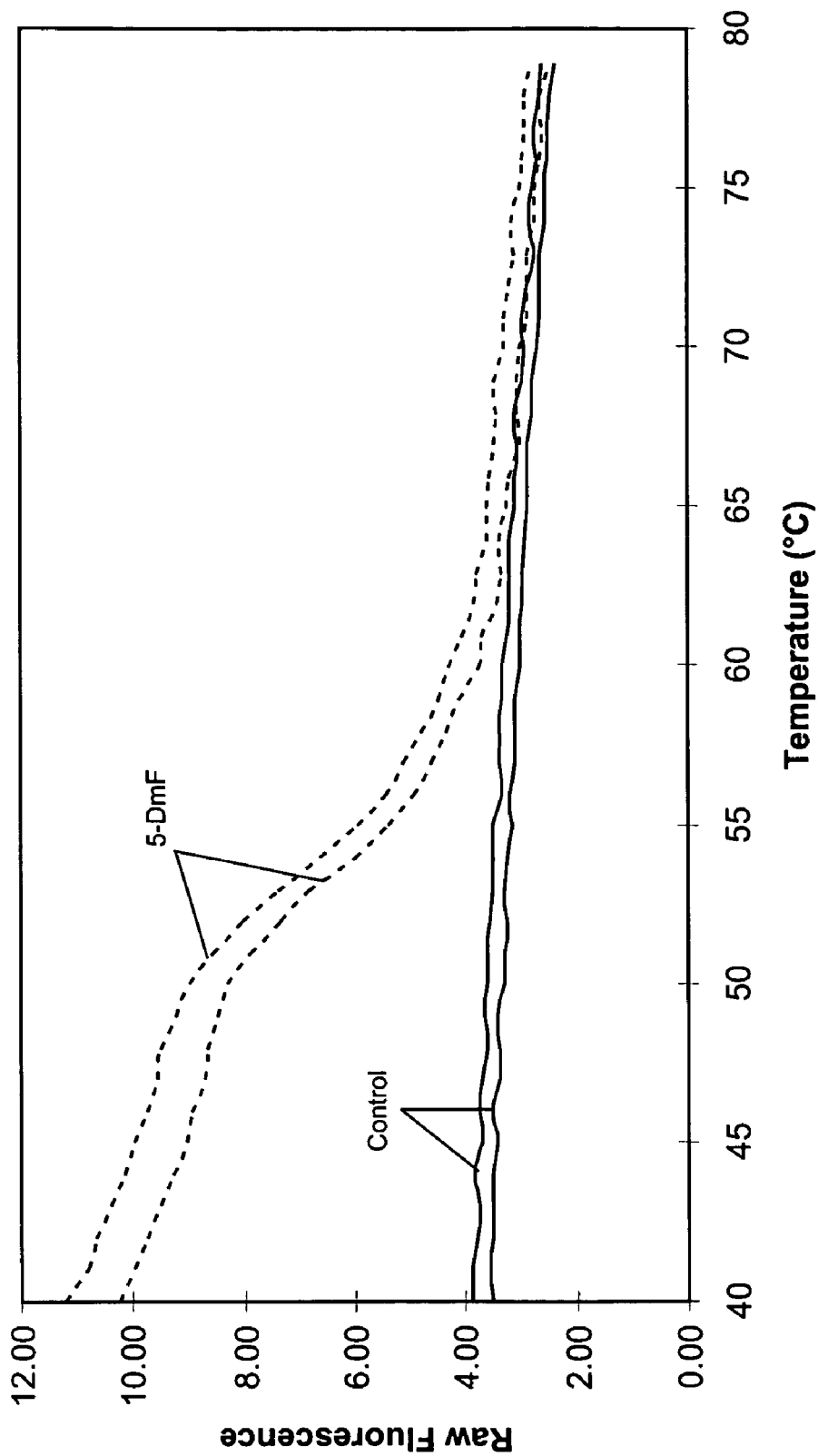
FIG. 34 is a plot of overlaid spectra obtained from a melting curve analysis that included donor probes labeled with 5-DmF.

Melting curve analyses were performed using hybridization probe pairs that included donor probes labeled either with a fluorescent moiety or a substantially non-fluorescent moiety. More specifically, one set of melting curve assays included a hybridization probe pair in which the donor probe was labeled at the 3'-end with 6-FAM and the acceptor probe was labeled at the 5'-end with CY5.5. Another set of assays included a hybridization probe pair in which the donor probe was labeled at the 3'-end with 5-DmF and the acceptor probe was labeled at the 5'-end with CY5.5. The same target nucleic acid was used in each assay at the same copy number, namely, 100,000 copies. The melting curves obtained for these analyses are shown in FIGS. 33 and 34 in which the ordinates of the graphs represent raw fluorescence, while the abscissas represent temperature (° C.). Traces obtained for assays that included 6-FAM donor probes are labeled "6-FAM", while traces obtained for assays that included 5-DmF donor probes are labeled "5-DmF". Negative controls were also performed in which donor probes were absent from the reaction mixtures. As shown in FIGS. 33 and 34, each melting curve assay was performed in duplicate.

Example V

Hybridization Probe Based Real-Time PCR Monitoring

Figure 35:
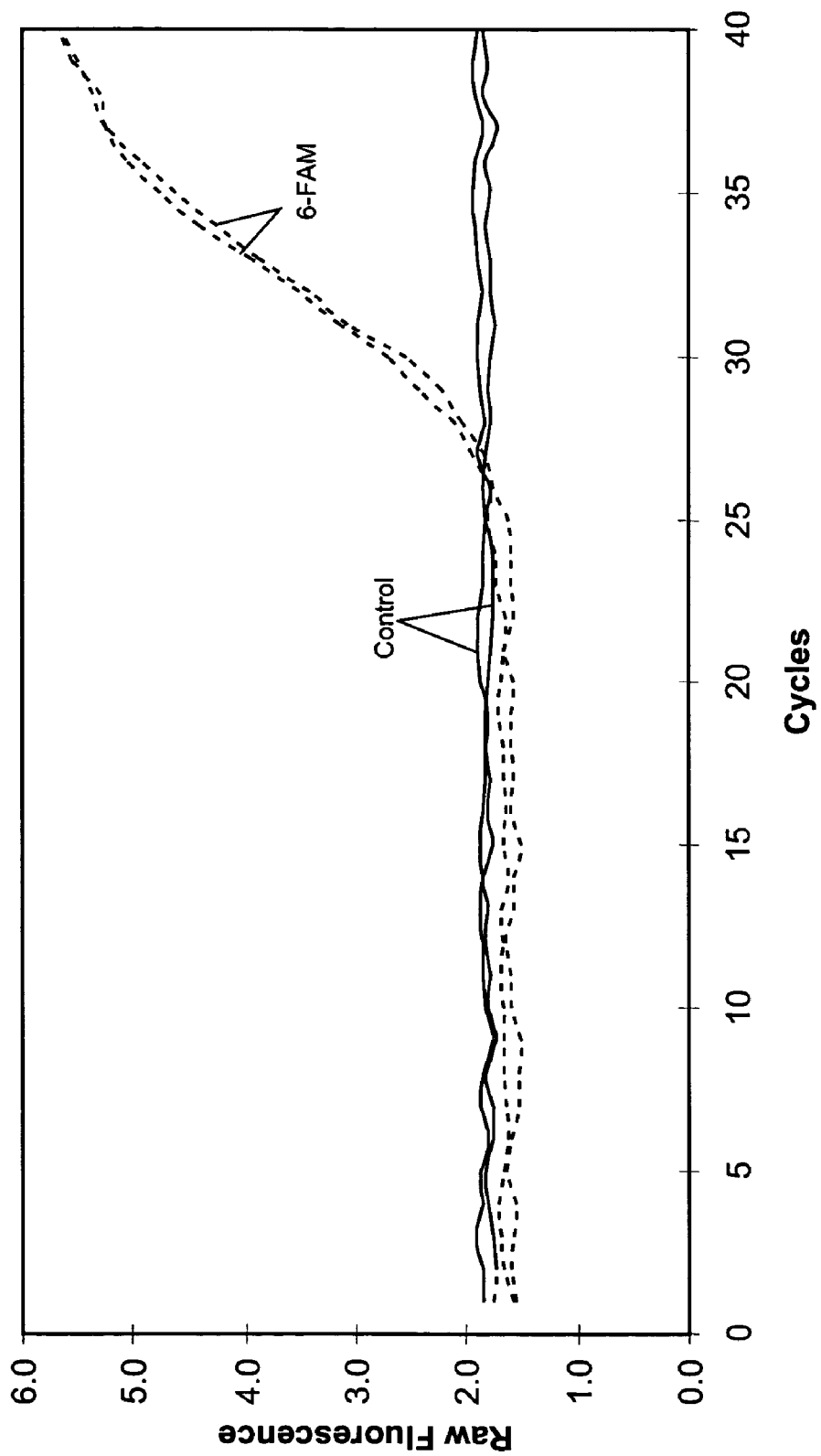
FIG. 35 is a plot of overlaid spectra obtained from a kinetic PCR analysis that included donor probes labeled with 6-FAM.
Figure 36:
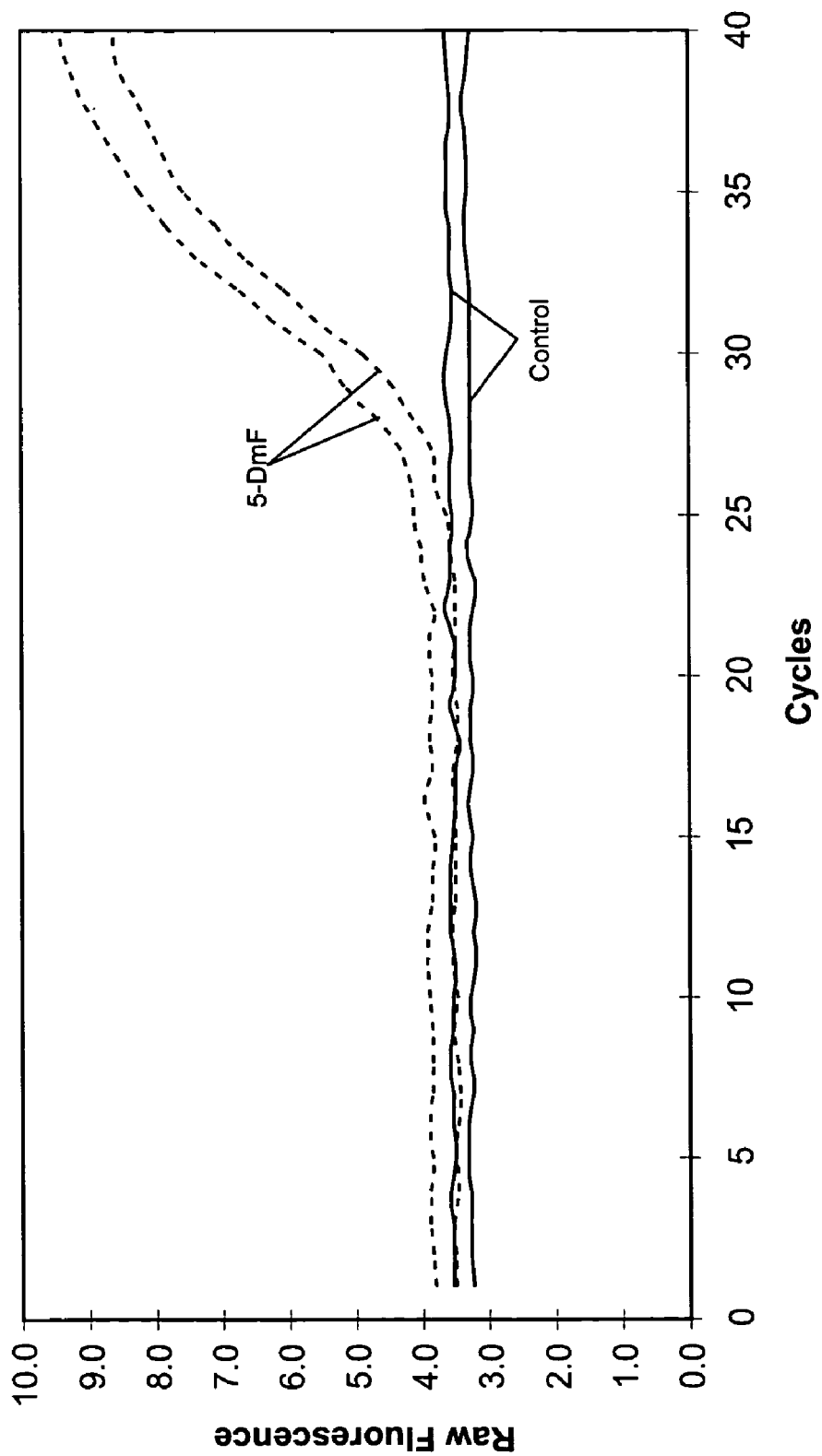
FIG. 36 is a plot of overlaid spectra obtained from a kinetic PCR analysis that included donor probes labeled with 5-DmF.

The hybridization probe pairs described in Example IV were also used to monitor polymerase chain reactions. In particular, the growth curves obtained for these analyses are shown in FIGS. 35 and 36 in which the ordinates of the graphs represent raw fluorescence, while the abscissas represent cycle number. Traces obtained for assays that included 6-FAM donor probes are labeled "6-FAM", while traces obtained for assays that included 5-DmF donor probes are labeled "5-DmF". Negative controls were also performed in which donor probes were absent from the reaction mixtures. The same target nucleic acid was used in each assay at the same copy number, namely, 100,000 copies. As shown in FIGS. 35 and 36, each PCR was performed in duplicate.

Example VI

5'-Nuclease Probe Based Real-Time PCR Monitoring

PCR assays were also monitored using 5'-nuclease probes that included substantially non-fluorescent moieties or that lacked such moieties in energy transfer pairs. The 5'-nuclease probes used in these assays are schematically depicted in FIGS. 37A and 37B. As shown in FIG. 37A, probe 600 (DmF Probe) included a quencher moiety (Q), namely, a Black Hole Quencher™ or BHQ™ (Biosearch Technologies, Inc., Novato, Calif., USA) at a 5'-end of the nucleic acid. In addition, probe 600 also included an energy transfer pair (ET Pair) that included DmF (donor moiety) and CY5.5 (acceptor moiety). Probe 602 (non-DmF Probe), shown in FIG. 37B, was the same as probe 600 except that fluorescein (FL) was substituted for DmF in the ET Pair as the donor moiety.

Figure 38:
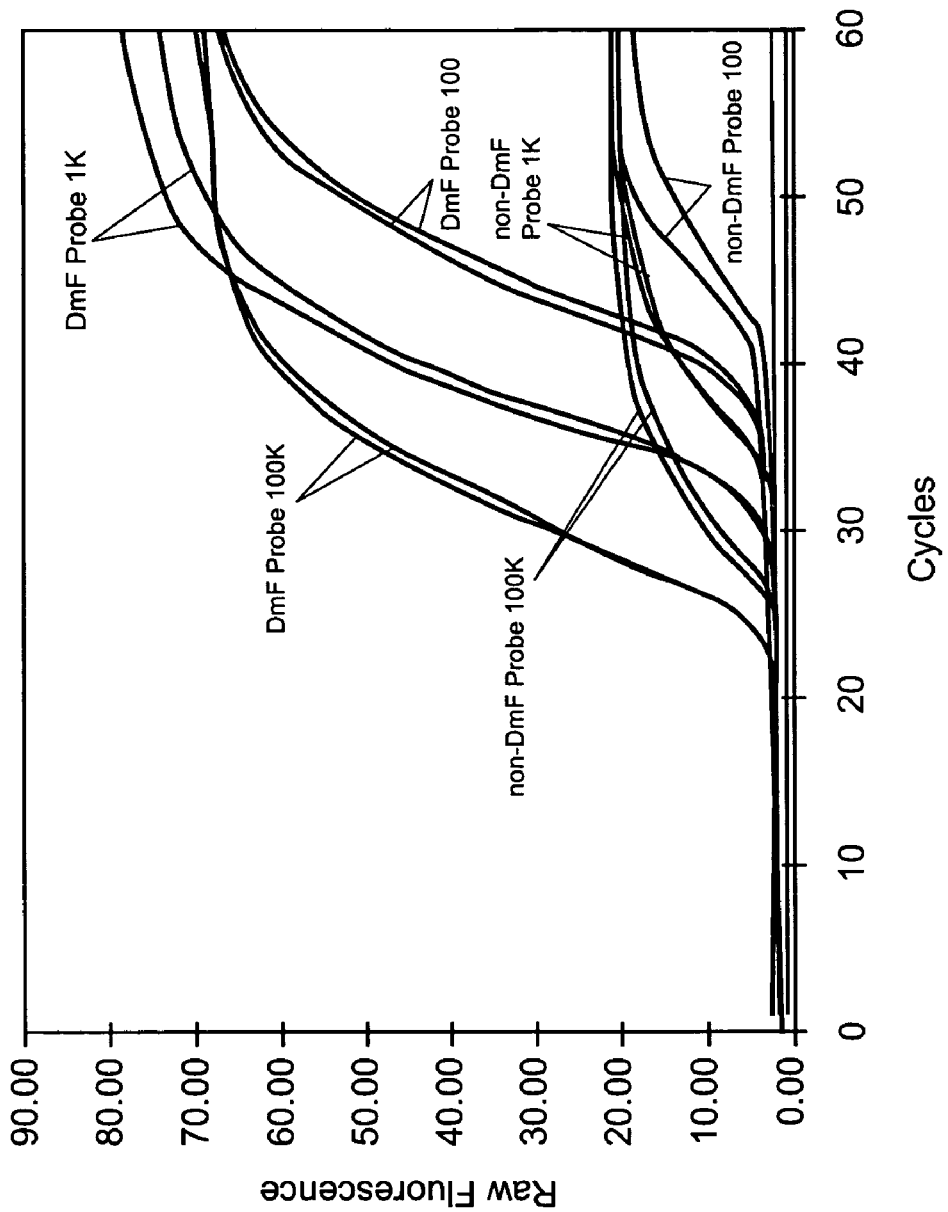
FIG. 38 is a plot of overlaid spectra obtained from PCR analyses in which 5'-nuclease probes were used to monitor the reactions.
Figure 39:
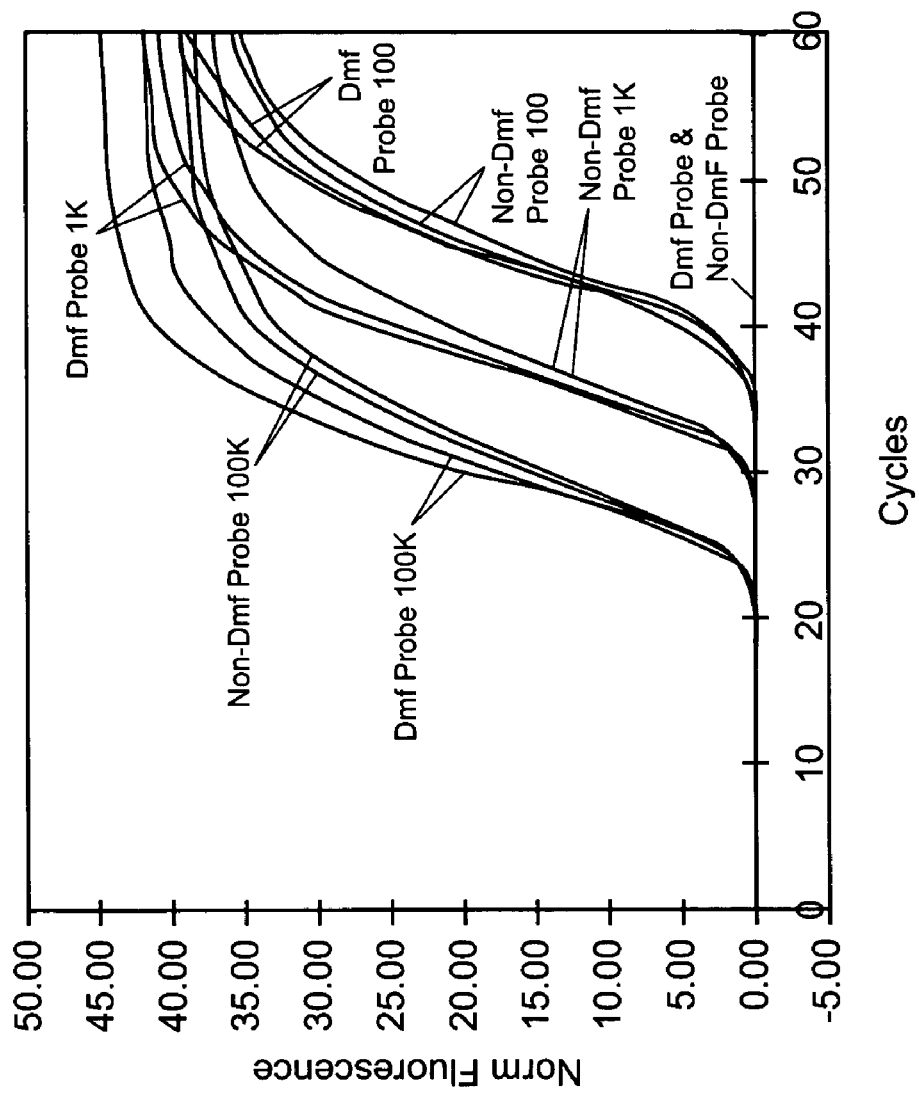
FIG. 39 is a plot of the overlaid spectra shown in FIG. 38 in which the detected fluorescence has been normalized.

Growth curves for various PCR assays that included the use of the 5'-nuclease probes, which are schematically depicted in FIGS. 37A and 37B, are provided in FIG. 38. The ordinate of the graph shown in FIG. 38 represents raw fluorescence, while the abscissa represents the cycle number. FIG. 39 is a plot of the growth curves shown in FIG. 38 in which the detected fluorescence has been normalized. As shown, traces corresponding to reactions that included DmF Probes and 100,000 initial copies of the template nucleic acid are labeled "DmF Probe 100K", traces corresponding to reactions that included DmF Probes and 1,000 initial copies of the template nucleic acid are labeled "DmF Probe 1K", and traces corresponding to reactions that included DmF Probes and 100 initial copies of the template nucleic acid are labeled "DmF Probe 100". Traces corresponding to reactions that included non-DmF Probes and 100,000 initial copies of the template nucleic acid are labeled "non-DmF Probe 100K", traces corresponding to reactions that included non-DmF Probes and 1,000 initial copies of the template nucleic acid are labeled "non-DmF Probe 1K", and traces corresponding to reactions that included non-DmF Probes and 100 initial copies of the template nucleic acid are labeled "non-DmF Probe 100". Negative controls in which reaction mixtures lacked template nucleic acids were also performed for both 5'-nuclease probes. Traces corresponding to these control reactions are labeled "DmF Probe & non-DmF Probe Controls". As shown in FIGS. 38 and 39, each PCR was performed in duplicate.

Example VII

Additional Hybridization Probe Assays

Figure 40:
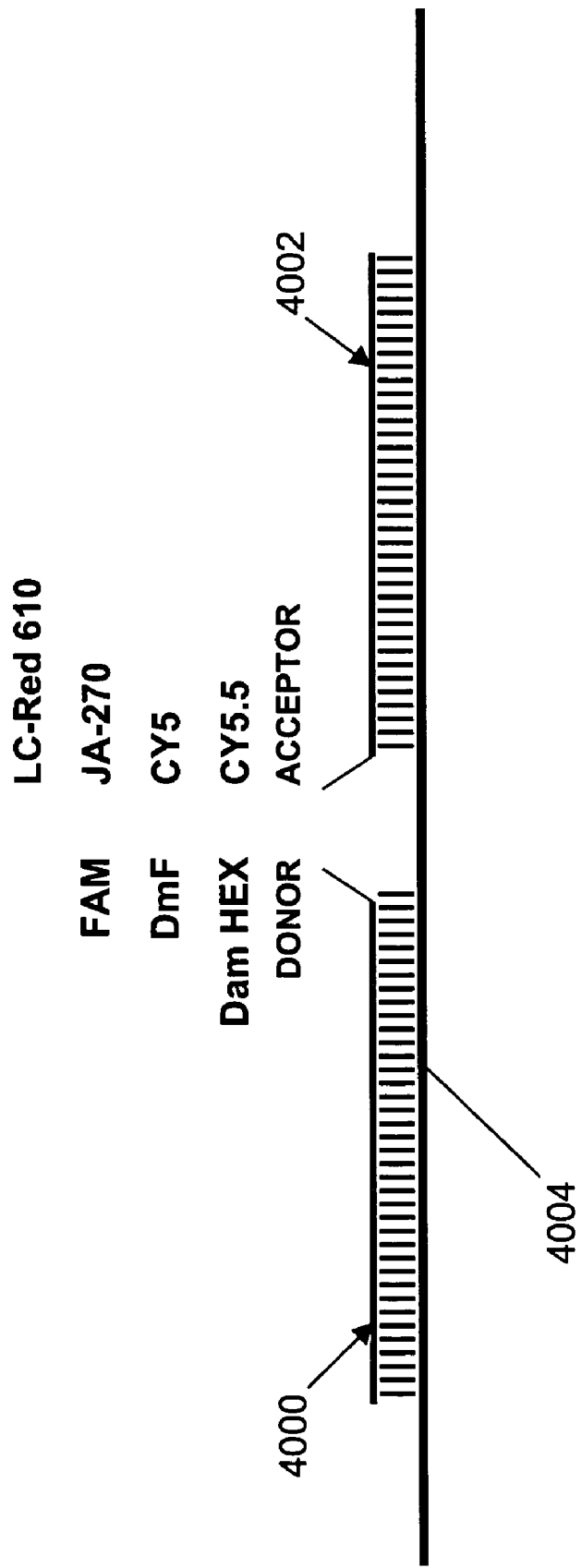
FIG. 40 schematically shows various donor and acceptor moieties in representative hybridization probe pairs.

This example shows certain performance characteristics of various combinations of donor and acceptor moieties in representative hybridization probe pairs. To illustrate, FIG. 40 schematically illustrates the donor and acceptor moieties of these hybridization probe pairs. As shown, donor probe 4000 and acceptor probe 4002 are hybridized to single-stranded complement 4004. The donor probes used in this example included FAM, DmF, or Dam HEX as donor moieties, while the acceptor probes used in this example included LC-Red 610, JA-270, CY3.5, CY5, or CY5.5 as acceptor moieties.

Figure 41A:
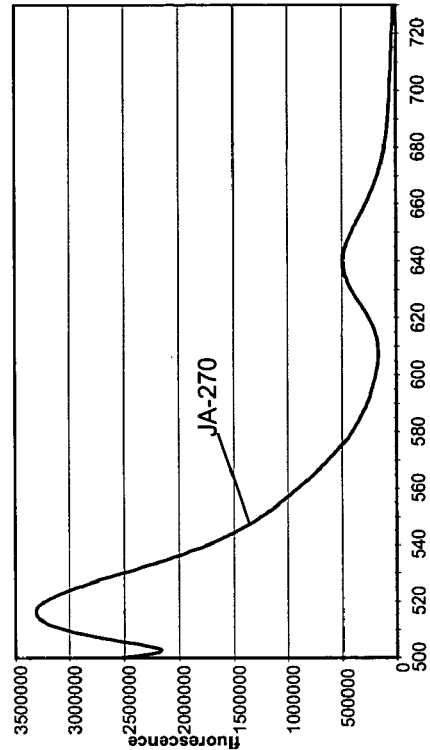
FIG. 41A is a plot of a spectrum obtained from an emission scan of a hybridization probe labeled with LC-Red 610.
Figure 41B:
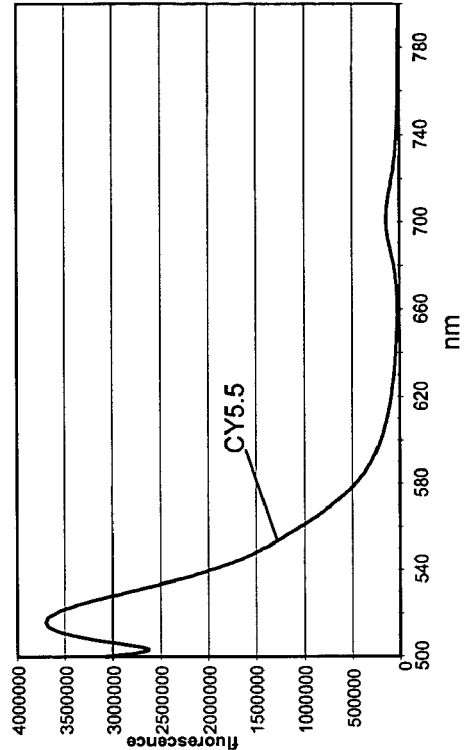
FIG. 41B is a plot of a spectrum obtained from an emission scan of a hybridization probe labeled with JA-270.
Figure 41C:
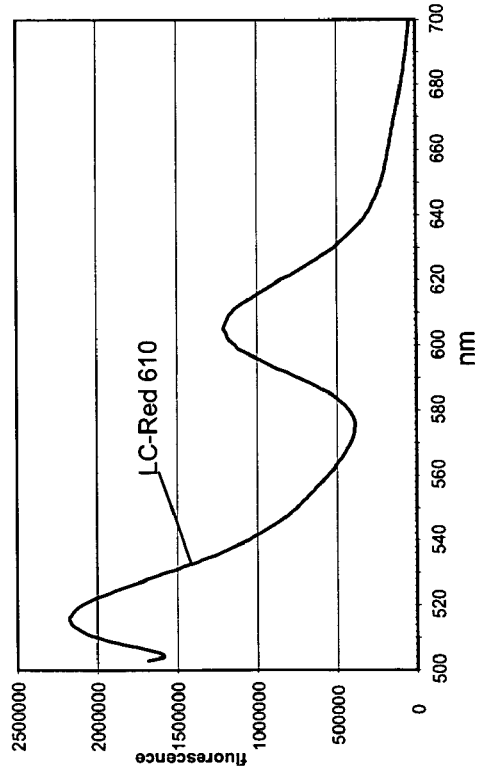
FIG. 41C is a plot of a spectrum obtained from an emission scan of a hybridization probe labeled with CY5.
Figure 41D:
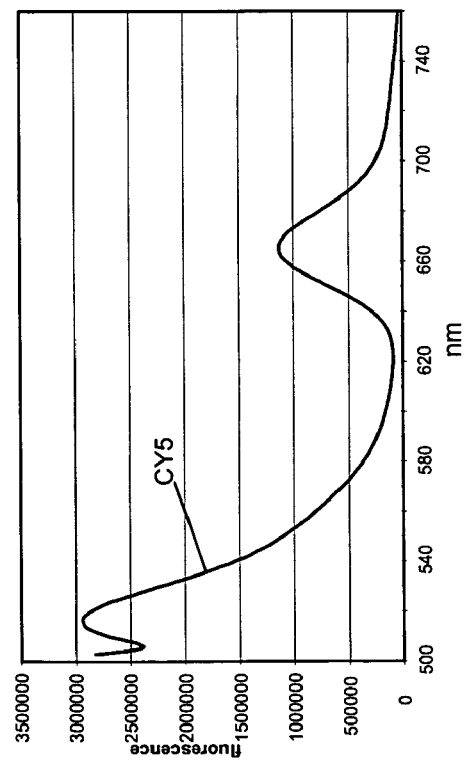
FIG. 41D is a plot of a spectrum obtained from an emission scan of a hybridization probe labeled with CY5.5.

FIGS. 41A-D are plots of emission scans (ordinates of the graphs represent absolute fluorescence, while the abscissas represent wavelength (nm)) obtained using the acceptor probes described above. In particular, FIG. 41A is a plot of an emission scan obtained from a hybridization probe labeled with LC-Red 610 and FIG. 41B is a plot of an emission scan obtained from a hybridization probe labeled with JA-270. Further, FIG. 41C is a plot of an emission scan obtained from a hybridization probe labeled with CY5, while FIG. 41D is a plot of an emission scan obtained from a hybridization probe labeled with CY5.5.

Figure 42A:
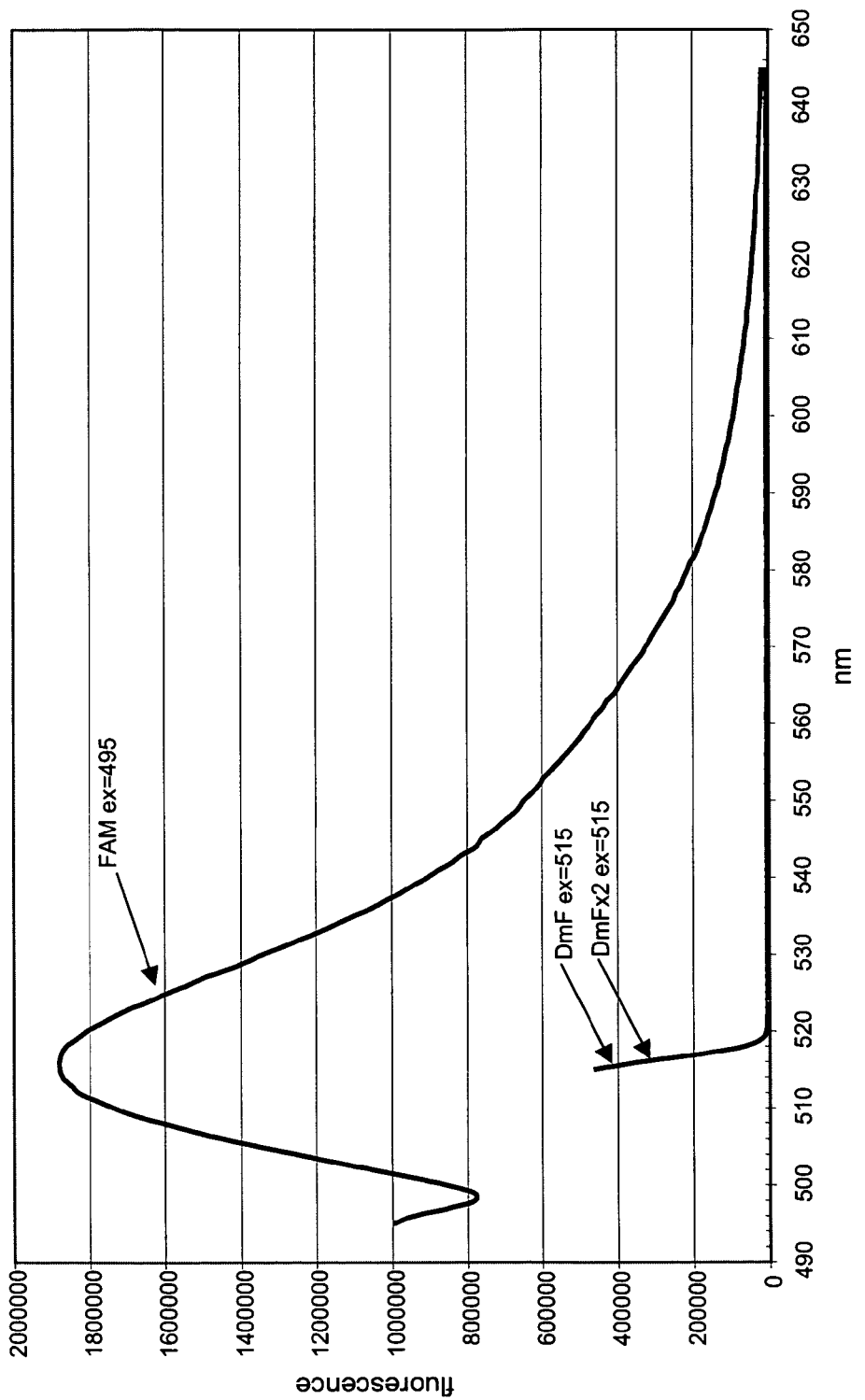
FIG. 42A is a plot of overlaid spectra obtained from emission scans (absolute fluorescence) of hybridization probes labeled with FAM or DmF.
Figure 42B:
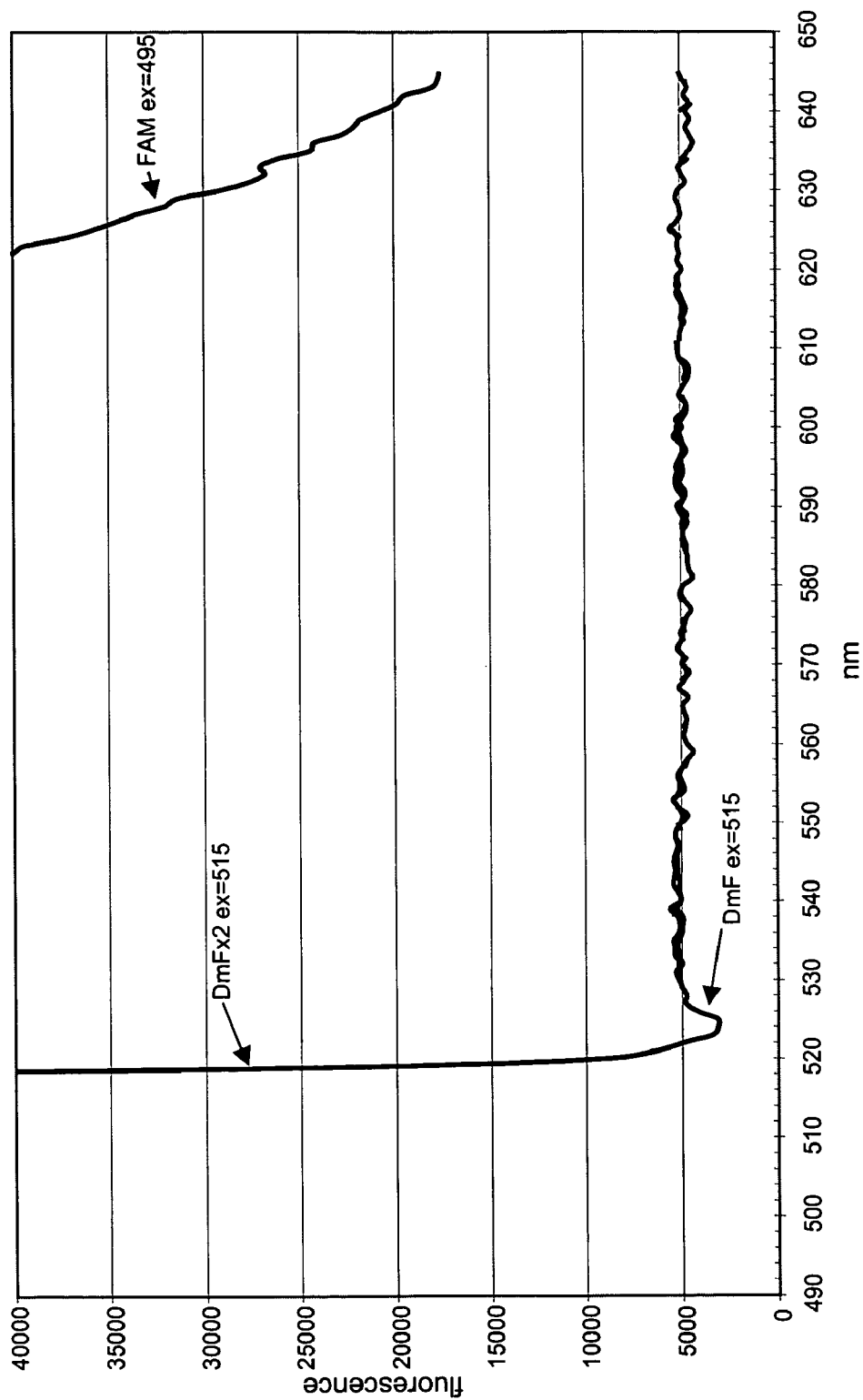
FIG. 42B is a plot of certain overlaid spectra obtained from the emission scans plotted in FIG. 42A in which the fluorescent emissions have been scaled.

FIG. 42A is an overlaid plot of emission scans (the ordinate represents absolute fluorescence, while the abscissa represents wavelength (nm)) obtained from hybridization probes labeled with FAM, one DmF molecule (6-carboxy isomer) (DmF), or two DmF molecules (6-carboxy isomer) (DmFx2). The excitation wavelength (nm) for each trace is indicated (ex). FIG. 42B is an overlaid plot of certain emission scans plotted in FIG. 42A in which the relative fluorescent emissions are provided.

Figure 43A:
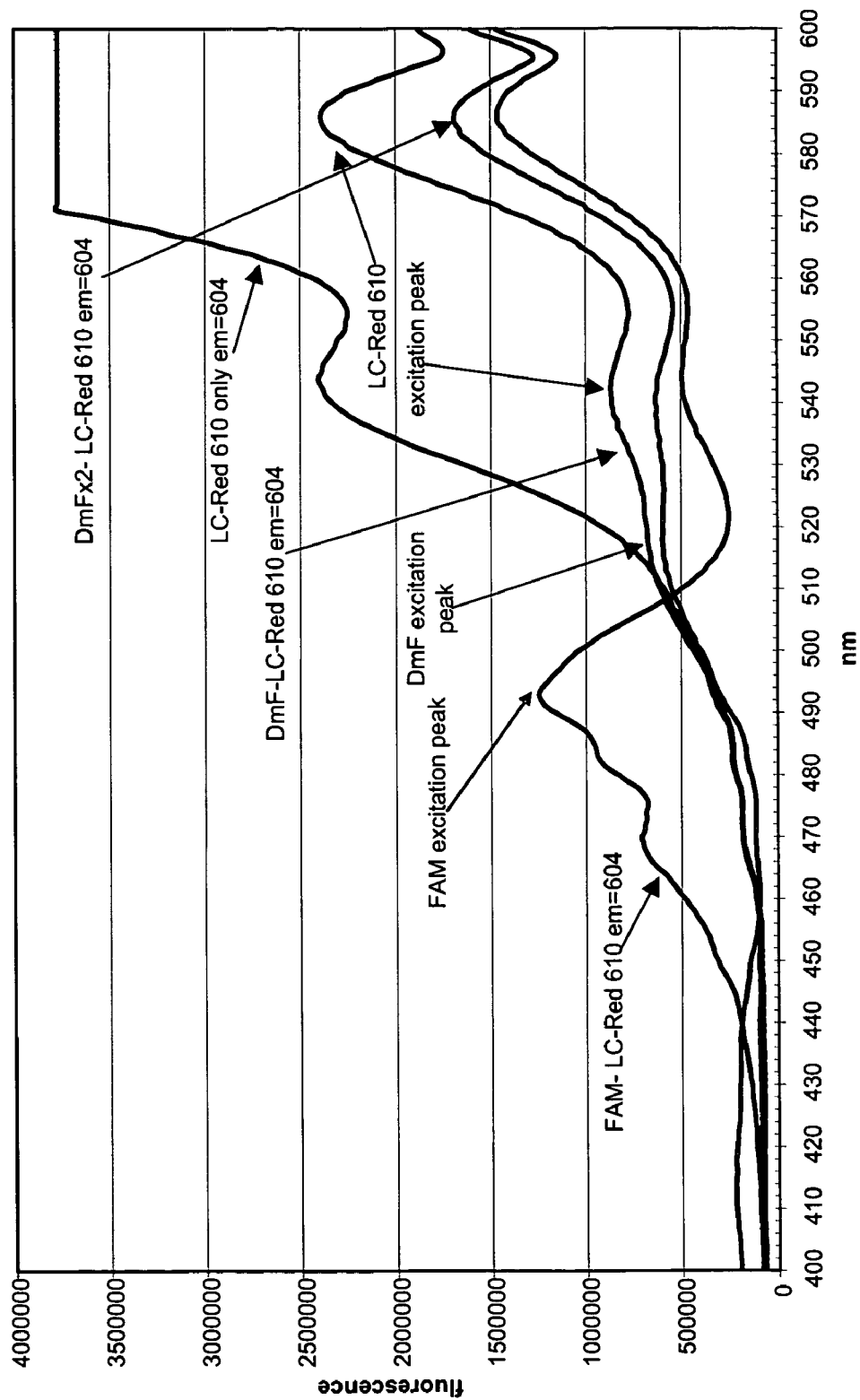
FIG. 43A is a plot of overlaid spectra obtained from excitation scans of hybridization probe assays that involved acceptor probes labeled with LC-Red 610 and donor probes labeled with FAM or DmF.
Figure 43B:
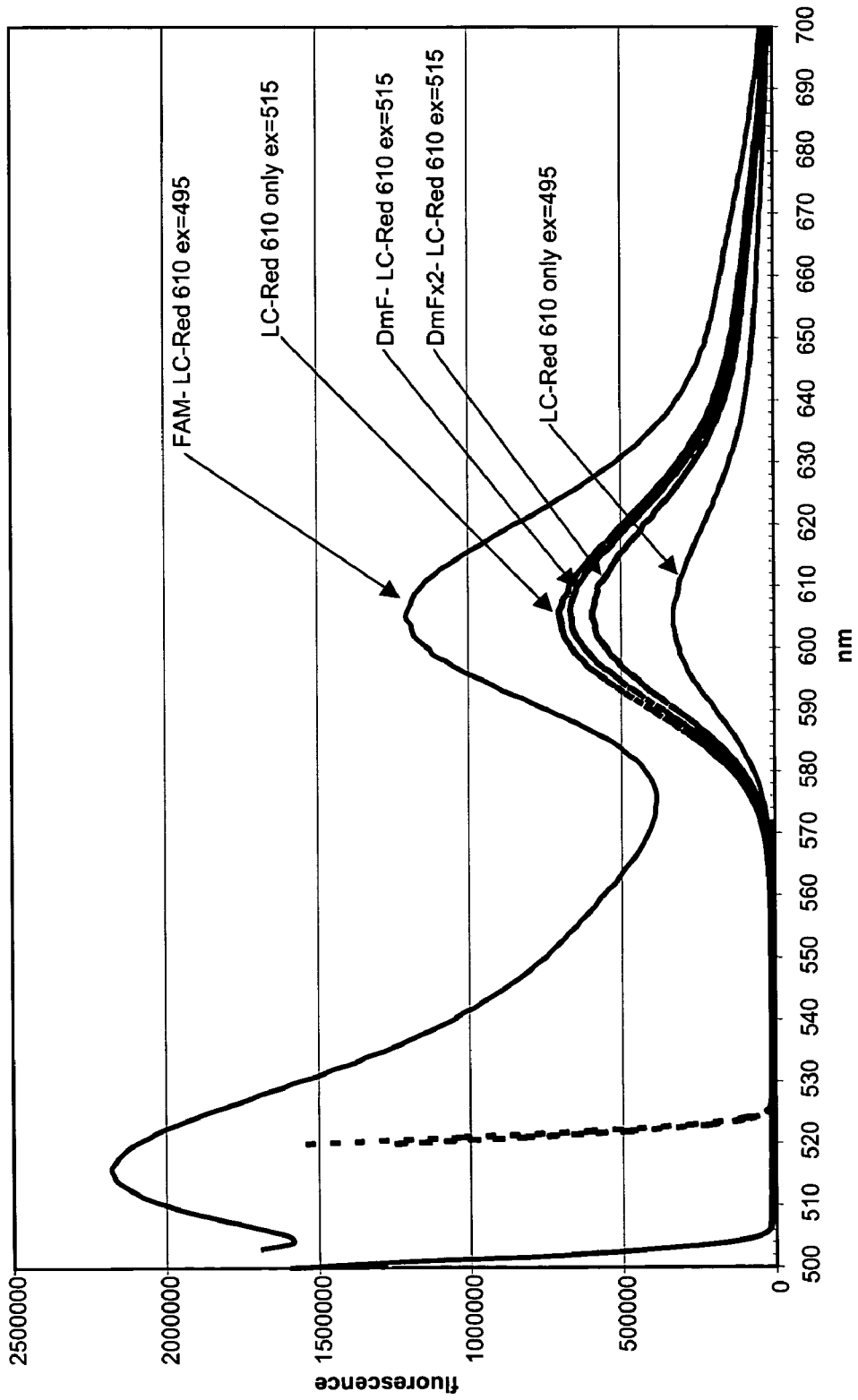
FIG. 43B is a plot of overlaid spectra obtained from emission scans (absolute fluorescence) of hybridization probe assays that involved acceptor probes labeled with LC-Red 610 and donor probes labeled with FAM or DmF.
Figure 43C:
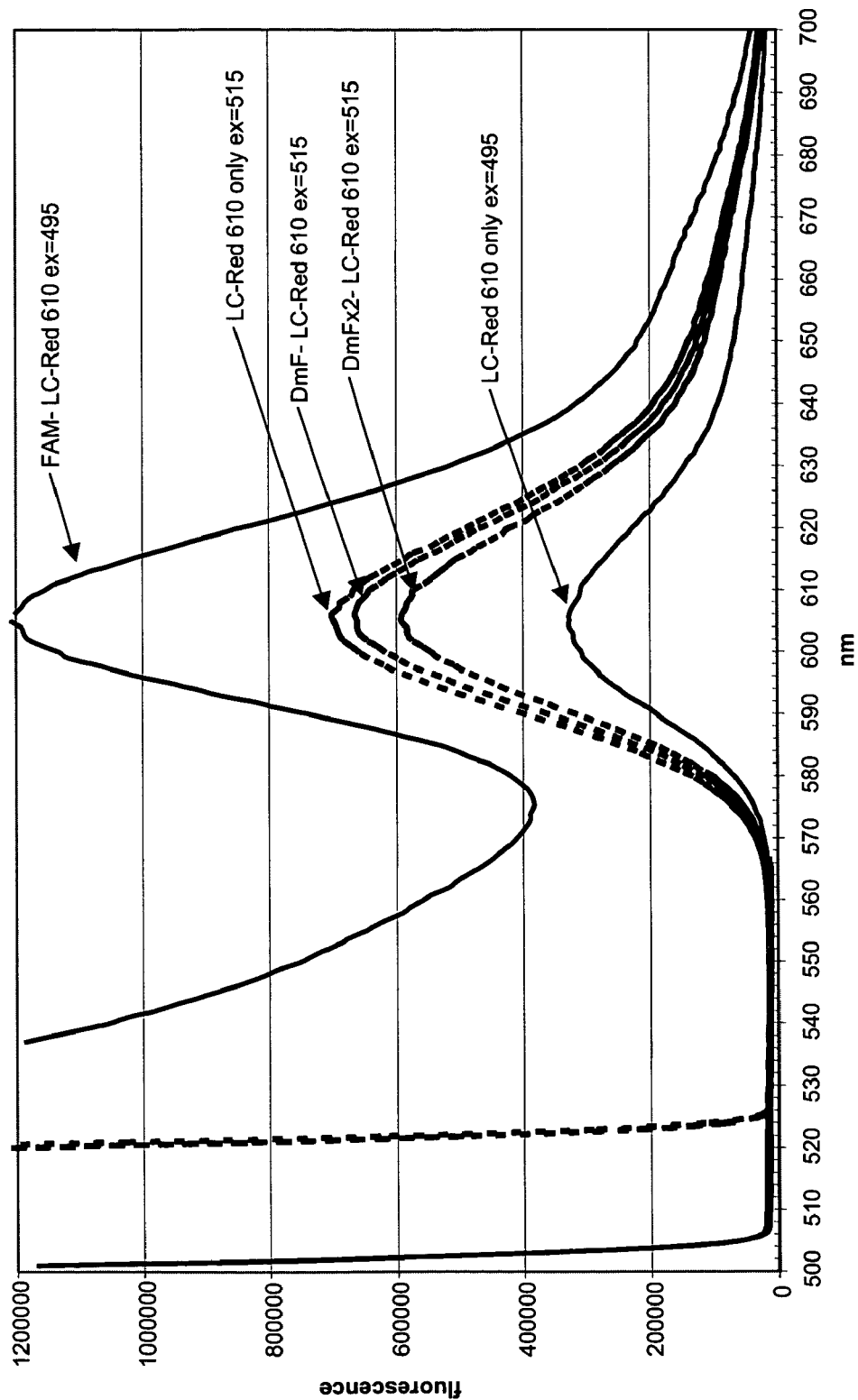
FIG. 43C is a plot of overlaid spectra obtained from the emission scans plotted in FIG. 43B in which the fluorescent emissions have been scaled.

FIG. 43A is an overlaid plot of excitation scans (the ordinate represents absolute fluorescence, while the abscissa represents wavelength (nm)) of hybridization probe assays that involved acceptor probes labeled with LC610 (emission maximum=604 nm) and donor probes labeled with FAM, DmF, or DmFx2. The excitation peaks of FAM, DmF, and LC-Red 610 are also shown. The emission wavelength (nm) for each trace is indicated (em). As also shown, a scan for a negative control that included only the acceptor probe (LC-Red 610 only em=604) in the reaction mixture was also obtained. FIG. 43B is an overlaid plot of emission scans (the ordinate represents absolute fluorescence, while the abscissa represents wavelength (nm)) of these hybridization probe assays that involved acceptor probes labeled with LC-Red 610 and donor probes labeled with FAM, DmF, or DmFx2. The excitation wavelength (nm) corresponding to each trace is indicated (ex). As also shown, scans for negative controls that included only the acceptor probe in the reaction mixture were also obtained at an excitation wavelength of 495 nm (LC-Red 610 only ex=495) and at an excitation wavelength of 515 nm (LC-Red 610 only ex=515). FIG. 43C is an overlaid plot of the emission scans plotted in FIG. 43B in which the relative fluorescent emissions are provided.

Figure 44A:
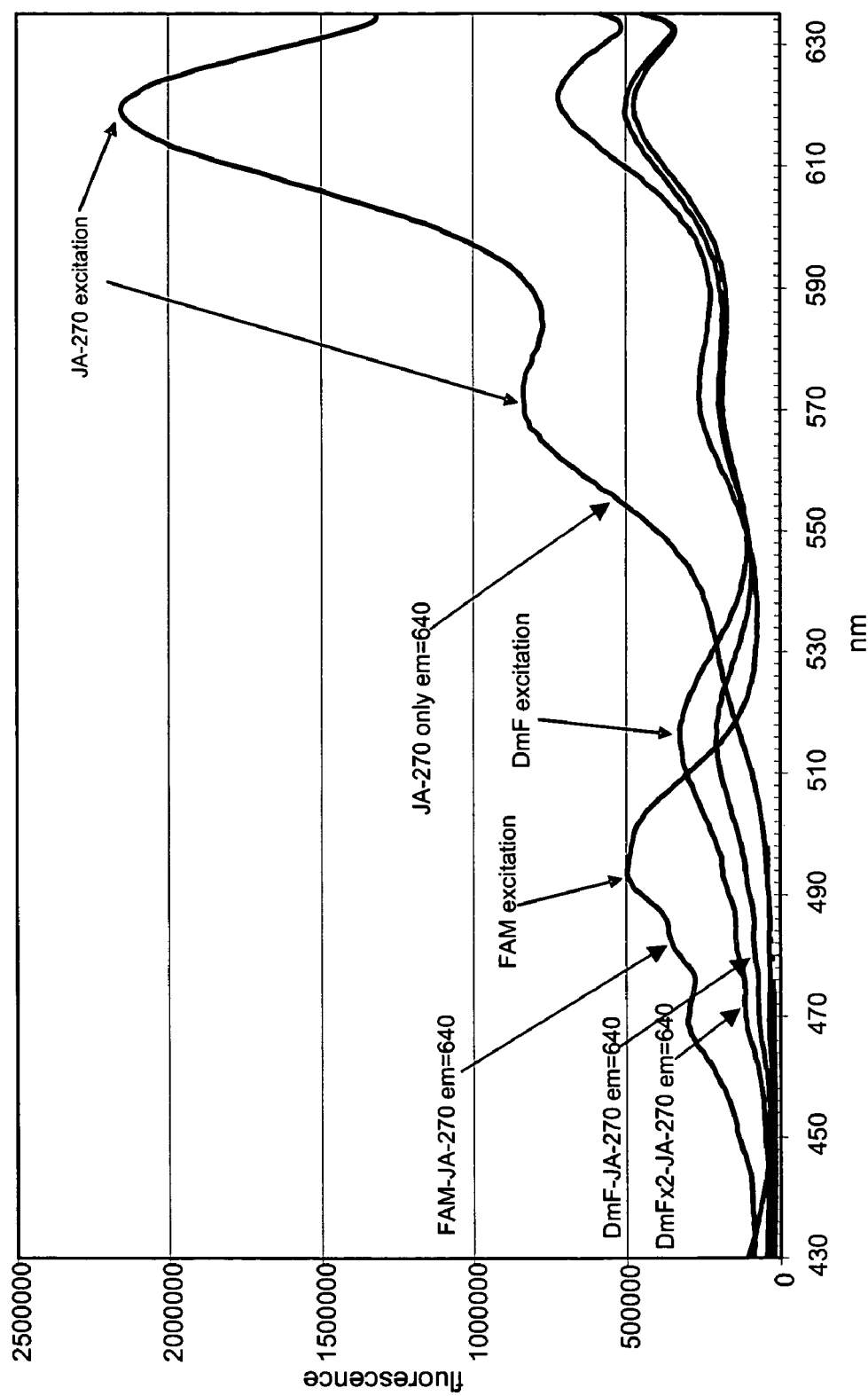
FIG. 44A is a plot of overlaid spectra obtained from excitation scans of hybridization probe assays that involved acceptor probes labeled with JA-270 and donor probes labeled with FAM or DmF.
Figure 44B:
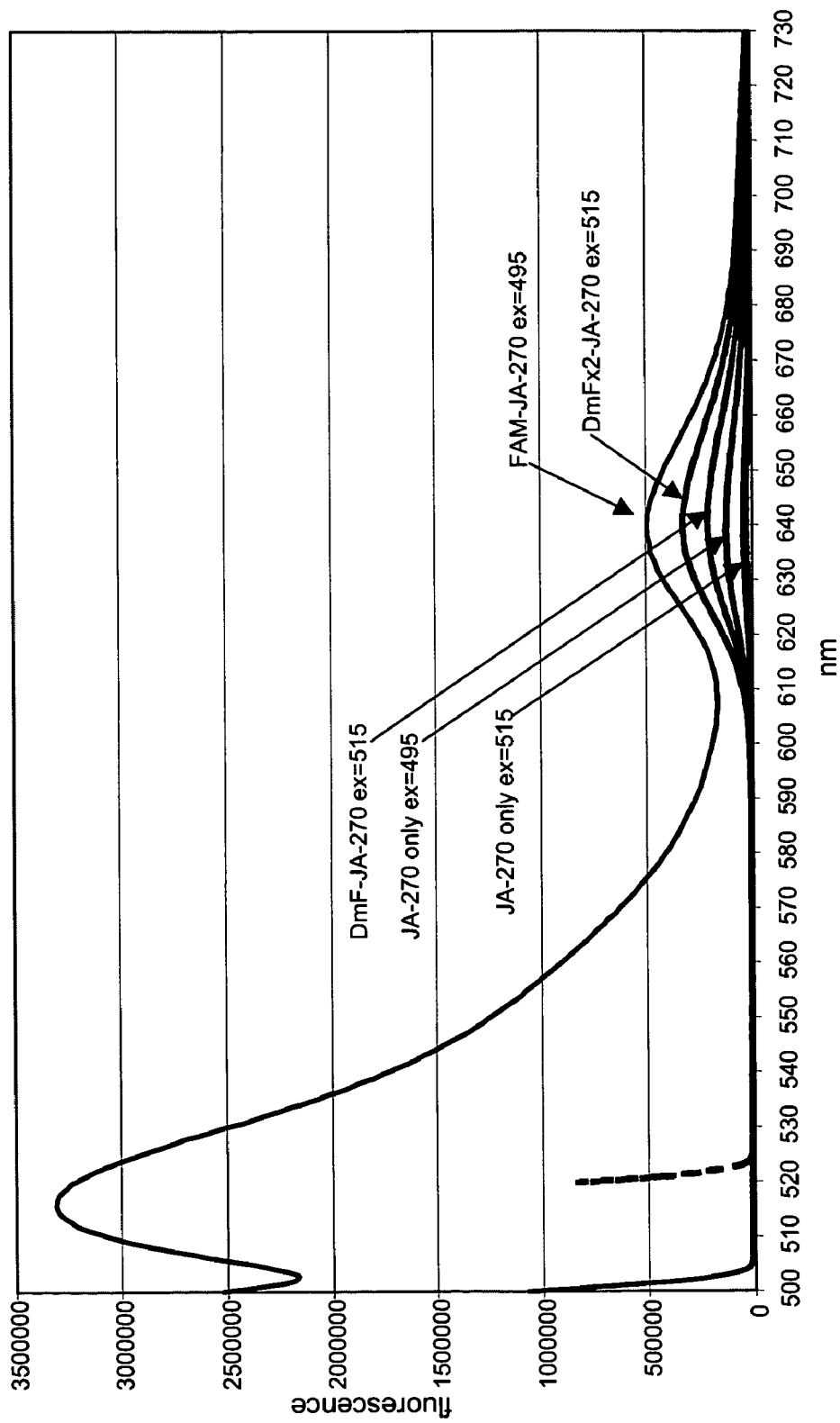
FIG. 44B is a plot of overlaid spectra obtained from emission scans (absolute fluorescence) of hybridization probe assays that involved acceptor probes labeled with JA-270 and donor probes labeled with FAM or DmF.
Figure 44C:
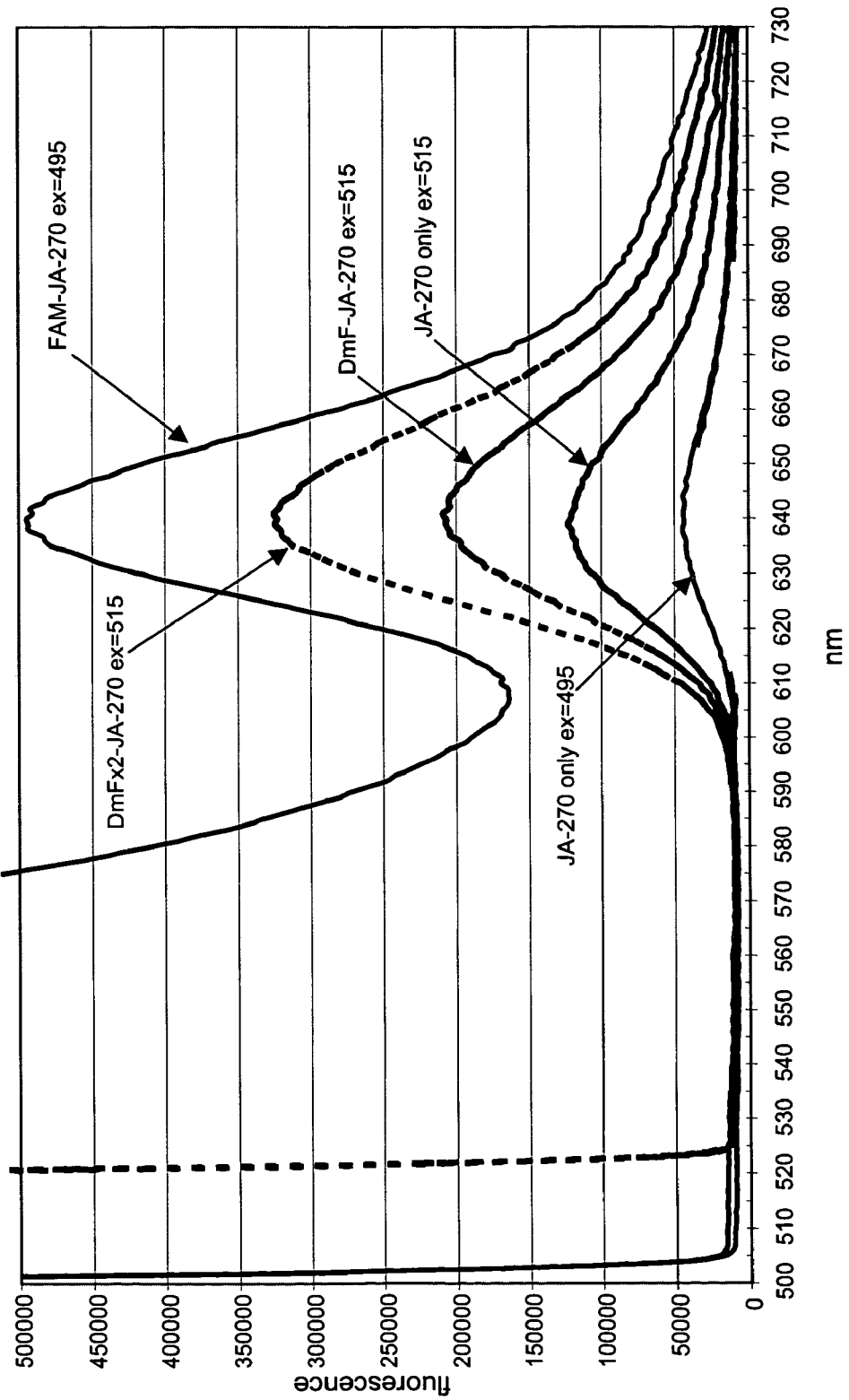
FIG. 44C is a plot of overlaid spectra obtained from the emission scans plotted in FIG. 44B in which the fluorescent emissions have been scaled.

FIG. 44A is an overlaid plot of excitation scans (the ordinate represents absolute fluorescence, while the abscissa represents wavelength (nm)) of hybridization probe assays that involved acceptor probes labeled with JA-270 (emission maximum=640 nm) and donor probes labeled with FAM, DmF, or DmFx2. The excitation peaks of FAM, DmF, and JA-270 are also shown. The emission wavelength (nm) for each trace is indicated (em). As also shown, a scan for a negative control that included only the acceptor probe (JA-270 only em=640) in the reaction mixture was also obtained. FIG. 44B is an overlaid plot of emission scans (the ordinate represents absolute fluorescence, while the abscissa represents wavelength (nm)) of these hybridization probe assays that involved acceptor probes labeled with JA-270 and donor probes labeled with FAM, DmF, or DmFx2. The excitation wavelength (nm) corresponding to each trace is indicated (ex). As also shown, scans for negative controls that included only the acceptor probe in the reaction mixture were also obtained at an excitation wavelength of 495 nm (JA-270 only ex=495) and at an excitation wavelength of 515 nm (JA-270 only ex=515). FIG. 44C is an overlaid plot of the emission scans plotted in FIG. 44B in which the relative fluorescent emissions are provided.

Figure 45A:
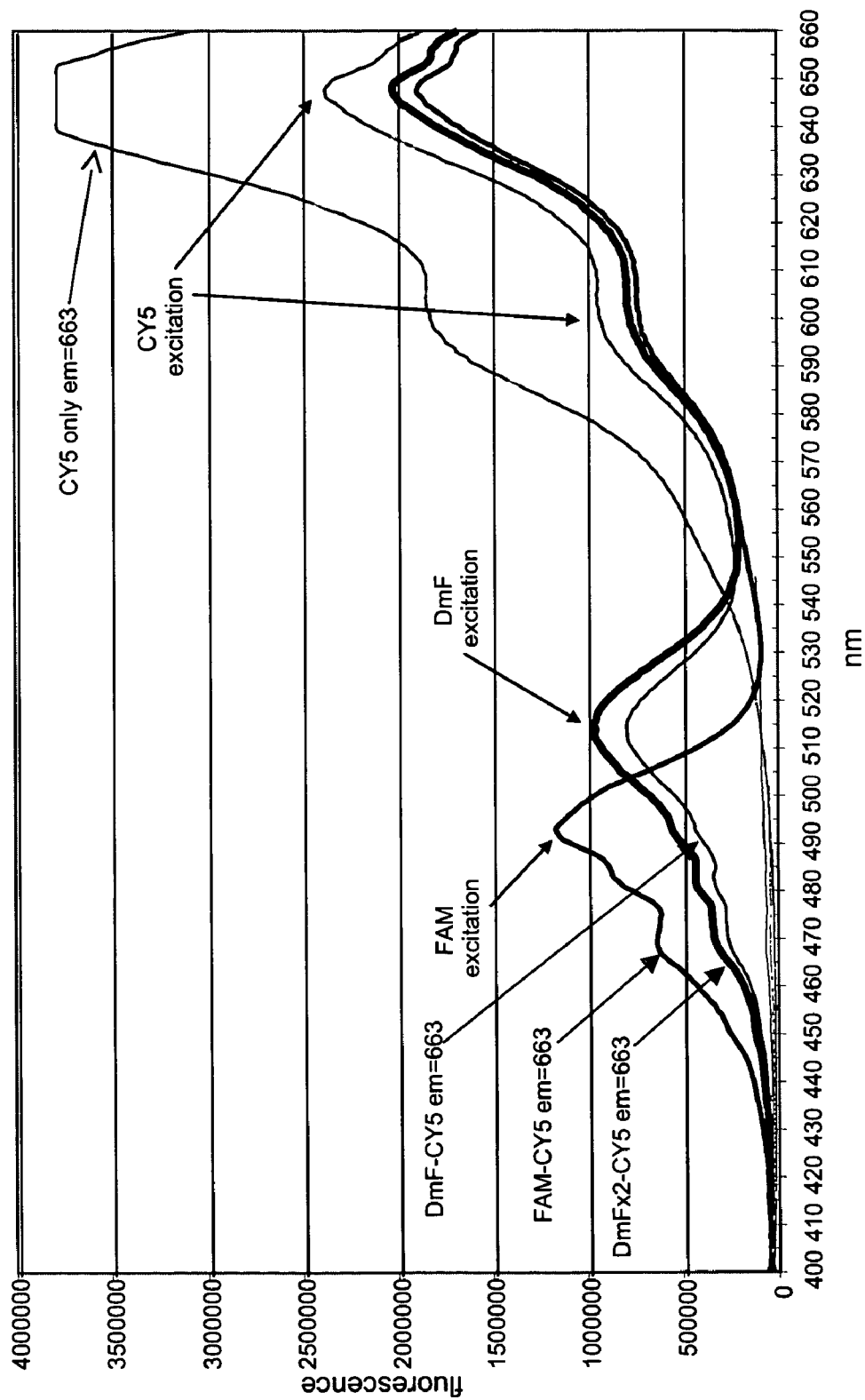
FIG. 45A is a plot of overlaid spectra obtained from excitation scans of hybridization probe assays that involved acceptor probes labeled with CY5 and donor probes labeled with FAM or DmF.
Figure 45B:
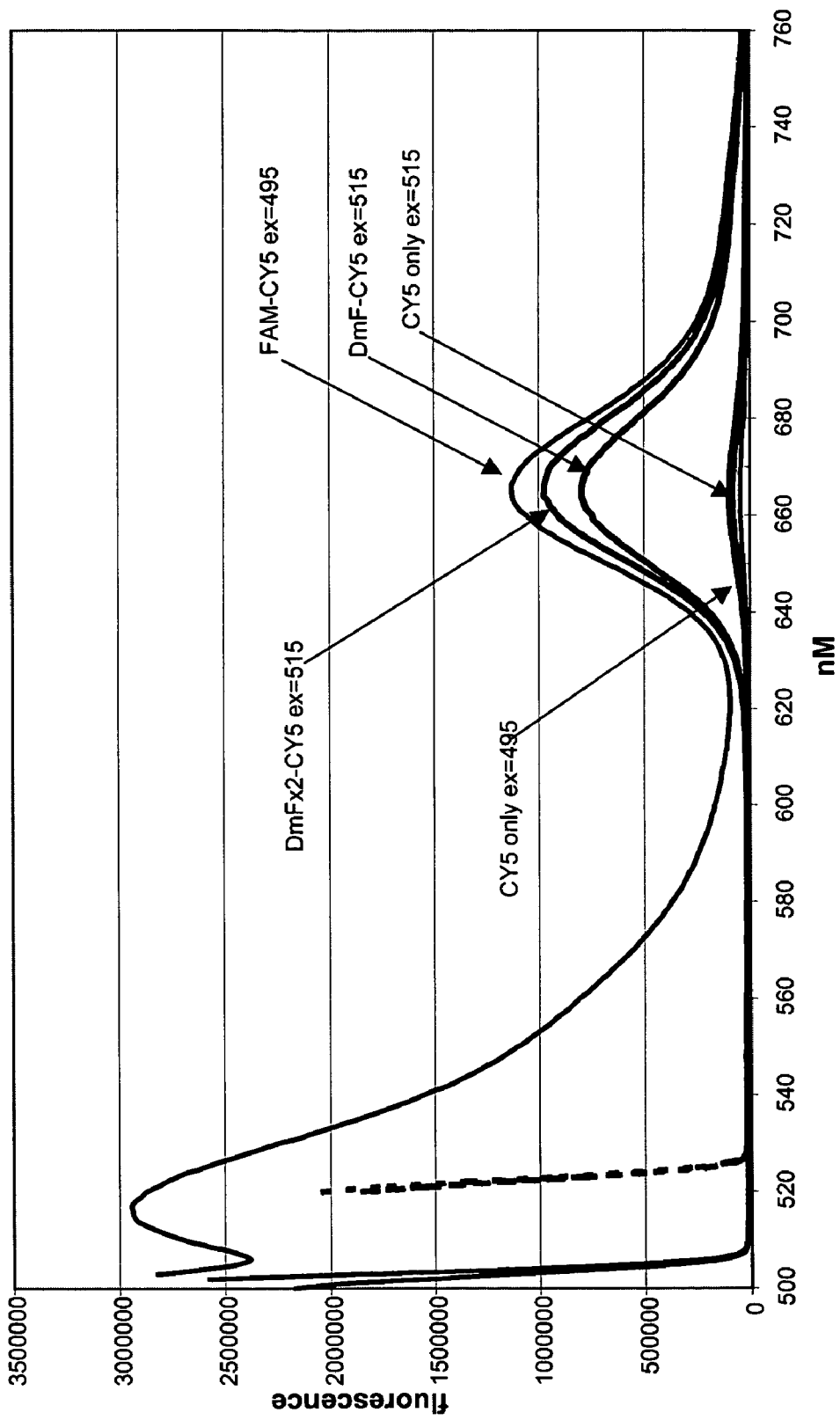
FIG. 45B is a plot of overlaid spectra obtained from emission scans (absolute fluorescence) of hybridization probe assays that involved acceptor probes labeled with CY5 and donor probes labeled with FAM or DmF.
Figure 45C:
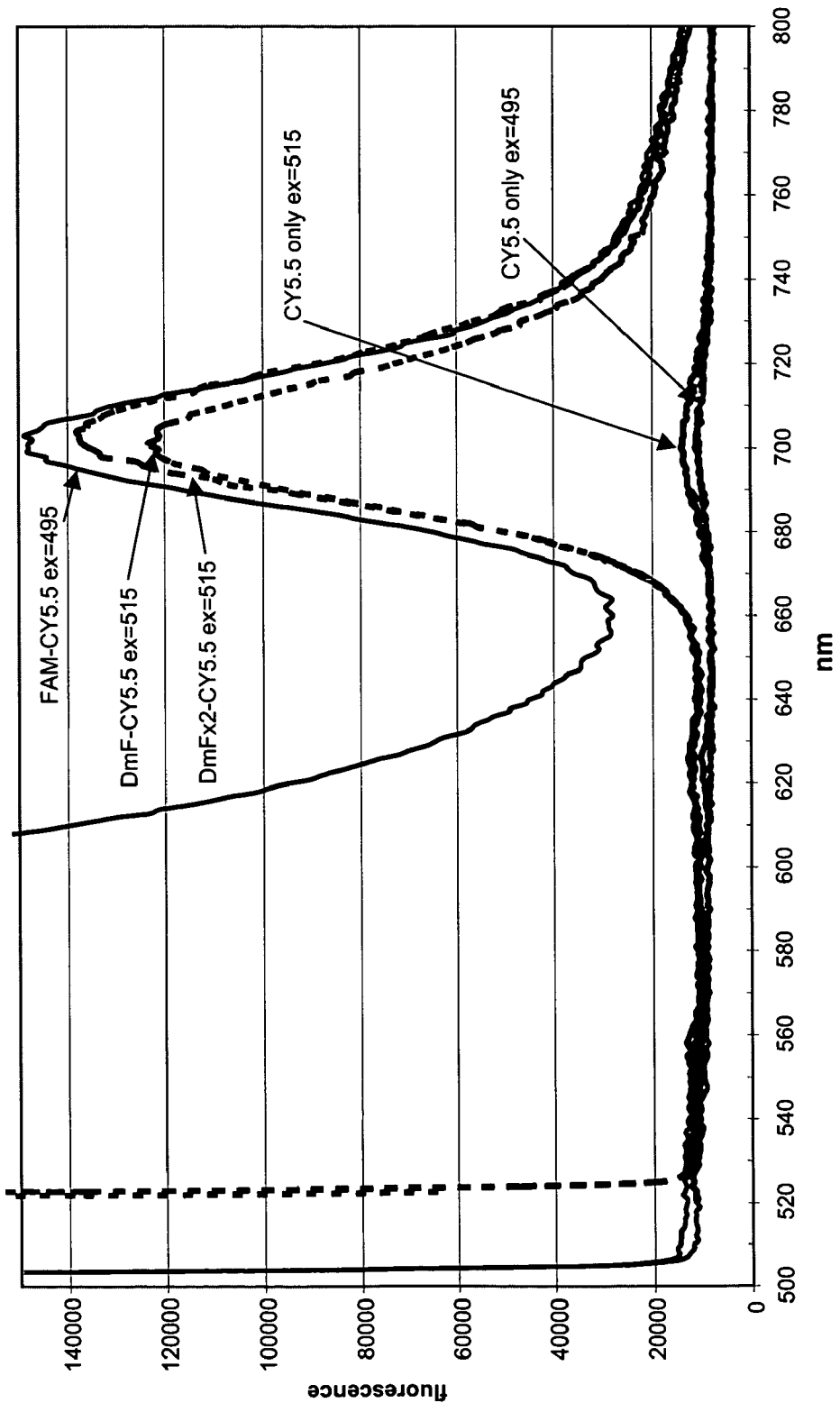
FIG. 45C is a plot of overlaid spectra obtained from the emission scans plotted in FIG. 45B in which the fluorescent emissions have been scaled.

FIG. 45A is an overlaid plot of excitation scans (the ordinate represents absolute fluorescence, while the abscissa represents wavelength (nm)) of hybridization probe assays that involved acceptor probes labeled with CY5 (emission maximum=663 nm) and donor probes labeled with FAM, DmF, or DmFx2. The excitation peaks of FAM, DmF, and CY5 are also shown. The emission wavelength (nm) for each trace is indicated (em). As also shown, a scan for a negative control that included only the acceptor probe (CY5 only em=663) in the reaction mixture was also obtained. FIG. 45B is an overlaid plot of emission scans (the ordinate represents absolute fluorescence, while the abscissa represents wavelength (nm)) of these hybridization probe assays that involved acceptor probes labeled with CY5 and donor probes labeled with FAM, DmF, or DmFx2. The excitation wavelength (nm) corresponding to each trace is indicated (ex). As also shown, scans for negative controls that included only the acceptor probe in the reaction mixture were also obtained at an excitation wavelength of 495 nm (CY5 only ex=495) and at an excitation wavelength of 515 nm (CY5 only ex=515). FIG. 45C is an overlaid plot of the emission scans plotted in FIG. 45B in which the relative fluorescent emissions are provided.

Figure 46A:
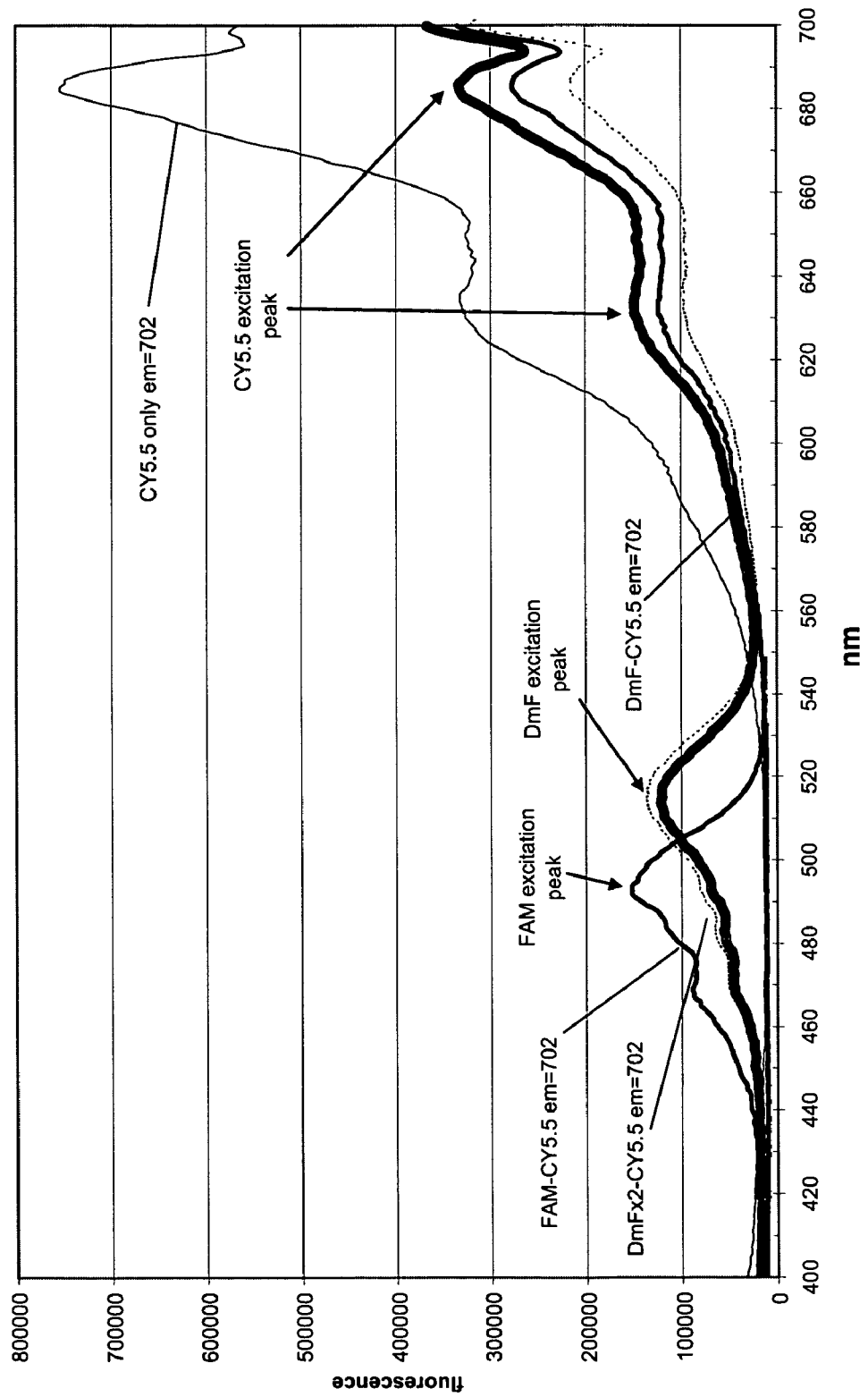
FIG. 46A is a plot of overlaid spectra obtained from excitation scans of hybridization probe assays that involved acceptor probes labeled with CY5.5 and donor probes labeled with FAM or DmF.
Figure 46B:
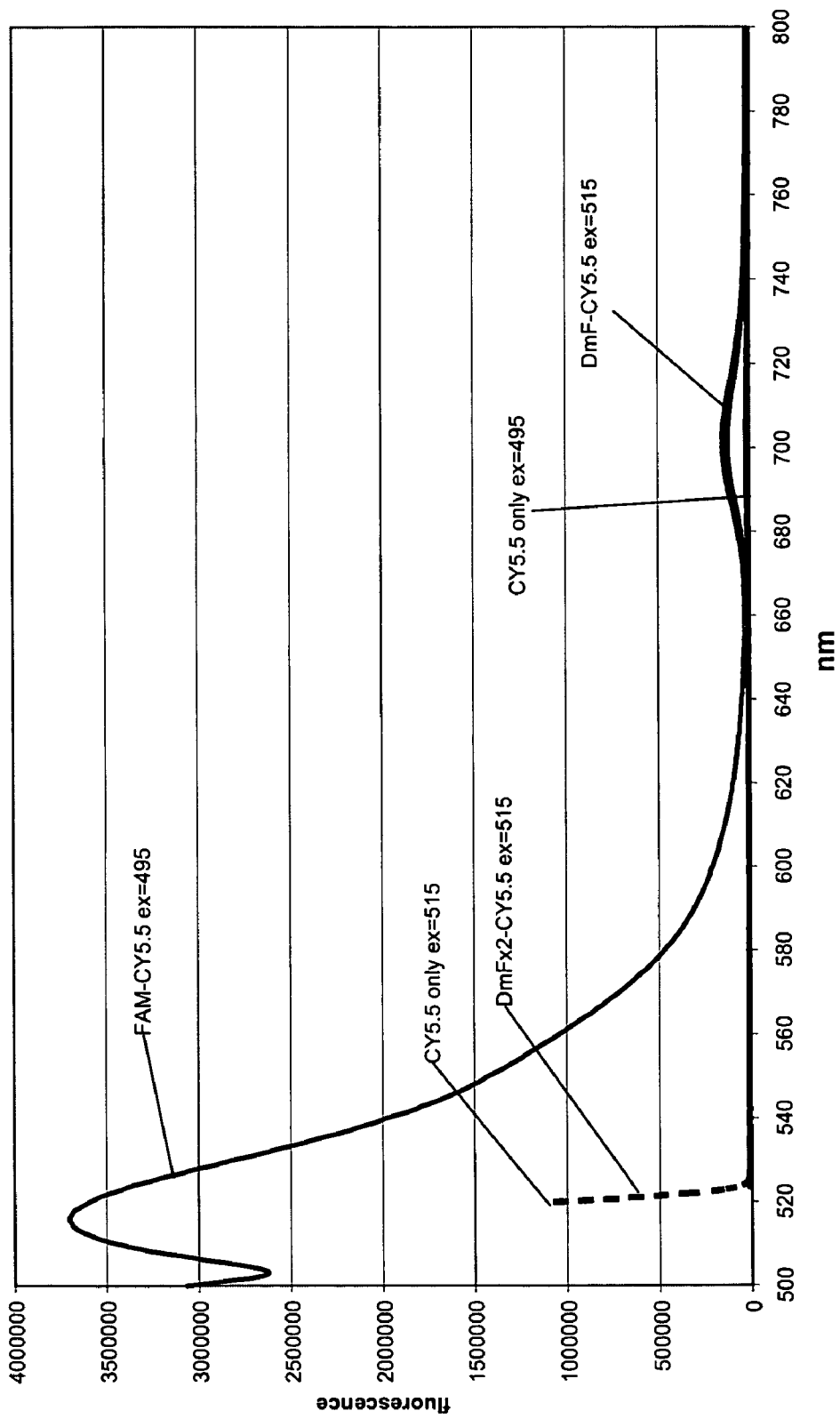
FIG. 46B is a plot of overlaid spectra obtained from emission scans (absolute fluorescence) of hybridization probe assays that involved acceptor probes labeled with CY5.5 and donor probes labeled with FAM or DmF.
Figure 46C:
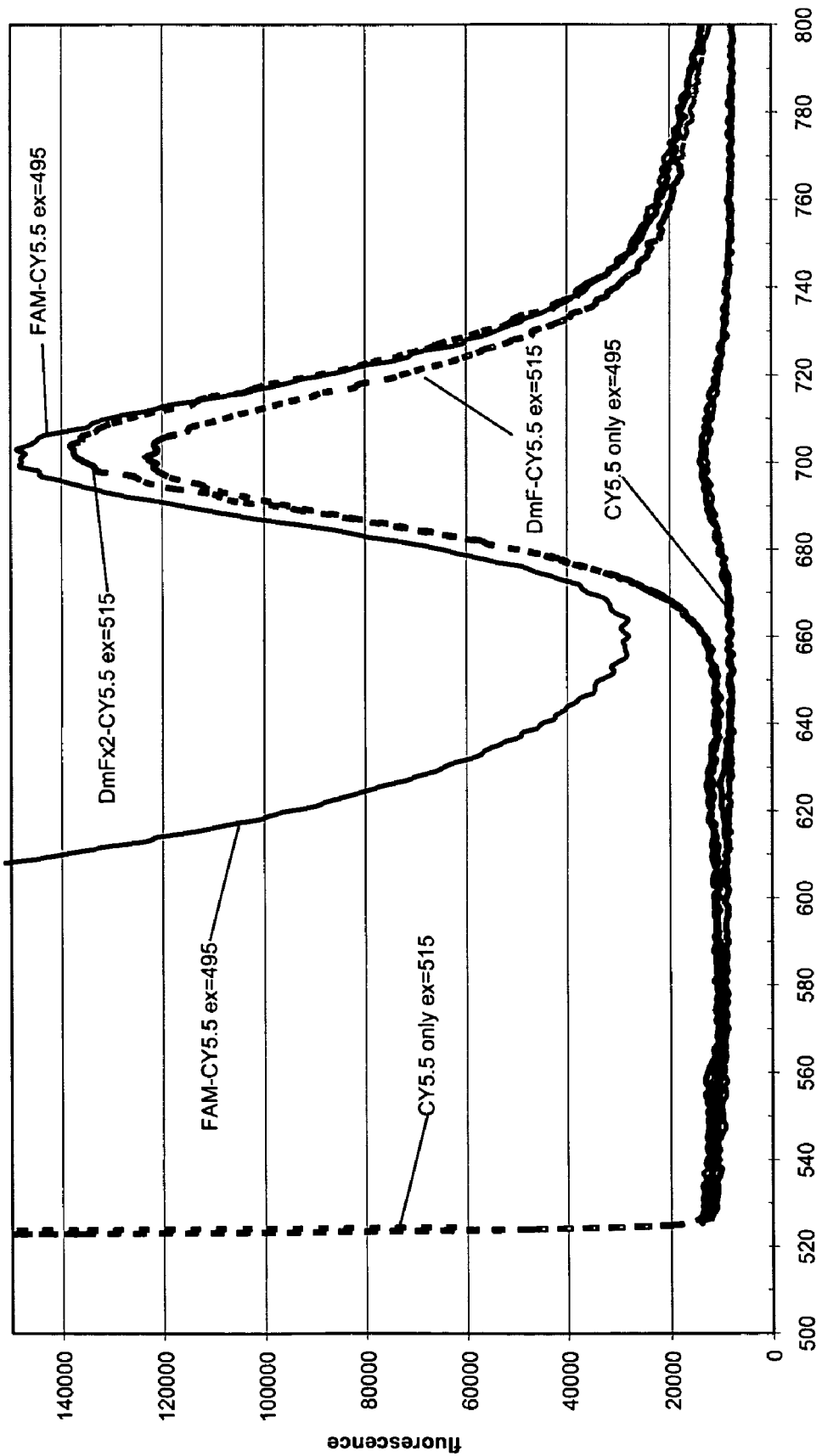
FIG. 46C is a plot of overlaid spectra obtained from the emission scans plotted in FIG. 46B in which the fluorescent emissions have been scaled.

FIG. 46A is an overlaid plot of excitation scans (the ordinate represents absolute fluorescence, while the abscissa represents wavelength (nm)) of hybridization probe assays that involved acceptor probes labeled with CY5.5 (emission maximum=702 nm) and donor probes labeled with FAM, DmF, or DmFx2. The excitation peaks of FAM, DmF, and CY5.5 are also shown. The emission wavelength (nm) for each trace is indicated (em). As also shown, a scan for a negative control that included only the acceptor probe (CY5.5 only em=702) in the reaction mixture was also obtained. FIG. 46B is an overlaid plot of emission scans (the ordinate represents absolute fluorescence, while the abscissa represents wavelength (nm)) of these hybridization probe assays that involved acceptor probes labeled with CY5.5 and donor probes labeled with FAM, DmF, or DmFx2. The excitation wavelength (nm) corresponding to each trace is indicated (ex). As also shown, scans for negative controls that included only the acceptor probe in the reaction mixture were also obtained at an excitation wavelength of 495 nm (CY5.5 only ex=495) and at an excitation wavelength of 515 nm (CY5.5 only ex=515). FIG. 46C is an overlaid plot of the emission scans plotted in FIG. 46B in which the relative fluorescent emissions are provided.

Figure 47B:
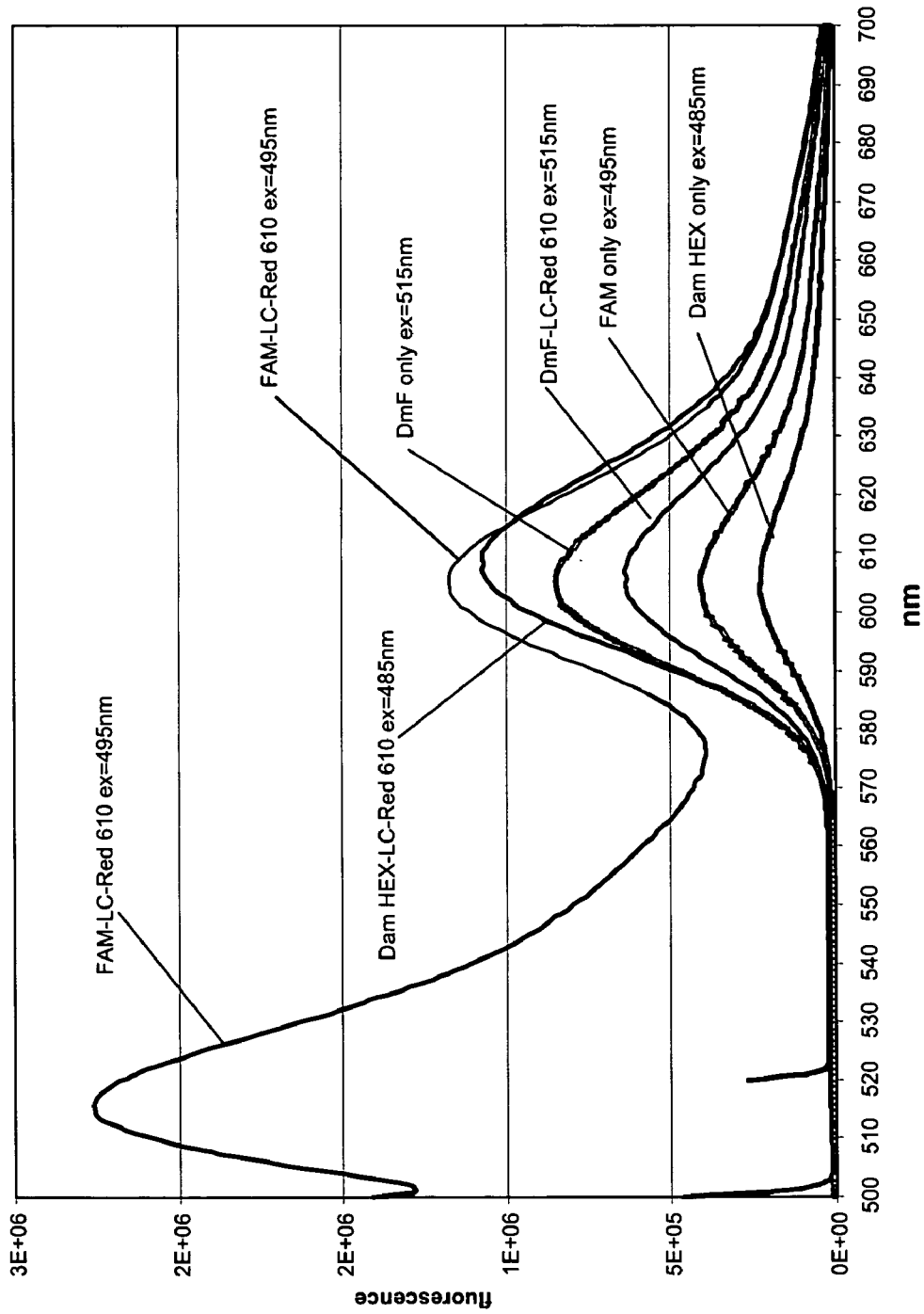
FIG. 47B is a plot of overlaid spectra obtained from emission scans (absolute fluorescence) of hybridization probe assays that involved acceptor probes labeled with LC-Red 610 and donor probes labeled with FAM, DmF, or Dam HEX.

FIG. 47A is an overlaid plot of excitation scans (the ordinate represents absolute fluorescence, while the abscissa represents wavelength (nm)) of hybridization probe assays that involved acceptor probes labeled with LC610 (emission maximum=604 nm) and donor probes labeled with FAM, DmF, or Dam HEX (i.e., 6-carboxy-aminopentachlorofluorescein). The emission wavelength (nm) for each trace is indicated (em). As also shown, a scan for a negative control that included only the acceptor probe (LC-Red 610 only em=605) in the reaction mixture was also obtained. FIG. 47B is an overlaid plot of emission scans (the ordinate represents absolute fluorescence, while the abscissa represents wavelength (nm)) of these hybridization probe assays that involved acceptor probes labeled with LC-Red 610 and donor probes labeled with FAM, DmF, or Dam HEX. The excitation wavelength (nm) corresponding to each trace is indicated (ex). As also shown, scans for negative controls that included only the donor probes in the reaction mixtures were also obtained (FAM only ex=495 nm, DmF only ex=515 nm, and Dam HEX only ex=485 nm).

Figure 48A:
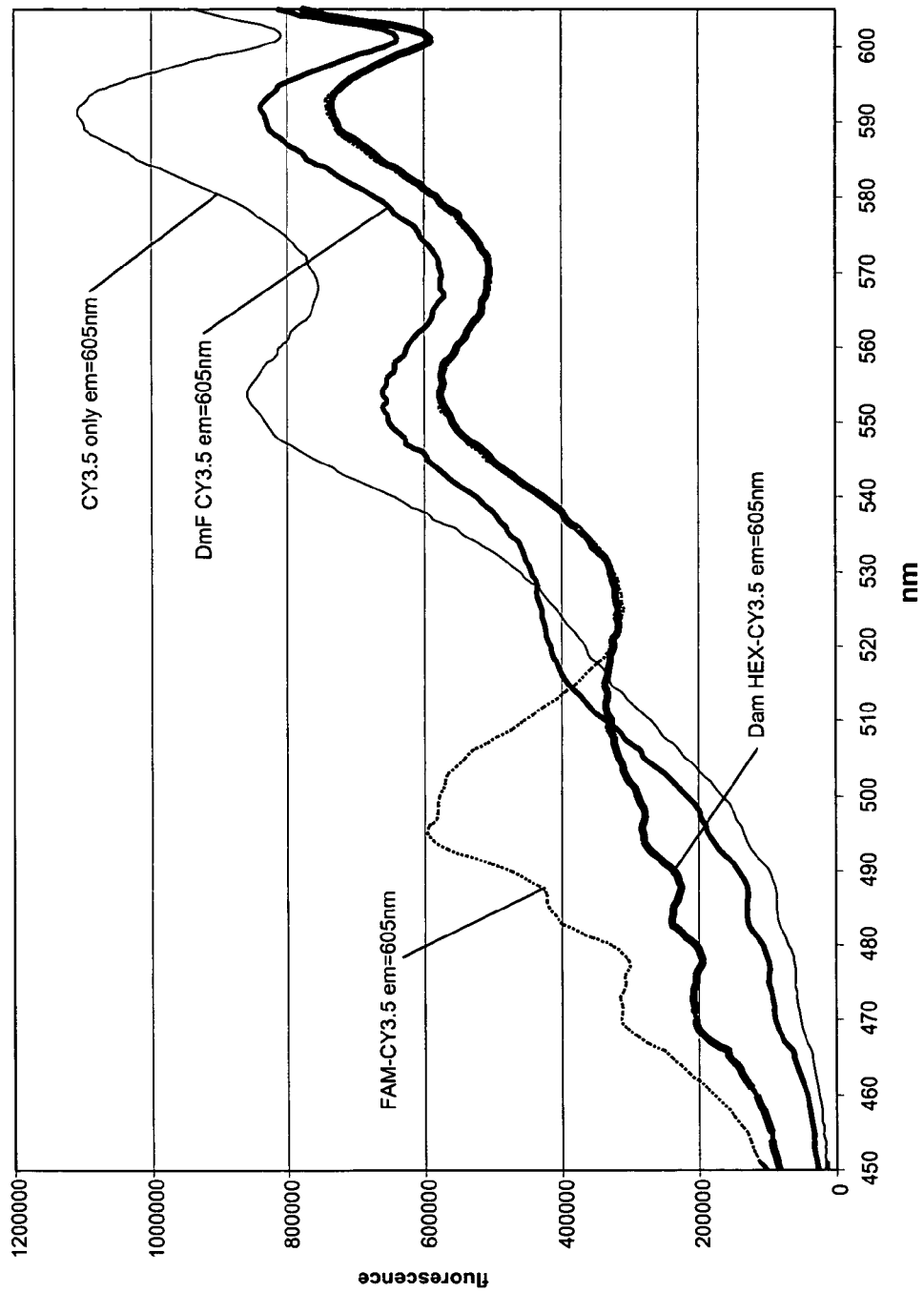
FIG. 48A is a plot of overlaid spectra obtained from excitation scans of hybridization probe assays that involved acceptor probes labeled with CY3.5 and donor probes labeled with FAM, DmF, or Dam HEX.
Figure 48B:
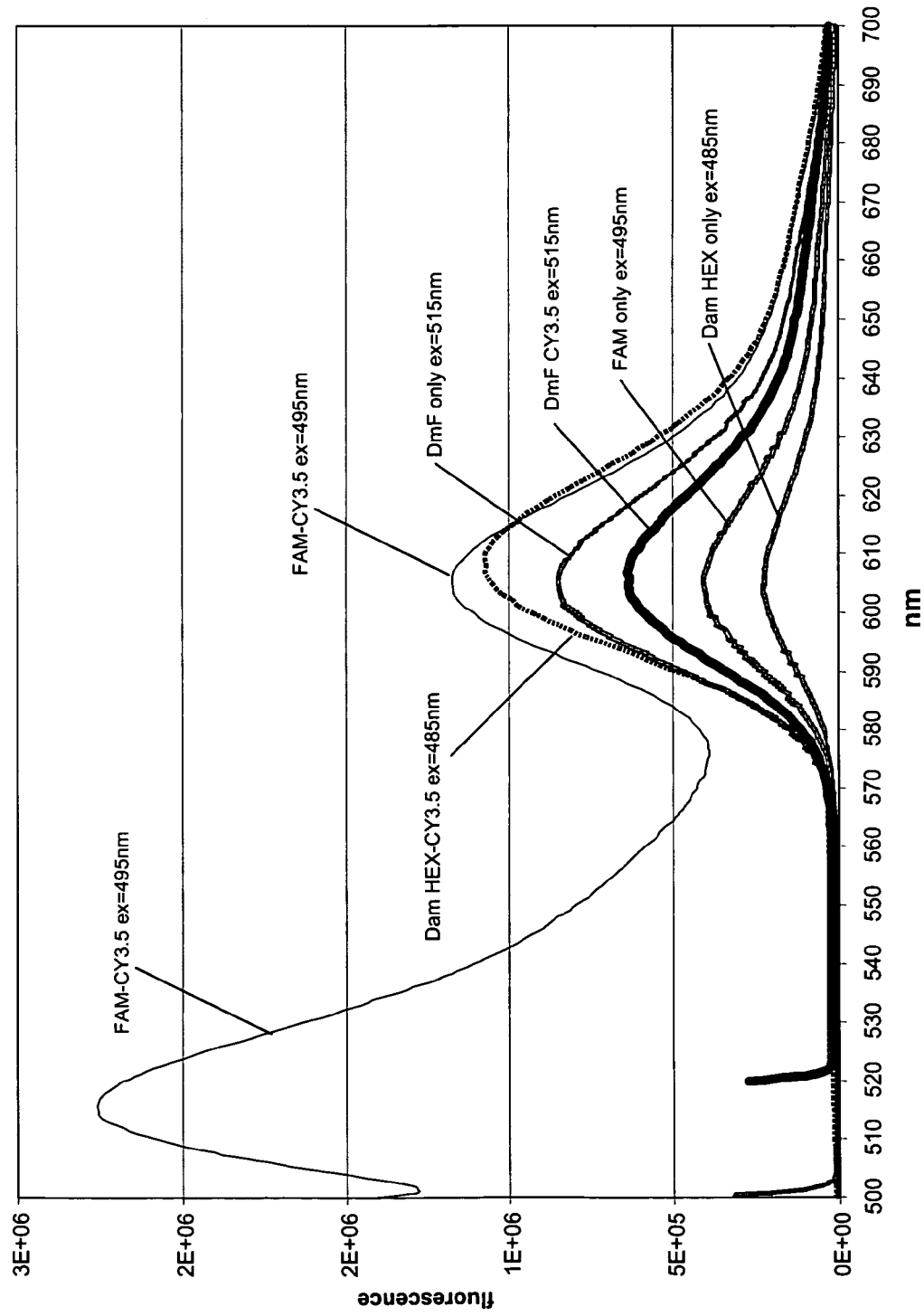
FIG. 48B is a plot of overlaid spectra obtained from emission scans (absolute fluorescence) of hybridization probe assays that involved acceptor probes labeled with CY3.5 and donor probes labeled with FAM, DmF, or Dam HEX.

FIG. 48A is an overlaid plot of excitation scans (the ordinate represents absolute fluorescence, while the abscissa represents wavelength (nm)) of hybridization probe assays that involved acceptor probes labeled with CY3.5 and donor probes labeled with FAM, DmF, or Dam HEX. The emission wavelength (nm) for each trace is indicated (em). As also shown, a scan for a negative control that included only the acceptor probe (CY3.5 only em=605) in the reaction mixture was also obtained. FIG. 48B is an overlaid plot of emission scans (the ordinate represents absolute fluorescence, while the abscissa represents wavelength (nm)) of these hybridization probe assays that involved acceptor probes labeled with CY3.5 and donor probes labeled with FAM, DmF, or Dam HEX. The excitation wavelength (nm) corresponding to each trace is indicated (ex). As also shown, scans for negative controls that included only the donor probes in the reaction mixtures were also obtained (FAM only ex=495 nm, DmF only ex=515 nm, and Dam HEX only ex=485 nm).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A biomolecule comprising a single substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy; wherein the substantially non-fluorescent donor moiety is selected from the group consisting of: 6-carboxy-aminopentachlorofluorescein, or 5-carboxy-aminopentachlorofluorescein.

2. The biomolecule of claim 1, wherein peak visible absorbances of the substantially non-fluorescent donor moiety and the acceptor moiety differ from one another by about 100 nm or more.

3. The biomolecule of claim 1, wherein the substantially non-fluorescent donor moiety is attached to the biomolecule via at least one linker moiety.

4. The biomolecule of claim 1, wherein the biomolecule comprises at least one nucleoside, at least one amino acid, at least one sugar, and/or at least one lipid.

5. The biomolecule of claim 1, wherein the biomolecule comprises at least one quencher moiety.

6. The biomolecule of claim 1, wherein the biomolecule comprises a biopolymer synthesis reagent.

7. The biomolecule of claim 6, wherein the biopolymer synthesis reagent comprises a phosphoramidite.

8. The biomolecule of claim 1, wherein the biomolecule comprises the acceptor moiety.

9. The biomolecule of claim 8, wherein the acceptor moiety comprises a fluorescent dye.

10. The biomolecule of claim 8, wherein the biomolecule comprises a biopolymer.

11. The biomolecule of claim 10, wherein different monomer units of the biopolymer comprise the substantially non-fluorescent donor moiety and the acceptor moiety.

12. The biomolecule of claim 10, wherein a monomer unit of the biopolymer comprises both the substantially non-fluorescent donor moiety and the acceptor moiety.

13. The biomolecule of claim 1, wherein the biomolecule comprises at least one oligonucleotide or at least one polynucleotide.

14. A reaction mixture, comprising at least one nucleotide, at least one primer nucleic acid, and/or at least a first probe nucleic acid, wherein one or more of the nucleotide, the primer nucleic acid, or the first probe nucleic acid comprises a single substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy;
    wherein the substantially non-fluorescent donor moiety is selected from the group consisting of: 6-carboxy-aminopentachlorofluorescein, or 5-carboxy-aminopentachlorofluorescein.

15. The reaction mixture of claim 14, wherein peak visible absorbances of the substantially non-fluorescent donor moiety and the acceptor moiety differ from one another by about 100 nm or more.

16. The reaction mixture of claim 14, comprising at least one nucleotide incorporating biocatalyst.

17. The reaction mixture of claim 14, wherein the nucleotide comprises an extendible nucleotide and/or a terminator nucleotide.

18. The reaction mixture of claim 14, wherein the first probe nucleic acid comprises a 5'-nuclease probe or a hairpin probe.

19. The reaction mixture of claim 14, wherein the nucleotide, the primer nucleic acid, or the first probe nucleic acid comprises the acceptor moiety.

20. The reaction mixture of claim 19, wherein the nucleotide, the primer nucleic acid, or the first probe nucleic acid comprises at least one quencher moiety.

21. The reaction mixture of claim 19, wherein the acceptor moiety comprises a fluorescent dye.

22. A reaction mixture comprising at least a first biopolymer synthesis reagent that comprises a single substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy and the substantially non-fluorescent donor moiety is selected from the group consisting of: 6-carboxy-aminopentachlorofluorescein, or 5-carboxy-aminopentachiorofluorescein.

23. A kit, comprising at least a first biomolecule comprising a single substantially non-fluorescent donor moiety that is capable of transferring non-fluorescent energy to at least one acceptor moiety when the acceptor moiety is sufficiently proximal to the substantially non-fluorescent donor moiety such that the acceptor moiety emits light in response to the accepted non-fluorescent energy and the substantially non-fluorescent donor moiety is selected from the group consisting of:
    6-carboxy-aminopentachlorofluorescein, or 5-carboxy-aminopentachlorofluorescein.

* * * * *